United States Patent [19]
Breault et al.

[11] Patent Number: 5,965,741
[45] Date of Patent: Oct. 12, 1999

[54] ORTHO-SUBSTITUTED AROMATIC ETHER COMPOUNDS AND THEIR USE IN PHARMACEUTICAL COMPOSITIONS FOR PAIN RELIEF

[75] Inventors: Gloria Anne Breault, Congleton; Howard Tucker, Macclesfield; John Oldfield, Wilmslow; Peter Warner, Macclesfield, all of United Kingdom

[73] Assignee: Zeneca Limited, United Kingdom

[21] Appl. No.: 08/793,023

[22] PCT Filed: Aug. 29, 1995

[86] PCT No.: PCT/GB95/02030

§ 371 Date: Feb. 21, 1997

§ 102(e) Date: Feb. 21, 1997

[87] PCT Pub. No.: WO96/06822

PCT Pub. Date: Mar. 7, 1996

[30] Foreign Application Priority Data

Aug. 31, 1994 [GB] United Kingdom .................. 9417532

[51] Int. Cl.⁶ ............... C07D 213/40; C07D 257/04; C07C 65/21; C07C 317/18; A61K 31/19; A61K 31/275

[52] U.S. Cl. .............. 548/252; 514/277; 514/357; 514/365; 514/381; 514/522; 514/557; 514/561; 514/568; 546/270.4; 546/336; 546/337; 548/201; 548/204; 562/429; 562/455; 562/459; 562/473; 562/474; 562/475; 562/480

[58] Field of Search ...................... 562/473, 474, 562/475, 471, 433, 429, 455, 459, 480; 548/252, 201, 204; 558/423, 425; 546/270.4, 336, 337; 514/557, 561, 568, 522, 381, 365, 277, 357

[56] References Cited

U.S. PATENT DOCUMENTS

| | | | |
|---|---|---|---|
| 3,632,760 | 1/1972 | Shen et al. | 424/230 |
| 3,657,430 | 4/1972 | Shen et al. | 424/230 |
| 4,578,390 | 3/1986 | Jensen et al. | 514/255 |
| 4,582,857 | 4/1986 | Grill et al. | 514/563 |
| 4,994,479 | 2/1991 | Mase et al. | 514/381 |
| 5,025,036 | 6/1991 | Carson et al. | 514/568 |
| 5,087,743 | 2/1992 | Janssen et al. | 562/460 |
| 5,105,017 | 4/1992 | Dillard | 568/64 |
| 5,189,033 | 2/1993 | Tucker | 514/211 |
| 5,262,432 | 11/1993 | Koenig et al. | 514/381 |
| 5,317,101 | 5/1994 | Oldfield et al. | 540/488 |
| 5,324,743 | 6/1994 | Dillard et al. | 514/456 |
| 5,393,768 | 2/1995 | Dillard | 514/381 |
| 5,409,930 | 4/1995 | Spada et al. | 514/248 |
| 5,420,270 | 5/1995 | Chandrakumar et al. | 540/488 |
| 5,441,950 | 8/1995 | Collins et al. | 514/211 |
| 5,480,883 | 1/1996 | Spada et al. | 514/249 |
| 5,552,420 | 9/1996 | Aldous et al. | 514/364 |
| 5,608,104 | 3/1997 | Ohkawa et al. | 562/473 |
| 5,654,331 | 8/1997 | Bernardon | 514/532 |
| 5,656,619 | 8/1997 | Janssen et al. | 514/100 |

FOREIGN PATENT DOCUMENTS

| | | |
|---|---|---|
| 2111035 | 6/1994 | Canada . |
| 0122321 | 10/1984 | European Pat. Off. . |
| 0193822 | 9/1986 | European Pat. Off. . |
| 0200101 | 12/1986 | European Pat. Off. . |
| 0218077 | 4/1987 | European Pat. Off. . |
| 0534667 | 3/1991 | European Pat. Off. . |
| 0475206 | 3/1992 | European Pat. Off. . |
| 0480641 | 4/1992 | European Pat. Off. . |
| 0752421 | 1/1997 | European Pat. Off. . |
| 1560281 | 2/1980 | United Kingdom . |
| 2041363 | 9/1986 | United Kingdom . |
| 92/20642 | 11/1992 | WIPO . |
| 96/03380 | 2/1996 | WIPO . |
| 96/06822 | 3/1996 | WIPO . |
| 96/11902 | 4/1996 | WIPO . |
| 97/00863 | 1/1997 | WIPO . |
| 97/00864 | 1/1997 | WIPO . |

OTHER PUBLICATIONS

Derwent Patent Abstract of DE 2,701,854 (Abstract No. 52629Y/30). Wieckmann et al.

Brown et al., J. Med. Chem 1989, 32, 807–826.

*Primary Examiner*—Floyd D. Higel
*Attorney, Agent, or Firm*—Kenneth F. Mitchell

[57] ABSTRACT

The invention provides compounds of formula I:

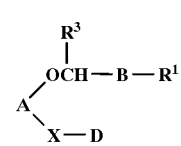

(I)

wherein A, B, D, X, R¹, and R³ have any of the values defined in the specification, as well as N-oxides thereof, S-oxides thereof, pharmaceutically acceptable salts thereof, and in vivo hydrolizable esters and amides thereof, that are useful to relieve pain. The invention also provides pharmaceutical compositions as well as synthetic and therapeutic methods relating to such compounds.

10 Claims, No Drawings

ORTHO-SUBSTITUTED AROMATIC ETHER COMPOUNDS AND THEIR USE IN PHARMACEUTICAL COMPOSITIONS FOR PAIN RELIEF

This application is a national stage filing under 35 U.S.C. §371 of PCT/GB95/02030, filed Aug. 29, 1995.

This invention relates to novel, aromatic compounds and pharmaceutically-acceptable salts thereof which possess useful pharmacological properties. More particularly the compounds of the invention are antagonists of the pain enhancing effects of E-type prostaglandins. The invention also relates to processes for the manufacture of the aromatic compounds and pharmaceutically-acceptable salts thereof; to novel pharmaceutical compositions containing them; and to use of the compounds in pain relief.

The compounds of the invention are useful in the treatment of pain such as the pain associated with joint conditions (such as rheumatoid arthritis and osteoarthritis), post-operative pain, post-partum pain, the pain associated with dental conditions (such as dental caries and gingivitis), the pain associated with burns (including sunburn), the treatment of bone disorders (such as osteoporosis, hypercalcaemia of malignancy and Paget's disease), the pain associated with sports injuries and sprains and all other painful conditions in which E-type prostaglandins wholly or in part play a pathophysiological role.

Non-steroidal anti-inflammatory drugs (NSAIDS) and opiates are the main classes of drugs in pain relief. However both possess undesireable side effects. NSAIDS are known to cause gastrointestinal irritation and opiates are known to be addictive.

We have now found a class of compounds structurally different to NSAIDS and opiates, and useful in relief of pain.

The compounds of the invention may also possess anti-inflammatory, anti-pyretic and anti-diarrhoeal properties and be effective in other conditions in which prostaglandin $E_2$ ($PGE_2$) wholly or in part plays a pathophysiological role.

According to the invention there is provided a compound of the formula I;

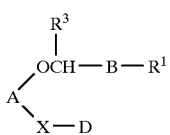

(I)

wherein:

A is an optionally substituted: 8- to 10-membered bicyclic heteroaryl, 5- or 6-membered heteroaryl, naphthyl or phenyl; provided that the —OCH($R^3$)- and -X- linking groups are positioned in a 1,2 relationship to one another on ring carbon atoms;

B is an optionally substituted 5- or 6-membered heteroaryl ring system or optionally substituted phenyl;

D is optionally substituted: pyridyl, pyrazinyl, pyrimidinyl, pyridazinyl, pyrrolyl, thienyl, furyl, pyrazolyl, thiazolyl, isothiazolyl, oxazolyl, isoxazolyl or phenyl;

X is of the formula —(CHR$^4$)$_n$—or—(CHR$^4$)$_p$CR$^4$=CR$^4$(CHR$^4$)$_q$—wherein n is 1 to 3 and p and q are either both 0 or one of p and q is 1 and the other is 0;

$R^1$ is positioned on ring B in a 1,3 or 1,4 relationship with the —OCH($R^3$)— linking group in 6-membered rings and in a 1,3 relationship with the —OCH(R3)— linking group in 5-membered rings and is carboxy, carboxyC$_{1-3}$alkyl, tetrazolyl, tetrazolylC$_{1-3}$alkyl, tetronic acid, hydroxamic acid, sulphonic acid, or $R^1$ is of the formula —CONR$^a$ R$^{a1}$ wherein R$^a$ is hydrogen or C$_{1-6}$ alkyl and R$^{a1}$ is hydrogen or optionally substituted; C$_{1-6}$alkyl, C$_{2-6}$alkenyl, C$_{2-6}$alkynyl, C$_{3-7}$cycloalkyl, C$_{3-7}$cycloalkylC$_{1-6}$alkyl, C$_{3-7}$cycloalkylC$_{2-6}$alkenyl, C$_{3-7}$ cycloalkylC$_{2-6}$ alkynyl, C$_{5-7}$cycloalkenyl, C$_{3-7}$cycloalkenylC$_{1-6}$alkyl, C$_{5-7}$cycloalkenylC$_{2-6}$alkenyl, C$_{5-7}$cycloalkenylC$_{2-6}$alkynyl, C$_{1-3}$alkyl substituted by a 5- or 6-membered saturated or partially saturated heterocyclic ring, 5- or 6-membered heteroaryl C$_{1-3}$alkyl, 5- or 6-membered saturated or partially saturated heterocyclic ring, or 5- or 6-membered heteroaryl; or wherein R$^a$ and R$^{a1}$ together with the amide nitrogen to which they are attached (NR$^a$R$^{a1}$) form an amino acid residue or ester thereof; or $R^1$ is of the formula —CONHSO$_2$R$^b$ wherein R$^b$ is optionally substituted: C$_{1-6}$alkyl, C$_{2-6}$alkenyl, C$_{2-6}$alkynyl, C$_{3-7}$cycloalkyl, C$_{3-7}$cycloalkylC$_{1-6}$alkyl, C$_{3-7}$cycloalkylC$_{2-6}$alkenyl, C$_{3-7}$cycloalkylC$_{2-6}$alkynyl, C$_{5-7}$cycloalkenyl, C$_{5-7}$cycloalkenylC$_{1-6}$alkyl, C$_{5-7}$cycloalkenylC$_{2-6}$alkenyl, C$_{5-7}$cycloalkenylC$_{2-6}$alkynyl, 5- or 6-membered heteroaryl, 5- or 6-membered heteroarylC$_{1-6}$alkyl, phenyl, phenylC$_{1-6}$alkyl, 5- or 6-membered saturated or partially saturated heterocyclyl or 5- or 6-membered saturated or partially saturated heterocyclylC$_{1-6}$alkyl;

$R^3$ is hydrogen or C$_{1-4}$alkyl;

$R^4$ is hydrogen or C$_{1-4}$alkyl;

and N-oxides thereof where chemically possible;

and S-oxides of sulphur containing rings where chemically possible;

and pharmaceutically acceptable salts and in vivo hydrolysable esters and amides thereof;

excluding 4-(2-benzyl-3-hydroxy-4-formylphenoxymethyl)-3-methoxybenzoic acid and 4-(2-(3-phenylprop-2-en-1-yl)-3-hydroxy 4-formyl phenoxymethyl)-3-methoxybenzoic acid.

An 8 to 10 membered bicyclic heteroaryl ring system is a bicyclic aryl ring system having from 8 to 10 ring atoms wherein 1, 2, 3, 4 or 5 of the ring atoms are selected from nitrogen, oxygen and sulphur.

A 5- or 6-membered heteroaryl ring system is a monocyclic aryl ring system having 5 or 6 ring atoms wherein 1, 2 or 3 ring atoms are selected from nitrogen, oxygen and sulphur.

A 5- or 6-membered saturated or partially saturated heterocyclic ring is a ring system having 5 or 6 ring atoms wherein 1, 2 or 3 of the ring atoms are selected from nitrogen, oxygen and sulphur.

Particular 8 to 10 membered bicyclic heteroaryl ring systems include benzofuryl, indolizinyl, isoindolyl, indolyl, indazolyl, benzothienyl, quinolyl, isoquinolyl, quinoxalinyl, quinazolinyl, cinnolinyl and phthalazinyl.

Particular 5- or 6-membered heteroaryl rings include pyrrolyl, imidazolyl, pyrazolyl, isothiazolyl, isoxazolyl, pyridyl, pyrazinyl, pyrimidinyl, pyridazinyl, thiazolyl, thiadiazolyl, thienyl, furyl and oxazolyl.

Particular 5- or 6-membered saturated or partially saturated heterocyclic ring ring systems include pyrrolidinyl, pyrrolinyl, imidazolidinyl, pyrazolidinyl, piperidyl, piperazinyl and morpholinyl.

Particular substituents for ring carbon atoms in A include halo, trifluoromethyl, nitro, hydroxy, amino, C$_{1-4}$alkylamino, diC$_{1-4}$alkylamino, cyano, C$_{1-6}$alkoxy, C$_{1-6}$alkylS(O)$_p$—(p is 0, 1 or 2), phenylS(O)$_p$—(p is 0, 1 or 2), C$_{1-6}$alkyl (optionally substituted by hydroxy, amino, halo, nitro, C$_{1-4}$alkylS(O)$_p$—(p is 0, 1 or 2), C$_{1-4}$alkoxy, phenylS (O)$_p$—(p is 0, 1 or 2) or cyano), carbamoyl, C$_{2-6}$alkenyl, C$_{2-6}$ alkynyl, C$_{3-7}$cycloalkyl, C$_{3-7}$cycloalkylC$_{1-3}$alkyl, C$_{3-7}$ cycloalkylC$_{2-3}$alkenyl, C$_{3-7}$ cycloalkylC$_2$-

3 alkynyl, $C_{1-4}$alkoxycarbonylamino, $C_{1-4}$alkanoylamino, $C_{1-4}$alkanoyl(N-$C_{1-4}$alkyl)amino, $C_{1-4}$alkanesulphonamido, benzenesulphonamido, aminosulphonyl, $C_{1-4}$alkylaminosulphonyl, di($C_{1-4}$alkyl)aminosulphonyl, $C_{1-4}$alkoxycarbonyl, $C_{2-4}$alkanoyloxy, $C_{1-6}$alkanoyl, formyl$C_{1-4}$alkyl, trifluoro$C_{1-3}$alkylsulphonyl, hydroxyimino$C_{1-6}$alkyl, $C_{1-4}$alkoxyimino$C_{1-6}$alkyl, $C_{1-6}$alkylcarbamoylamino, phenyl, $C_{1-4}$alkylcarbamoyl and di($C_{1-4}$alkyl)carbamoyl.

Particular substituents for ring carbon atoms in B include halo, trifluoromethyl, nitro, hydroxy, $C_{1-6}$alkoxy, $C_{1-6}$alkyl, $C_{3-7}$cycloalkyl, $C_{3-7}$cycloalkyl$C_{1-3}$alkyl, amino, $C_{1-4}$alkylamino, di($C_{1-4}$alkyl)amino, cyano, —S(O)p$C_{1-6}$alkyl (p is 0, 1 or 2), carbamoyl, $C_{1-4}$alkylcarbamoyl and di($C_{1-4}$alkyl)carbamoyl.

Particular substituents for D include halo, trifluoromethyl, nitro, hydroxy, amino, $C_{1-4}$alkylamino, di($C_{1-4}$alkyl)amino, cyano, $C_{1-6}$alkoxy, —S(O)$_p$$C_{1-4}$alkyl, —S(O) phenyl (p is 0, 1 or 2), $C_{1-4}$alkanoyl and $C_{1-4}$alkyl optionally substituted by hydroxy, halo, nitro, cyano or amino.

Particular substituents for ring carbon atoms in phenyl, heteroaryl and 5- and 6-membered saturated or partially saturated heterocyclyl groups in $R^{a1}$ and $R^b$ include halo, trifluoromethyl, nitro, hydroxy, amino, $C_{1-4}$alkylamino, di$C_{1-4}$alkylamino, cyano, $C_{1-6}$alkoxy, carboxy, $C_{1-6}$alkylS(O)$_p$— (p is 0, 1 or 2), phenylS(O)$_p$— (p is 0, 1 or 2), $C_{1-6}$alkyl (optionally substituted by hydroxy, amino; halo, nitro, $C_{1-4}$alkylS(O)$_p$— (p is 0, 1 or 2), $C_{1-4}$alkoxy, phenylS(O)$_p$— (p is 0, 1 or 2) or cyano), carbamoyl, $C_{2-6}$alkenyl, $C_{2-6}$alkynyl, $C_{3-7}$cycloalkyl, $C_{3-7}$cycloalkyl$C_{1-3}$alkyl, $C_{3-7}$cycloalkyl$C_{2-3}$alkenyl, $C_{3-7}$cycloalkyl$C_{2-3}$alkynyl, $C_{1-4}$alkoxycarbonylamino, $C_{1-4}$alkanoylamino, $C_{1-4}$alkanoyl(N-$C_{1-4}$alkyl)amino, $C_{1-4}$alkanesulphonamido, benzenesulphonamido, aminosulphonyl, $C_{1-4}$alkylaminosulphonyl, di($C_{1-4}$alkyl)aminosulphonyl, $C_{1-4}$alkoxycarbonyl, $C_{2-4}$alkanoyloxy, $C_{1-6}$alkanoyl, formyl$C_{1-4}$alkyl, trifluoro$C_{1-3}$alkylsulphonyl, hydroxyimino$C_{1-6}$alkyl, $C_{1-4}$alkoxyimino$C_{1-6}$alkyl, $C_{1-6}$alkylcarbamoylamino, phenyl, $C_{1-4}$alkylcarbamoyl and di($C_{1-4}$alkyl)carbamoyl.

Where a ring nitrogen atom in A or B can be substituted without becoming quaternised, it can be unsubstituted or substituted by $C_{1-4}$alkyl.

The term 'alkyl' when used herein includes straight chain and branched chain substituents for example methyl, ethyl, n-propyl, isopropyl, n-butyl and isobutyl. The same convention applies to other radicals, for example hydroxyimino$C_{1-4}$alkyl includes 1-(hydroximino)ethyl and 2-(hydroxyimino)ethyl.

Amino acid residues formed from $R^a$ and $R^{a1}$ together with the amide nitrogen to which they are attached and esters thereof include for example radicals of the formula —NH—CH($R^c$)—COO$R^d$ wherein $R^c$ is hydrogen, $C_{1-6}$alkyl, $C_{2-6}$alkenyl, $C_{2-6}$alkynyl, phenyl, phenyl$C_{1-3}$alkyl, 5- or 6-membered heteroaryl or 5- or 6-membered heteroaryl$C_{1-3}$alkyl and $R^d$ is hydrogen or $C_{1-6}$alkyl, wherein alkyl, alkenyl, alkynyl, phenyl and heteroaryl groups are optionally substituted. Examples of substituents include those mentioned above for ring A; in particular hydroxy.

It will be appreciated that when an alkenyl or alkynyl group is directly linked to the nitrogen of a primary or secondary amine, the double or triple bond may not be in the 1-position. Similarly alkyl groups which are substituted by halo, hydroxy or an amine may not be substituted by these substituents in the 1-position when the alkyl group is directly linked to the nitrogen of a primary or secondary amine.

Examples of $C_{1-6}$alkoxycarbonyl are methoxycarbonyl, ethoxycarbonyl and t-butoxycarbonyl; examples of carboxy$C_{1-3}$alkyl are carboxymethyl, 2-carboxyethyl, 1-carboxyethyl and 3-carboxypropyl; examples of $C_{1-6}$alkoxycarbonyl$C_{1-3}$alkyl are methoxycarbonylmethyl, ethoxycarbonylmethyl and methoxycarbonylethyl; examples of tetrazolyl$C_{1-3}$alkyl are tetrazolylmethyl and 2-tetrazolylethyl; examples of $C_{1-4}$alkoxy are methoxy, ethoxy, propoxy and isopropoxy; examples of $C_{2-6}$alkenyl are vinyl and allyl; examples of $C_{2-6}$alkynyl are ethynyl and propynyl; examples of $C_{3-7}$cycloalkyl are cyclopropyl, cyclobutyl and cyclohexyl; examples of $C_{3-7}$cycloalkyl$C_{1-3}$alkyl are cyclopropylmethyl and cyclohexylmethyl; examples of $C_{3-7}$cycloalkyl$C_{2-3}$alkenyl are cyclopropylethenyl and cyclopentylpropenyl; examples of $C_{3-7}$cycloalkyl$C_{2-3}$alkynyl are cyclopropylethynyl and cyclopentylethynyl; examples of $C_{5-7}$alkenyl are cyclopentenyl and cyclohexenyl; examples of $C_{5-7}$cycloalkenyl$C_{1-3}$alkyl are cyclopentenylmethyl and cyclohexenylmethyl; examples of $C_{5-7}$cycloalkenyl$C_{2-3}$alkenyl are cyclohexenylethenyl and cycloheptenylethenyl; examples of $C_{5-7}$cycloalkenyl$C_{2-3}$alkynyl are cyclopentenylethynyl and cyclohexenylethynyl; examples of $C_{1-4}$alkanoyl are formyl, acetyl, propionyl and butyryl; examples of halo are fluoro, chloro, bromo and iodo; examples of $C_{1-4}$alkylamino are methylamino, ethylamino, propylamino and isopropylamino; examples of di($C_{1-4}$alkyl)amino are dimethylamino, diethylamino and ethylmethylamino; examples of —S(O)$_p$$C_{1-4}$alkyl are methylthio, methylsulphinyl and methylsulphonyl; examples of $C_{1-4}$alkylcarbamoyl are methylcarbamoyl and ethylcarbamoyl; examples of di($C_{1-4}$alkyl)carbamoyl are dimethylcarbamoyl, diethylcarbamoyl and ethylmethylcarbamoyl; examples of $C_{1-6}$alkyl are methyl, ethyl, propyl and isopropyl; examples of $C_{1-4}$alkoxycarbonylamino are methoxycarbonylamino and ethoxycarbonylamino; examples of $C_{1-4}$alkanoylamino are acetamido and propionamido; examples of $C_{1-4}$alkanoyl(N-$C_{1-4}$alkyl)amino are N-methylacetamido and N-methylpropionamido; examples of $C_{1-4}$alkanesulphonamido are methanesulphonamido and ethanesulphonamido; examples of $C_{1-4}$alkylaminosulphonyl are methylaminosulphonyl and ethylaminosulphonyl; examples of di($C_{1-4}$alkyl)aminosulphonyl are dimethylaminosulphonyl, diethylaminosulphonyl and ethylmethylaminosulphonyl; examples of $C_{2-4}$alkanoyloxy are acetyloxy and propionyloxy; examples of formyl$C_{1-4}$alkyl are formylmethyl and 2-formylethyl; examples of hydroxyimino$C_{1-6}$alkyl are hydroxyiminomethyl, 1-(hydroxyimino)ethyl and 2-(hydroxyimino)ethyl and examples of $C_{1-4}$alkoxyimino$C_{1-6}$alkyl are methoxyiminomethyl, ethoxyiminomethyl and 2-(methoxyimino)ethyl.

Preferably A is optionally substituted: phenyl, pyridyl, pyrimidyl, pyrazinyl, pyridazinyl, thienyl, 1,2,3-thiadiazolyl, oxazolyl, naphthyl or of the formula:

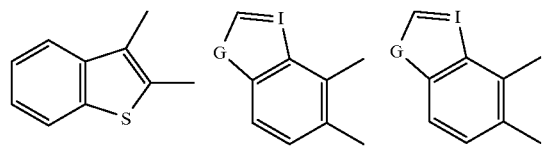

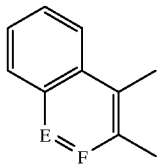

wherein E is nitrogen or CH, F is nitrogen or CH, G is sulphur or oxygen and I is nitrogen or CH.

Preferably B is optionally substituted: phenyl, pyridyl, thiazolyl, thienyl, thiadiazolyl, pyrazinyl, pyridazinyl, pyrimidyl, oxazolyl or imidazolyl.

Preferably D is optionally substituted: thienyl or phenyl.

More preferably A is optionally substituted: phenyl, pyridyl, pyrimidyl, pyrazinyl, pyridazinyl, thienyl or 1,2,3-thiadiazolyl.

More preferably B is optionally substituted: phenyl, pyridyl, thiazolyl, thienyl, thiadiazolyl, pyrazinyl, pyridazinyl or pyrimidyl.

More Preferably D is optionally substituted phenyl.

Yet more preferably A is optionally substituted: phenyl, pyridyl, thienyl or pyrimidyl.

Yet more preferably B is optionally substituted: pyridyl, phenyl, thiazolyl, thienyl or pyridazinyl.

Most preferably A is optionally substituted: phenyl or thienyl.

Most preferably B is optionally substituted phenyl, thiazolyl or pyridyl.

In particular A is optionally substituted phenyl.

In particular B is phenyl.

Preferred optional substituents for ring carbon atoms in A, are halo, nitro, trifluoromethyl, cyano, hydroxy, amino, $C_{1-6}$alkoxy, $C_{1-4}$alkanoylamino, $C_{1-4}$alkylS(O)p—, $C_{1-6}$alkyl (optionally substituted by cyano, phenylS(O)p— or $C_{1-4}$alkylS(O)p—), $C_{1-4}$alkanesulphonamido, benzenesulphonamido, $C_{1-6}$alkanoyl, phenyl, $C_{1-4}$alkoxyimino$C_{1-4}$alkyl and hydroxyimino$C_{1-4}$alkyl.

More preferably optional substituents for ring carbon atoms in A include fluoro, chloro, bromo, nitro, trifluoromethyl, cyano, amino, methoxy, methyl, isopropyl, hexyl, methylthio, benzensulphonyl, phenyl, acetyl, formyl, benzenesulphonamido, hydroxyiminomethyl, 1-(hydroxyimino)ethyl, cyanomethyl and benzensulphonylmethyl.

Preferably, when A is a 6-membered ring, it is unsubstituted, or substituted in the 4, 5 or 6-position (when the ring is numbered such that the ring carbon bearing the —OCH($R^3$)— group is in the 1-position and the ring carbon bearing the —X—D group is in the 2-position).

More preferably, when A is a 6-membered ring, A is unsubstituted, or substituted in the 4 or 6-position using the above numbering system. Most preferably, when A is a 6-membered ring, A is unsubstituted, or substituted in the 4-position using the above numbering system.

A preferred optional substituent for ring carbon atoms in B is hydroxy.

Preferably the aryl group in —X—D is unsubstituted or substituted by one or two substituents.

Preferably, optional substituents for the aryl group in —X—D are selected from halo, nitro, hydroxy, cyano, $C_{1-4}$alkyl, amino, $C_{1-4}$alkoxy and carbamoyl.

Most preferably the aryl group in —X—D is unsubstituted.

Preferably A is unsubstituted or substituted by one or two substituents.

Preferably B is unsubstituted or substituted by one substituent.

Preferably $R^1$ is carboxy, tetrazolyl or of the formula —CONHR$^{a1}$ or —CONHSO$_2$R$^b$.

Preferably R$^a$ is optionally substituted: $C_{1-6}$alkyl, tetrazolyl or pyridylC$_{1-3}$alkyl.

Preferably R$^b$ is $C_{1-4}$alkyl (optionally substituted by hydroxy, nitro, amino, cyano, $C_{1-4}$alkylamino, di-$C_{1-4}$alkylamino, $C_{1-4}$alkanoylamino, $C_{1-4}$alkyl-N-$C_{1-4}$alkanoylamino, carbamoyl, $C_{1-4}$alkylcarbamoyl, di-$C_{1-4}$alkanoylcarbamoyl, halo, $C_{1-4}$alkoxy) or optionally substituted: phenylC$_{1-3}$alkyl, pyridylC$_{1-3}$alkyl, phenyl, thienyl, thiadiazolyl, oxazolyl, isoxazolyl, pyrazolyl or 1,1-dioxidotetrahydrothienyl.

Most preferably R$^b$ is $C_{1-4}$alkyl, hydroxyC$_{1-4}$alkyl, $C_{1-4}$alkoxyC$_{1-4}$alkyl, phenyl (optionally substituted by halo, cyano, nitro, carbamoyl, $C_{1-4}$alkylcarbamoyl, di-$C_{1-4}$alkylcarbamoyl, hydroxy, amino, $C_{1-4}$alkanoylamino, N-$C_{1-4}$alkanoyl-N-$C_{1-4}$alkylamino, $C_{1-4}$alkylamino or di-($C_{1-4}$alkyl)amino), benzyl (optionally substituted by halo, cyano, nitro, carbamoyl, $C_{1-4}$alkylcarbamoyl, di-$C_{1-4}$alkylcarbamoyl, hydroxy, amino, $C_{1-4}$alkanoylamino, N-$C_{1-4}$alkanoyl-N-$C_{1-4}$alkylamino, $C_{1-4}$alkylamino or di-($C_{1-4}$alkyl)amino), thiadiazolyl (optionally substituted by $C_{1-4}$alkanoylamino, amino, $C_{1-4}$alkylamino or di-$C_{1-4}$alkylamino), thienyl (optionally substituted by halo or pyridyl), isoxazolyl (optionally substituted by $C_{1-4}$alkyl or halo), pyrazolyl (optionally substituted by $C_{1-4}$alkyl or halo) or 1,1-dioxidotetrahydro-2-thienyl.

More preferably $R^1$ is carboxy or tetrazolyl or $R^1$ is of the formula —CONHR$^{a1}$ wherein R$^{a1}$ is tetrazolyl, pyridylC$_{1-3}$alkyl or $C_{1-6}$alkyl (optionally substituted by hydroxy, amino, cyano or $C_{2-4}$alkanoyloxy), or $R^1$ is of the formula —CONHSO$_2$R$^b$ wherein R$^b$ is $C_{1-6}$alkyl or phenyl (wherein the alkyl and the phenyl group are optionally substituted by hydroxy, halo, cyano, $C_{1-4}$alkyl, nitro, amino, carbamoyl, $C_{1-4}$alkoxy, or $C_{1-4}$alkylS(O)p—(p is 0, 1 or 2)).

Most preferably, $R^1$ is carboxy, tetrazolyl or of the formula —CONHR$^a$ wherein R$^a$ is tetrazolyl, pyridylmethyl or $C_{1-6}$alkyl (optionally substituted by hydroxy or cyano), or $R^1$ is of the formula —CONHSO$_2$R$^b$ wherein R$^b$ is $C_{1-6}$alkyl or phenyl (wherein the alkyl and phenyl group are optionally substituted by hydroxy, halo, cyano or $C_{1-4}$alkyl).

In a particular aspect $R^1$ is carboxy, carboxyC$_{1-3}$alkyl, tetrazolyl, tetrazolylC$_{1-3}$alkyl, tetronic acid, hydroxamic acid, sulphonic acid, or $R^1$ is of the formula —CONR$^a$ R$^{a1}$ wherein R$^a$ is hydrogen or $C_{1-6}$alkyl and R$^{a1}$ is hydrogen, $C_{1-6}$alkyl (optionally substituted by halo, hydroxy, nitro, cyano, trifluoromethyl, $C_{1-4}$alkoxy or $C_{1-4}$alkoxycarbonyl), $C_{2-6}$alkenyl, $C_{2-6}$alkynyl, $C_{1-3}$alkyl substituted by a 5- or 6-membered saturated or partially saturated heterocyclic ring, 5- or 6-membered heteroaryl $C_{1-3}$alkyl, 5- or 6-membered saturated or partially saturated heterocyclic ring, or 5- or 6-membered heteroaryl or $R^1$ is of the formula —CONHSO$_2$R$^b$ wherein R$^b$ is hydrogen, $C_{1-6}$alkyl (optionally substituted by halo, hydroxy, nitro, cyano, trifluoromethyl, $C_{1-4}$alkoxy or $C_{1-4}$alkoxycarbonyl), $C_{2-6}$alkenyl, $C_{2-6}$alkynyl, $C_{1-3}$alkyl substituted by a 5- or 6-membered saturated or partially saturated heterocyclic ring, 5- or 6-membered heteroarylC$_{1-3}$alkyl phenylC$_{1-3}$alkyl, 5- or 6-membered saturated or partially saturated heterocyclic ring, 5- or 6-membered heteroaryl or phenyl; wherein any saturated or partially saturated heterocyclic ring or heteroaryl group in R$^{a1}$ is optionally substituted by halo, hydroxy, nitro, cyano, trifluoromethyl, $C_{1-4}$alkoxy or $C_{1-4}$alkoxycarbonyl and any phenyl, saturated or partially saturated heterocyclic ring and heteroaryl group in R$^b$ is optionally substituted.

Preferably X is of the formula —CR⁴=CR⁴— or —CH(R⁴)—CH(R⁴)—.

Most preferably X is of the formula —CH=CH— or —CH₂—CH₂—.

In particular X is of the formula —CH₂—CH₂—.
Preferably R³ is hydrogen or methyl.
Most preferably R³ is hydrogen.
Preferably R⁴ is hydrogen or methyl.
Most preferably R⁴ is hydrogen.

A preferred class of compounds is that of the formula (V):

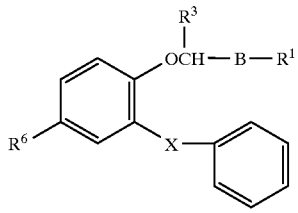

(V)

wherein
R¹ and R³ are as hereinabove defined, R⁶ is hydrogen, halo, trifluoromethyl, nitro, hydroxy, amino, cyano, C₁₋₆alkoxy, C₁₋₆alkylS(O)_p (p is 0, 1 or 2), phenylS(O)_p (p is 0, 1 or 2), C₁₋₆alkyl (optionally substituted by hydroxy, amino, halo, nitro or cyano), C₃₋₇cycloalkyl, C₃₋₇cycloalkylC₁₋₃alkyl, carbamoyl, C₁₋₄alkylcarbamoyl, di(C₁₋₄alkyl)carbamoyl, C₂₋₆alkenyl, C₂₋₆alkynyl, C₁₋₄alkoxycarbonylamino, C₁₋₄alkanoylamino, C₁₋₄alkanoyl(N-C₁₋₄alkyl)-amino, C₁₋₄alkanesulphonamido, benzenesulphonamido, aminosulphonyl, C₁₋₄alkylaminosulphonyl, di(C₁₋₄alkyl)aminosulphonyl, C₁₋₄alkoxycarbonyl, C₂₋₄alkanoyloxy, C₁₋₆alkanoyl, formylC₁₋₄alkyl, trifluoroC₁₋₃alkylsulphonyl, hydroxyiminoC₁₋₆alkyl, C₁₋₄alkoxyiminoC₁₋₆alkyl or C₁₋₆alkylcarbamoylamino, X is —(CH₂)₂— or —CH=CH— and B is phenyl, thiadiazolyl or pyridyl.

Particular compounds of the present invention are:
4-[6-bromo-2-(phenethyl)phenoxymethyl]benzoic acid;
4-[5-nitro-2-(phenethyl)phenoxymethyl]benzoic acid;
4-[4-chloro-6-methyl-2-(phenethyl)phenoxymethyl]benzoic acid;
4-[5-bromo-6-cyano-2-(phenethyl)phenoxymethyl]benzoic acid;
4-[5-chloro-2-(phenethyl)phenoxymethyl]benzoic acid;
4-[4-cyanomethyl-2-(phenethyl)phenoxymethyl]benzoic acid;
4-[2-(phenethyl)phenoxymethyl]benzoic acid;
4-[6-bromo-2-(phenethyl)phenoxymethyl]-2-hydroxybenzoic acid;
4-[5-methyl-2-(phenethyl)phenoxymethyl]benzoic acid;
4-[2-(phenethyl)-6-phenylphenoxymethyl]benzoic acid;
4-[6-amino-2-(phenethyl)phenoxymethyl]benzoic acid;
4-[6-methanethio-2-(phenethyl)phenoxymethyl]benzoic acid;
4-[4-(1-(hydroxyimino)ethyl)-2-(phenethyl)phenoxymethyl]benzoic acid;
4-[4-methyl-2-(phenethyl)phenoxymethyl]benzoic acid;
4-[4-bromo-2-(phenethyl)phenoxymethyl]benzoic acid;
4-[4-methoxy-2-(phenethyl)phenoxymethyl]benzoic acid;
4-[6-cyano-2-(phenethyl)phenoxymethyl]benzoic acid;
4-[6-cyano-4-methyl-2-(phenethyl)phenoxymethyl]benzoic acid;
4-[4-chloro-2-(phenethyl)phenoxymethyl]benzoic acid;
4-[6-benzenesulphonylmethyl-2-(phenethyl)phenoxymethyl]benzoic acid;
4-[4-methanethio-2-(phenethyl)phenoxymethyl]benzoic acid;
4-[5-bromo-2-(phenethyl)phenoxymethyl]benzoic acid;
4-[6-isopropyl-2-(phenethyl)phenoxymethyl]benzoic acid;
5-[4-(2-(phenethyl)-6-phenylphenoxymethyl)phenyl]tetrazole;
5-[4-(4-hydroxy-2-(phenethyl)phenoxymethyl)phenyl]tetrazole;
5-[4-(4-methoxy-2-(phenethyl)phenoxymethyl)phenyl]tetrazole;
5-[4-(2-(phenethyl) phenoxymethyl)phenyl]tetrazole;
5-[4-(4-chloro-2-(phenethyl)phenoxymethyl)phenyl]tetrazole;
5-[4-(4-bromo-2-(phenethyl)phenoxymethyl)phenyl]tetrazole;
5-[4-(6-bromo-2-(phenethyl)phenoxymethyl)phenyl]tetrazole; and
5-[4-(6-isopropyl-2-(phenethyl)phenoxymethyl)phenyl]tetrazole and pharmaceutically acceptable salts and in vivo hydrolysable esters and amides thereof.

It is to be understood that, insofar as certain of the compounds of formula (I) defined above may exist in optically active or racemic forms, by virtue of the compounds of the formula (I) containing an asymmetric carbon atom, the invention includes in its definition of active ingredient any such optically active or racemic form which possesses anti-hyperalgesic properties. The synthesis of optically active forms may be carried out by standard techniques of organic chemistry well known in the art, for example by synthesis from optically active starting materials or by resolution of a racemic form. Similarly, the pain relieving effects may be evaluated using the standard laboratory techniques referred to hereinafter.

An in vivo hydrolysable ester of a compound of the formula (I) containing carboxy group is, for example, a pharmaceutically acceptable ester which is hydrolysed in the human or animal body to produce the parent acid, for example, a pharmaceutically acceptable ester formed with a (1-6C)alcohol such as methanol, ethanol, ethylene glycol, propanol or butanol, or with a phenol or benzyl alcohol such as phenol or benzyl alcohol or a substituted phenol or benzyl alcohol wherein the substituent is, for example, a halo (such as fluoro or chloro), (1–4 C) alkyl (such as methyl) or (1-4C)alkoxy (such as methoxy) group.

A suitable value for an in vivo hydrolysable amide of a compound of the formula I containing a carboxy group is, for example, a N-(1-6C)alkyl or N,N-di-(1-6C)alkyl amide such as N-methyl, N-ethyl, N-propyl, N,N-dimethyl, N-ethyl-N-methyl or N,N-diethyl amide.

A suitable pharmaceutically-acceptable salt of a compound of the formula (I) is, for example, an acid-addition salt of a compound of the formula (I) which is sufficiently basic, for example an acid-addition salt with an inorganic or organic acid such as hydrochloric, hydrobromic, sulphuric, trifluoroacetic, citric or maleic acid; or, for example a salt of a compound of the formula (I) which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl) amine. In a further aspect the invention provides a process for preparing compounds of the formula (I) or pharmaceutically acceptable salts or in vivo hydrolysable amides or ester thereof, which comprises deprotecting a compound of the formula (VI):

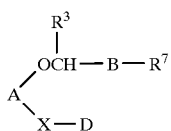

wherein $R^7$ is $R^1$ or protected $R^1$; and $R^3$, X, A, B and D are as hereinabove defined, and any optional substituents are optionally protected and at least one protecting group is present; and thereafter if necessary:

i) forming a pharmaceutically acceptable salt; and/or
ii) forming an in vivo hydrolysable ester or amide;

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

A suitable protecting group for a hydroxy group is, for example, an arylmethyl group (especially benzyl), a tri-(1-4C)alkylsilyl group (especially trimethylsilyl or tert-butyldimethylsilyl), an aryldi-(1-4C)alkylsilyl group (especially dimethylphenyisilyl), a diaryl-(1-4C)alkylsilyl group (especially tert-butyl-diphenylsilyl), a (1-4C)alkyl group (especially methyl), a (2-4C)alkenyl group (especially allyl), a (1-4C)alkoxymethyl group (especially methoxymethyl) or a tetrahydropyranyl group (especially tetrahydroyran-2-yl). The deprotection conditions for the above protecting groups will necessarily vary with the choice of protecting group. Thus, for example, an arylmethyl group such as a benzyl group may be removed, for example, by hydrogenation over a catalyst such as palladium-on-charcoal. Alternatively a trialkylsilyl or an aryldialkylsilyl group such as a tert-butyldimethylsilyl or a dimethylphenylsilyl group may be removed, for example, by treatment with a suitable acid such as hydrochloric, sulphuric, phosphoric or trifluoroacetic acid, or with an alkali metal or ammonium fluoride such as sodium fluoride or, preferably, tetrabutylammonium fluoride. Alternatively an alkyl group may be removed, for example, by treatment with an alkali metal (1–4 C)alkylsulphide such as sodium thioethoxide or, for example, by treatment with an alkali metal diarylphosphide such as lithium diphenylphosphide or, for example, by treatment with a boron or aluminium trihalide such as boron tribromide. Alternatively a (1–4 C)alkoxymethyl group or tetrahydropyranyl group may be removed, for example, by treatment with a suitable acid such as hydrochloric or trifluoroacetic acid.

Alternatively a suitable protecting group for a hydroxy group is, for example, an acyl group, for example a (2–4 C)alkanoyl group (especially acetyl) or an aroyl group (especially benzoyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide.

A suitable protecting group for an amino, imino or alkylamino group is, for example, an acyl group, for example a (2–4 C)alkanoyl group (especially acetyl), a (1–4 C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl, alkoxycarbonyl or aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid, and an arylmethoxycarbonyl group such as a benzyloxycarbonyl group may be removed, for example, by hydrogenation over a catalyst such as palladium-on-charcoal.

A suitable protecting group for a carboxy group is, for example, an esterifying group, for example a (1–4 C)alkyl group (especially methyl or ethyl) which may be removed, for example, by hydrolysis with a suitable base such as an alkali metal hydroxide, for example lithium or sodium hydroxide; or, for example, a tert-butyl group which may be removed, for example, by treatment with a suitable acid such as hydrochloric, sulphuric or phosphoric acid or trifluoroacetic acid.

In another aspect the compounds of the formula (I) or (VI) may be prepared:

a) from a compound of the formula (VII):

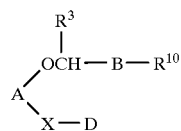

(VII)

wherein A, B, D, $R^3$ and X are as hereinabove defined and $R^{10}$ is a precursor of $R^7$;

b) when X is —(CHR$^4$)$_n$— and n is 2 or 3, by reducing a compound of the formula (VIII):

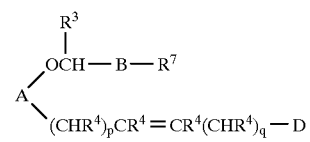

(VIII)

wherein A, B, D, $R^3$, $R^4$, $R^7$, p and q are as hereinabove defined;

c) by reacting a compound of the formula (IX) with a compound of the formula (X):

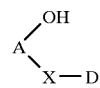

(IX)

$$L—CH(R^3)—B—R^7$$

(X)

wherein A, B, D, $R^3$, X and $R^7$ are as hereinabove defined and L is a leaving group;

d) when A is a activated heteroaryl ring, by reacting a compound of the formula (XI) with a compound of the formula (XII):

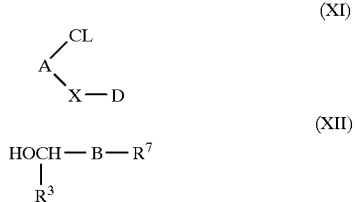

wherein A, B, D, X and $R^7$ are as hereinabove defined; and thereafter if necessary:
i) removing any protecting groups;
ii) forming a pharmaceutically acceptable salt; and/or
iii) forming an in vivo hydrolysable ester or amide;
Particular values for $R^{10}$ include cyano, carbamoyl, alkoxycarbonyl, carboxy and activated carboxy groups such as acid chlorides and activated esters.

The cyano group may be converted into a tetrazole ring by reacting, for example, with ammonium or tin azide in an aprotic solvent such as DMF, in a temperature range of 100° C. to 130° C. For further information on tetrazole synthesis see S. J. Wittenberger and B. J Donner JOC, 1993, 58, 4139–4141; BE Huff et al, Tet. Lett, 1993, 50, 8011–8014; and J. V. Duncia et al, JOC 1991, 56, 2395–2400.

Alkoxycarbonyl may be converted into a carboxy group by acid or base hydrolysis. For example, base hydrolysis may be carried out in an organic solvent such as methanol or THF in a temperature range of ambient to 100° C., in the presence of sodium hydroxide or potassium hydroxide.

Acid hydrolysis may, for example, be carried out or in neat formic acid or neat trifluoroacetic acid optionally in an organic solvent such as dichloromethane.

An alkoxycarbonyl or an activated carboxy group, such as an acid chloride or activated ester, or an acyl group such as an alkanoyl group may be converted to an amide group by reacting with the appropriate amine in an inert solvent such as DMF or dichloromethane, in a temperature range of 0° C. to 150° C., preferably around ambient temperature, in the presence of a base such as triethylamine.

The compounds of the formula (VII) may be prepared using processes b), c), d) or e) from the appropriate starting materials wherein $R^7$ is replaced with $R^{10}$.

The compounds of the formula (VIII) may be reduced under standard conditions known in the art for the reduction of olefins, for example, catalytic hydrogenation using Raney nickel, platinum metal or its oxide, rhodium, zinc oxide, palladium-on-charcoal or Wilkinson's catalyst [RhCl $(Ph_3P)_3$ as the catalyst.

Catalyst hydrogenation is conveniently carried out in the temperature range 0° C. to 150° C., but preferably at ambient temperature at slightly above atmospheric pressure, unless the double bond is highly substituted in which case higher temperatures and pressure may be required, or Wilkinson's catalyst in which case a temperature of approximately 50° C. and pressure of approximately 50 atmospheres are preferable.

Scheme I

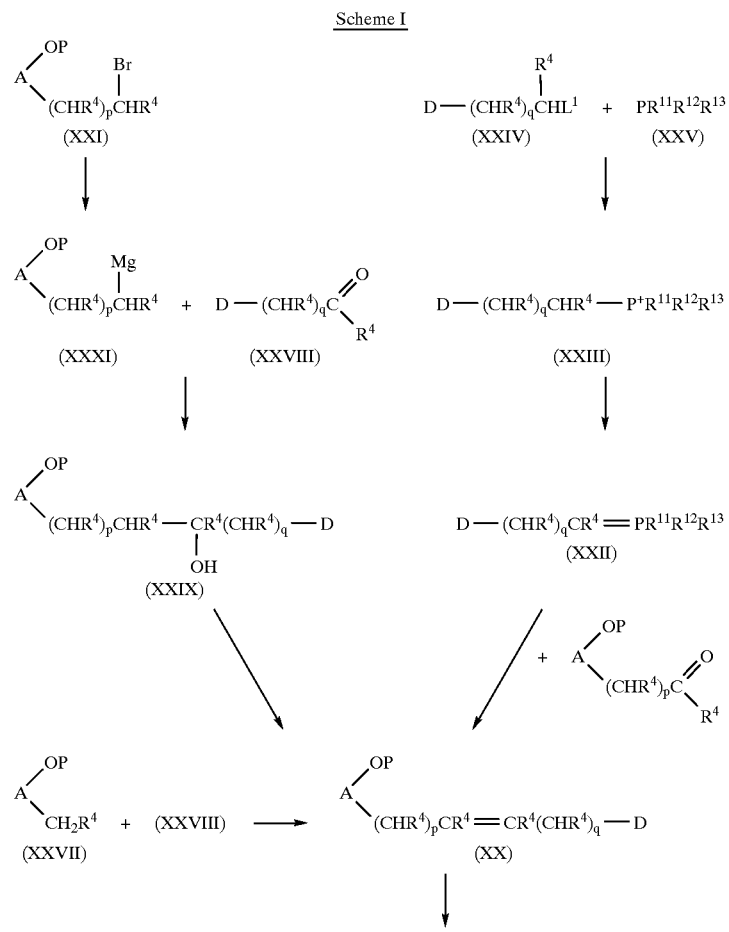

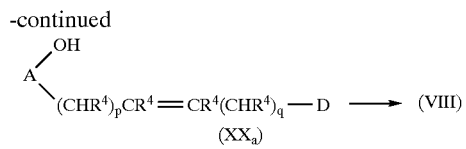
wherein A, D, R⁴, p and q are as hereinabove defined, R$^{11}$–R$^{13}$ are independently alkyl or aryl (such as phenyl or substituted phenyl) L$^1$ is a leaving group and P is a hydroxy protecting group.
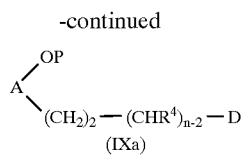
wherein P, A, D, R⁴ and q are as hereinabove defined, and n is 2 or 3 and R$^{15}$ is bromo or iodo.
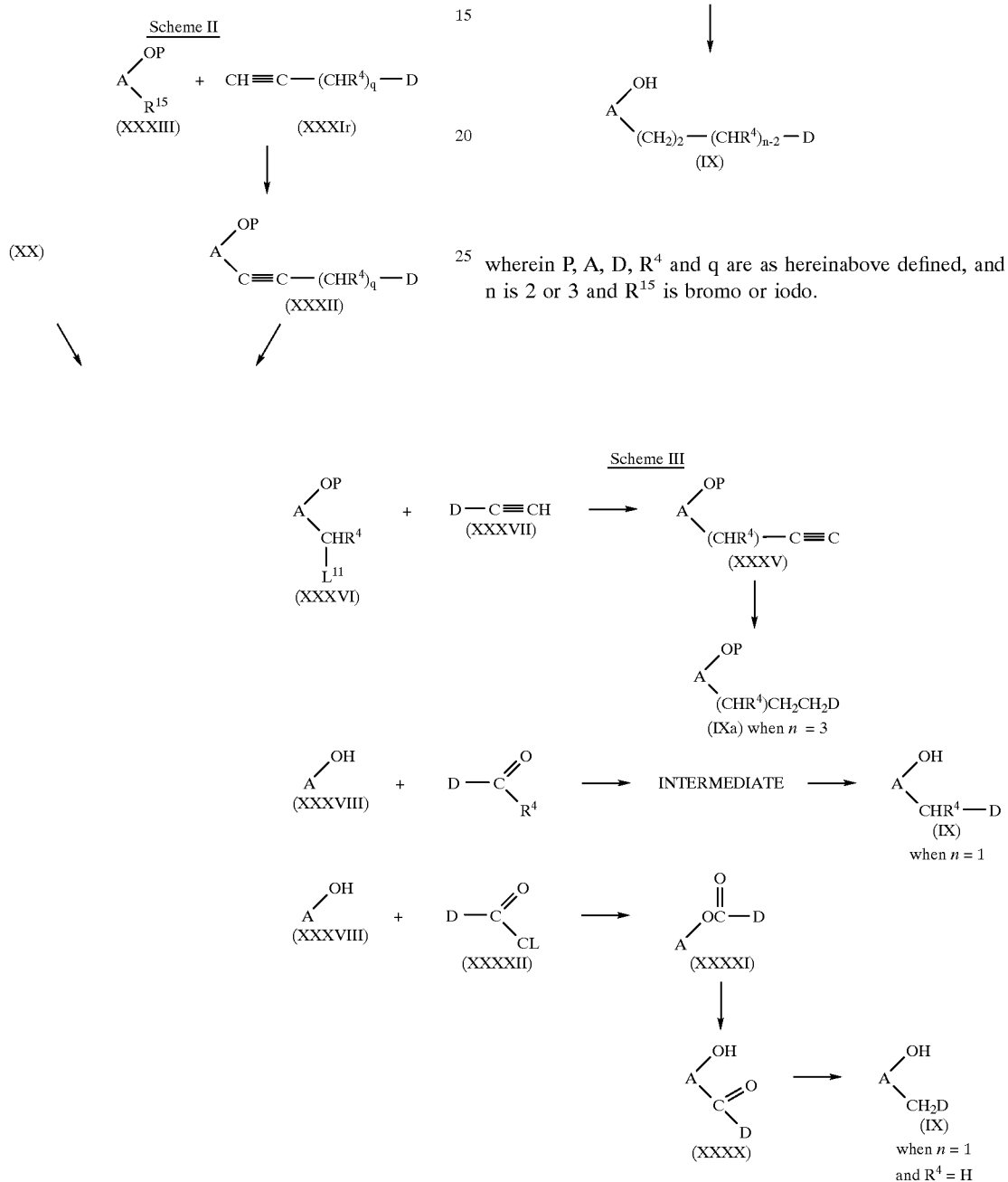

wherein A, D, and $R^4$ are as hereinabove defined and $L^{11}$ is a leaving group.

The compounds of the formula (XX) may be converted to compounds of the formula (VIII) by removing the hydroxy protecting group thus forming a compound of the formula (XXa), and reacting the compound of the formula (XXa) with a compound of the formula (X) in an ether forming reaction. Suitable conditions in the ether forming step are similar to those described for the reaction between compounds of the formulae (IX) and (X) below.

The compounds of the formula (XX) are conveniently prepared by reacting a compound of the formula (XXI) with a compound of the formula (XXII) (Scheme I) under conditions known for the Wittig reaction. For example in an inert solvent such as hexane, tetrahydrofuran, or diethyl ether in a temperature range of −78° C. to ambient. Preferably $R^{11}$, $R^{12}$ and $R^{13}$ are all the same. In particular $R^{11}$–$R^{13}$ are all phenyl.

The compounds of the formula (XXII) are rarely isolatable and usually prepared in situ by deprotonating a compound of the formula (XXIII). Deprotonation is usually carried out in an inert solvent such as tetrahydrofruan or diethyl ether, in a temperature range of −78° C. to ambient, in the presence of a strong base. Examples of strong bases are lithium hexamethyldisilylamide (LiHMS), $CH_3SOCH_2^-$ $Na^+$ and butyl lithium.

A compound of the formula (XXIII) may be prepared by reacting a compound of the formula (XXIV) with a compound of the formula (XXV) (scheme I). Suitable values for $L^1$ include halogen, such as chloro, bromo or iodo. Typically an inert solvent such as acetonitrile, diethyl ether, tetrahydrofuran or toluene is used and a temperature range of 50° C. or 120° C.

Alternatively, the Horner-Emmons reaction may be used in which case the compound of the formula (XXIII) is replaced with the appropriate Horner-Emmons reagent. This can be prepared in an analogous manner to the Wittig reagent from a compound of the formula (XXIV) and a phosphite, for example $PhCH_2P(=O)(OEt)_2$.

The Horner-Emmons reaction is conveniently carried out in an inert solvent such as diethyl ether, THF or toluene, in a temperature range of ambient to 65° C. Examples of bases which may be used in the deprotonation include sodium hydride, butyl lithium and LiHMS.

The compounds of the formula (XXIV) may be known or prepared from another compound of the formula (XXIV) or a compound of the formula (XXVI):

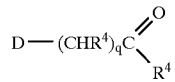

(XXVI)

wherein $R^4$, D, q and optional substituents on D are as hereinabove defined. For example the compound of the formula (XXVI) may be reduced to a compound of the formula (XXIV), wherein $L^1$ is hydroxy. A compound of the formula (XXIV) wherein $L^1$ is hydroxy, may then be converted to a compound of the formula (XXIV) wherein $L^1$ is bromo by, for example, by brominating with phosphorous tribromide.

Alternatively, when p is 0, and in particular when A is a heteroaryl group, compounds of the formula (XX) may be formed by reacting a compound of the formula (XXVII) with a compound of the formula (XXVIII) in the presence of acetic anhydride or a Lewis acid such as titanium tetrachloride or zinc chloride. The reaction is conveniently performed in an inert solvent such as dichloromethane in a temperature range of ambient to 100° C.

Compounds of the formula (XX) may also be prepared by dehydrating a compound of the formula (XXIX) using standard methods known in the art for dehydration. For example with sulphuric or phosphoric acid at an elevated temperature or aluminium oxide at an elevated temperature.

Compounds of the formula (XXIX) may be prepared by reacting a compound of the formula (XXX) and a compound of the formula (XXVIII) in a Grignard reaction. The compound of the formula (XXX) may be formed by reacting a compound of the formula (XXXI) with magnesium, in an etherial solvent such as diethyl ether optionally with warming to initiate the reaction. The compound of the formula (XXX) may be reacted, in situ, with the compound of the formula (XXVIII) in a temperature range of −78° C. to reflux.

Alternatively compounds of the formula (XXIX) may be prepared by deprotonating a compound of the formula (XXVII) with a base and reacting with a compound of the formula (XXVIII). When A is not electron-withdrawing, for example when A is phenyl, a strong base may be necessary, for example tert-butyl lithium. The reaction is conveniently carried out in an etherial solvent such as tetrahydrofuran or diethyl ether or, depending on the nature of the base, hexane, in a temperature range of −78° C. to ambient.

The ether forming reaction between compounds of the formulae (IX) and (X) is typically performed in an inert solvent such as acetone or DMF, in a temperature range of ambient to 60° C., in the presence of a mild base. Suitable values for L include tosylate, mesylate, triflate and halo, for example chloro or bromo. When L is bromo, compounds of the formulae (IX) and (X) may, for example, be reacted together in DMF, at ambient temperature in the presence of a base such as potassium carbonate. When L is hydroxy, the Mitsunobu reaction may be used (O. Synthesis, 1981, 1). For example reacting in tetrahydrofuran or toluene in the presence of diethyl azodicarboxylate and triphenylphosphine.

The compounds of the formula (IX) and (X) may alternatively be reacted together using a phase transfer system.

Compounds of the formula (IX) may be prepared as indicated in Schemes II and III. For example, by removing P from a compound of the formula (IXa). Compounds of the formula (IXa), when n is 2 or 3, may be prepared by reducing a compound of the formula (XX) using standard methods such as those described for the reduction of compounds of the formula (VIII).

As an alternative example compounds of the formula (IXa) may be prepared by reducing a compound of the formula (XXXII) using standard methods known for the reduction of alkynes to alkanes, such as catalytic hydrogenation using palladium-on-carbon or Wilkinson's catalyst as the catalyst.

Compounds of the formula (XXXII) may be prepared by reacting a compound of the formula (XXXIII) with a compound of the formula (XXXIV), for example in a trialkylamine solvent such as triethylamine or in dimethylformamide (DMF) or in a DMF/trialkylamine mixture, in the presence of a catalyst such as palladium and preferably also in the presence of copper (I) idodide, in a temperature range of ambient to 100° C.

Compounds of the formula (IX), wherein n is 3, may be prepared by deprotecting a compound of the formula (IXa) wherein n is 3.

Compounds of the formula (IXa), wherein n is 3, may be prepared by reducing a compound of the formula (XXXV) as shown in scheme III. Suitable conditions are as described for the reduction of compounds of the formula (XXXII).

Compounds of the formula (XXXV) are conveniently prepared by deprotonating a compound of the formula (XXXVII) with a base, such as butyl lithium, and reacting with a compound of the formula (XXXVI). In particular $L^{11}$ is bromo, chloro, tosylate or mesylate. Most commonly $L^{11}$ is bromo. The reaction is usually carried out in an etherial solvent such as ether or THF in a temperature range of −78° C. to ambient temperature.

Compounds of the formula (IX), wherein n is 1, may be prepared by reacting together compounds of the formulae (XXXVIII) and (XXXIX). The compounds of the formulae (XXXVIII) and (XXXIX) are reacted together in the presence of $PhB(OH)_2$ and trichloroacetic acid ($CCl_3CO_2H$) (or propanoic acid), in an inert hydrocarbon solvent such as toluene, in a temperature range of 60° C. to reflux. The boronic acid complex intermediate thus formed may be isolated and used in the subsequent step without further purification. This intermediate is converted to a compound of the formula (IX) by reacting with aluminium trichloride ($AlCl_3$) and borane-tert-butylamine complex (tert-butyl $NH_2.BH_3$) in an inert solvent, for example a chlorinated hydrocarbon such as dichloromethane, in a temperature range of 0° C. to reflux. C. K. Lau, H. W. R. Williams, S. Tardiff, C. Dufresne, J. Scheigtz, P. C. Belanger, Can. J. Chem., 67, 1384 (1989)).

Alternatively, compounds of the formula (IX), wherein n is 1, may be prepared by reducing a compound of the formula (XXXX). Reaction conditions for the reduction of a carbonyl group to methylene are known in the art, for example the Clemmensen and Wolff-Kischner reactions.

Compounds of the formula (XXXX) are conveniently prepared by the rearrangement of a compound of the formula (XXXXI). The rearrangement is carried out in the presence of aluminium trichloride at elevated temperature, for example 50–150° C., preferably in the absence of solvent.

The compounds of the formula (XXXXI) may be prepared by reacting a compound of the formula (XXXVIII) with a compound of the formula (XXXXII) in the presence of a base such as triethylamine and optionally also in the presence of dimethylaminopyridine (DMAP). Conveniently the reaction is carried out in an etherial solvent such as diethyl ether, in a temperature range of 0° C. to 100° C., preferably at ambient temperature.

The reaction between compounds of the formulae (XI) and (XII) is most suitable when A is an 'activated' heterocycle for example when A is pyridine, pyrimidine, pyrazine or pyridazine and in compounds of the formula (XI) the chloro group is in the 2- or 4-position of the pyridine, 2- or 4-position of the pyrimidine, 2-position of the pyrazine and 3-position of the pyridazine ring. Such ring systems being optionally further substituted.

Typically compounds of the formulae (XI) and (XII) are reacted together in the presence of a base, such as sodium hydride, potassium tert-butoxide and lithium hexamethyldisilylamide. The reaction may, for example be carried out in an etherial solvent such as diethyl ether or tetrahydrofuran in a temperature range of 0° to 60° C.

Compounds of the formula (XI) may be prepared from compounds of the formula (IX), which in one tautomeric form may contain an oxo group. This oxo group may be converted to a chloro group by reacting the compound of the formula (IX) with a chlorinating agent such as sulphonyl chloride, phosphorous trichloride, phosphorous pentachloride or $P(O)Cl_3$. The reaction is often carried out in the absence of a solvent, although N,N-dimethylaniline may be used if acid-sensitive groups are present. Alternatively an inert organic solvent may be used.

The compounds of the formula (X), (XII), (XXI), (XXIV), (XXVII), (XXVIII), (XXXI), (XXXIII), (XXXIV), (XXXVI) and (XXXVIII) are generally known in the art or can be made by methods analogous to or similar to those used in the examples or those known in the art for related compounds.

It is also possible to synthesise certain intermediates and even protected compounds using primarily ring synthesis. Here, reference is made to the compendiums 'The Chemistry of Heterocyclic Compounds' E. C. Taylor and A. Weissberger (published by John Wiley and Sons) and 'Comprehensive Heterocyclic Chemistry', A. R Katritzky and C. W Rees (published by Pergamon Press (Elsevier)).

Optional substituents may be converted into other optional substituents. For example an alkylthio group may be oxidised to an alkylsulphinyl or alkysulphonyl group, a nitro group reduced to an amino group, a hydroxy group alkylated to a methoxy group, or a bromo group converted to an alkylthio group.

Various substituents may be introduced into compounds of the formulae (I) and (III) and intermediates in the preparation of compounds of the formulae (I) and (III), when appropriate, using standard methods known in the art. For example, an acyl group or alkyl group may be introduced into an activated benzene ring using Friedel-Crafts reactions, a formyl group by formylation with titanium tetrachloride and dichloromethyl ethyl ether, a nitro group by nitration with concentrated nitric acid concentrated sulphuric acid and bromination with bromine or tetra(n-butyl) ammonium tribromide.

It will be appreciated that, in certain steps in the reaction sequence to compounds of the formula (I), it will be necessary to protect certain functional groups in intermediates in order to prevent side reactions. Deprotection may be carried out at a convenient stage in the reaction sequence once protection is no longer required.

As stated hereinbefore compounds of the formula (I) are antagonists of the pain enhancing effects of E-type prostaglandins and of value in the relief of mild to moderate pain which, for example, accompanies inflammatory conditions such as rheumatoid arthritis and osteoarthritis. Certain properties of the compounds may be demonstrated using the test procedures set out below:

(a) an in-vitro guinea pig ileum assay which assesses the inhibitory properties of a test compound against $PGE_2$-induced contractions of the ileum; ileum was immersed in oxygenated Krebs solution containing indomethacin (4 $\mu$g/ml) and atropine (1 $\mu$M) and which was maintained at 37° C.; the ileum was subject to a tension of 1 g; a control dose response curve for $PGE_2$-induced contraction of the ileum was obtained; test compound (dissolved in dimethylsulphoxide) was added to the Krebs solution and a dose response curve for the $PGE_2$-induced contraction of the ileum in the presence of the test compound was obtained; the $pA_2$ value for the test compound was calculated;

(b) an in-vivo assay in mice which assesses the inhibitory properties of a test compound against abdominal constriction response induced by the intraperitoneal administration of a noxious agent such as dilute acetic acid or phenylbenzoguinone (hereinafter PBQ) using the procedure disclosed in European Patent Application No. 0218077.

Although the pharmacological properties of the compounds of the formula I vary with structural change as expected, in general activity possessed by compounds of the formula I may be demonstrated at the following concentrations or doses in one or more of the above-mentioned Tests (a) and (b):

Test (a): $pA_2 > 5.3$;

Test (b): $ED_{30}$ in the range, for example, 0.01–100 mg/kg orally.

No overt toxicity or other untoward effects were noted in Test (b) when compounds of the formula I are administered at several multiples of their minimum inhibitory dose.

Prostaglandin receptors and in particular receptors for $PGE_2$ have been tentatively characterised by Kennedy et al. (Advances in Prostaglandin, Thromboxane and Leukotriene Research, 1983, 11, 327). The known $PGE_2$ antagonist SC-19220 blocks the effect of $PGE_2$ on some tissues such as guinea pig ileum or dog fundus but not on other tissues such as the cat trachea or chick ileum. Those tissues which did possess SC-19220 sensitive mediated effects were said to possess $EP_1$ receptors. Based on this compounds of the present invention, possessing activity in Test (a), are $EP_1$ antagonists.

According to a further feature of the invention there is provided a pharmaceutical composition which comprises a compound of the formula (I) or an in-vivo hydrolysable ester thereof or an amide thereof, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel, spray or aqueous or oily solution or suspension; for nasal use, for example a snuff, nasal spray or nasal drops; for vaginal or rectal use, for example a suppository or rectal spray; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a compound of the formula (I) or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition.

According to a further feature of the invention there is provided a compound of the formula (1) or an in-vivo hydrolysable ester or amide or a pharmaceutically-acceptable salt thereof, for use in a method of treatment of the animal (including human) body by therapy.

According to a further feature of the invention there is provided the use of a compound of the formula I, or an in-vivo hydrolysable ester or amide or a pharmaceutically-acceptable salt thereof, in the manufacture of a medicament for use in the relief of pain in the animal (including human) body.

According to a further feature of the invention there is provided a method for the relief of pain in the animal (including human) body in need of such treatment which comprises administering to said body an effective amount of a compound of the formula I, or an in-vivo hydrolysable ester or amide or a pharmaceutically-acceptable salt thereof.

As mentioned above, a compound of the formula (I) is useful in treating the pain which, for example, accompanies inflammatory conditions such as rheumatoid arthritis and osteoarthritis. In using a compound of the formula I for therapeutic or prophylactic purposes it will generally be administered so that a daily dose in the range, for example, 0.1 mg to 75 mg per kg body weight is received, given if required in divided doses. In general lower doses will be administered when a parenteral route is employed. Thus, for example, for intravenous administration, a dose in the range, for example, 0.05 mg to 30 mg per kg body weight will generally be used. Similarly, for administration by inhalation, a dose in the range, for example, 0.05 mg to 25 mg per kg body weight will be used.

Although the compounds of the formula (I) are primarily of value as therapeutic agents for use in warm-blooded animals (including man), they are also useful whenever it is required to antagonise the effects of $PGE_2$ at the $EP_1$ receptor, based on test a). Thus, they are useful as pharmacological standards for use in the development of new biological tests and in the search for new pharmacological agents.

By virtue of their ability to relieve pain, the compounds of the formula I are of value in the treatment of certain inflammatory and non-inflammatory conditions which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam or other analgesics such as paracetamol, tramadol, Codein or in some circumstances morphine. Co-administration of a compound of the formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the formula (I), or an in-vivo hydrolysable ester or amide or pharmaceutically-acceptable salt thereof, in conjunction or admixture with a cyclooxygenase inhibitory non-steroidal anti-inflammatory agent, and a pharmaceutically-acceptable diluent or carrier.

The compounds of the invention may also be used with other anti-inflammatory agents such as an inhibitor of the enzyme 5-lipoxygenase (such as those disclosed in European Patent Applications Nos. 0351194, 0375368, 0375404, 0375452, 037547, 0381375, 0385662, 0385663, 0385679, 0385680).

The compounds of the formula (I) may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compositions of the invention may in addition contain one or more other therapeutic or prophylactic agents known to be of value for the treatment of pain. Thus for example, a known opiate pain-killer (such as dextropropoxyphene, dehydrocodeine or codeine) or an antagonist of other pain or inflammation mediators, such as bradykinin, neurokinin and calcitonin gene related peptides (CGRP), or an alpha$_2$-adrenoceptor agonist, a GABA$_B$ receptor agonist, a calcium channel blocker, a sodium channel blocker, a CCK$_B$ receptor antagonist, or an antagonist or modulator of the action of glutamate at the NMDA receptor may usefully also be present in a pharmaceutical composition of the invention.

The compounds of the present invention may also be administered in bone diseases such as osteoporosis alone or in combination with calcitonin and bisphosphonates and estrogens.

The invention will now be illustrated in the following non-limiting Examples in which, unless otherwise stated:

(i) evaporations were carried out by rotary evaporations in vacuo and work-up procedures were carried out after removal of residual solids by filtration;

(ii) yields are given for illustration only and are not necessarily the maximum attainable;

(iii) the end-products of the formula I have satisfactory microanalysis and their structures were generally confirmed by NMR and mass spectral techniques;

(iv) intermediates were not generally fully characterised and purity was assessed by thin layer chromatographic, infra-red (IR) or NMR analysis;

(v) melting points are uncorrected and were determined using a Mettler SP62 automatic melting point apparatus or an oil-bath apparatus; melting points for the end-products of the formula I were determined after recrystallisation from a conventional organic solvent such as ethanol, methanol, acetone, ether or hexane, alone or in admixture;

(vi) the following abbreviations have been used:

| | |
|---|---|
| DMF | N,N-dimethylformamide; |
| THF | tetrahydrofuran; |
| DMSO | dimethylsulphoxide; |
| AIBN | 2,2'-azobisisobutyronitrile |

EXAMPLE 1

4-[2-(2-Phenethyl)phenoxymethyl]benzoic Acid

A suspension of methyl 4-[2-(2-phenethyl) phenoxymethyl]-benzoate (2.89 g) in ethanol (16 ml) containing aqueous 1N sodium hydroxide solution (16 ml) was stirred at ambient temperature for 16 hours. An additional portion of ethanol was added (10 ml) and stirring was continued for 16 hours. The reaction mixture was concentrated and the solid obtained on addition of ice-water was removed and discarded. The pH of the aqueous filtrate was adjusted to 3 by the addition of aqueous 1N hydrochloric acid. The solid which precipitated was filtered, washed with water (10 ml) and air dried. Crystallisation of this solid from aqueous ethanol gave 4-[2-(2-phenethyl)-phenoxymethyl] benzoic acid, m.p. 122–123° C., (2.45 g; 88%).

EXAMPLE 2

The compounds in Table I were prepared from the appropriate methyl esters using a similar method to that of example 1.

TABLE I

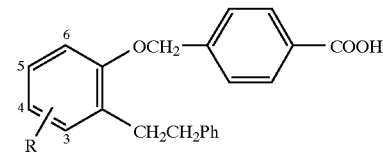

| Compound No. | R | m.p. (°C.) | MS | Footnote |
|---|---|---|---|---|
| 1 | 6-iPr | 110.2–110.8 | CI+: 258 (M + NH4)+ | m |
| 2 | 6-NH$_2$ | 156.4–157.9 | CI+: 348 (M + H)+ | m |
| 3 | 6-OH | 99.3–100.5 | −ve FAB: 347 (M − H)− | m |
| 4 | 6-Br | 138.2–139.2 | +veFAB: 411 (M + H)+ | g |
| 5 | 6-Ph | 141.8–142.0 | CI+: 426 (M + NH4)+ | g |
| 6 | 6-CN | 123.7–125.1 | CI+: 357 (M')+ | c p |
| 7 | 6-hexyl | 67.2–68.6 | EI+: 416 (M')+ | a |
| 8 | 6-C(=N—OH)H | | CI+: 376 (MH)+ | c |
| 9 | 6-SMe | 119.8–120.9 | EI+: 378 (M')+ | c p |
| 10 | 6-SO$_2$Me | 140.9–143.6 | +veFAB: 433 (M + Na)+ | c |
| 11 | 6-SOMe | 52.9–54.1 | CI+: 395 (MH)+ | c |
| 12 | 6-CON(Et)$_2$ | | CI+: 432 (MH)+ | a c |
| 13 | 6-NHSO$_2$Ph | 152.2–152.7 | −veFAB: 486 (M − H)− | c p |
| 14 | 6-N(Et)$_2$ | 90.8–91.7 | +veFAB: 404 (MH)+ | c |
| 15 | 6-COCH$_3$ | 99.1–99.9 | +veFAB: 375 (MH)+ | c |
| 16 | 6-C(=N—OH)CH$_3$ | 61.6–68.7 | −veFAB: 388 (M − H)− | |
| 17 | 6-Br 4-CN | | CI+: 436 (M + H)+ | c |
| 18 | 6-CN, 4-Br | | EI+: 435 (M+) | i |
| 19 | 6-t-Bu, 4-Me | 161–162 | | k p |
| 20 | 6-Br, 4-OCH$_3$ | 117–119 | | b f |
| 21 | 6-CN, 4-OMe | 136–138 | | n |
| 22 | 6-OMe, 4-Me | 112–114 | | g |
| 23 | 4,6,di-t-Bu | 173.8–175.1 | | c |
| 24 | 4-F, 6-Br | 138.4–140 | | c |
| 25 | 4-Cl, 6-Me | 119.9–126.1 | | c |
| 26 | 4,6-di-Br | 150.4–151.5 | | c |
| 27 | 4-Me, 6-CN | 120.5–121.9 | | c |
| 28 | 4-Br | 167–168 | −veFAB: 409, 411 (M − H) | o p |
| 29 | 4-NO$_2$ | 198–199 | CI+: 395 (M + NH4) | n |

TABLE I-continued

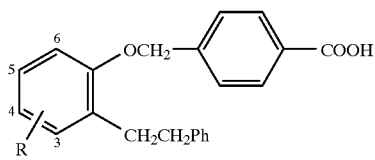

| Compound No. | R | m.p. (°C.) | MS | Footnote |
|---|---|---|---|---|
| 30 | 4-CH₃, 6-Br | 122–123 | −veFAB: 423 (M − H)⁻ | b p |
| 31 | 4,6di-F | 98–100 | +veFAB: 368 (M°)⁺ |  |
| 32 | 4-OCH₃ | 138–140 | +veFAB: 363 (M + H)⁺ | c p |
| 33 | 4-CH₃ | 154–155 | +veFAB: 347 (M + H)⁺ | g p |
| 34 | 4-hexyl | 95–97 | +veFAB: 417 (M + H)⁺ | p q |
| 35 | 4-OH | 175–177 | EI+: 348 (M)⁺ | n p s |
| 36 | 4-C(=NOH)CH₃ | 198–200 | +veFAB: 390 (M + H)⁺ | c |
| 37 | 4-CH₂CN | 152–156 | +veFAB: 372 (M + H)⁺ | k |
| 38 | Not used |  |  |  |
| 39 | 4-COCH₃ | 165–167 | −veFAB: 373 (M − H)⁻ | h |
| 40 | 4-Cl | 166–167 | +veFAB: 366 (M.)⁺ | d |
| 41 | 4-CH₂OH | 168–170 | +veFAB: 262 (M.)⁺ | c |
| 42 | 4-CON(Et)₂ |  | +veFAB: 432 (M + H)⁺ | j |
| 43 | 4-CO₂H |  | −veFAB: 375 (M − H)⁻ | m |
| 44 | 5-Br | 161–162 | +veFAB: 411 (M + H)⁺ | e p |
| 45 | 5-OH | 171–172 | CI+: 349 (M + H)⁺ | k p q u |
| 46 | 4-C(=N—OH)H |  | −veFAB: 374 (M − H)⁻ | c |
| 47 | 4-SMe | 136–138 | +veFAB: 379 (M + H)⁺ | g |
| 48 | 4-SOMe | 178–181 | +veFAB: 395 (M + H)⁺ | c r |
| 49 | 4-SO₂Me |  | −veFAB: 409 (M − H)⁻ | k q |
| 50 | 5-CN | 192–194 | EI+: 357 (M')⁺ | i p |
| 51 | 5-Cl | 160–161 | EI⁺: 384 (M + NH₄)⁺ | e q p |
| 52 | 5-OCH₃ | 170–171 | CI+: 363 (M + H)⁺ | c p |
| 53 | 5-Me | 138–139 | EI⁺: 346 (M°)⁺ | c p |
| 54 | 4-CN | 190–191 | −veFAB: 356 (M − H)⁻ | o p |
| 55 | 6-OCH₃ | 110–111.9 | CI⁺: 380 (M + NH₄)⁺ | c |
| 56 | 6-Cl | 124–125 | −veFAB: 365 (M − H)⁻ | c p |
| 57 | 6-Me | 106–106.5 | −veFAB: 345 (M − H)⁻ | c p |
| 58 | 6-NO₂ | 142–143 | −veFAB: 376 (M − H)⁻ | c p |
| 59 | 4-CH₂SO₂Ph | 193–195 | −veFAB: 485 (M − H)⁻ | g t |

4-[6-Bromo-2-(2-phenethenyl)phenoxymethyl]benzoic acid was also prepared using a similar method to that of example 1, using 2 equivalents of base and precipitating with acetic acid.
MS (CI⁺): 408/410 [M]⁺.

Footnotes
a) Purified by chromatography using methanol/dichloromethane as eluant.
b) Purified by chromatography using diethyl ether/hexane as eluant.
c) 2.0 equivalents of base used.
d) 2.4 equivalents of base used.
e) 2.5 equivalents of base used.
f) 2.65 equivalents of base used.
g) 3.0 equivalents of base used.
h) 3.3 equivalents of base used.
i) 3.6 equivalents of base used.
j) 3.7 equivalents of base used.
k) 4.0 equivalents of base used.
l) 4.35 equivalents of base used.
m) 5.0 equivalents of base used.
n) 7.0 equivalents of base used.
o) 8.0 equivalents of base used.
p) Crystallised from ethanol/water.
q) Extracted with ethyl acetate.
r) Triturated with diethyl ether.
s) Hydroxy group was protected by pivaloyl which fell off in the ester hydrolysis.
t) Precipitated with acetic acid.
u) Methyl ester compound with 5-hydroxy group protected by a pivaloyl group was subjected to hydrolysis in ethanol to give the 5-hydroxy ethyl ester which was subjected to repeated hydrolysis to give the acid.

EXAMPLE 3

4-[2-(2-Phenethyl)-6-(methylsulphinylmethyl)phenoxymethyl]benzoic Acid t-Butyl 4-[2-(2-phenethyl)-6-(methylsulphonyl) phenoxymethyl]-benzoate (0.441 g, 0.95 mMole) was treated with formic acid (3 ml) and the reaction mixture stirred at ambient temperature for 3 hours. The mixture was then diluted with water and the product which precipitated was filtered, washed with water and dried to give 4-[2-(2-phenethyl)-6-(methylsulphinylmethyl)phenoxymethyl] benzoic acid. MS FAB⁻: 407 [M-H]⁻ m.p. 122.5–124.6° C.

EXAMPLE 4

The compounds in Table II were prepared from the appropriate t-butyl ester using a similar method to that of example 3, with variation in conditions noted.

TABLE II

[Structure: phenyl ring with OCH₂-C₆H₄-COOH at position, CH₂CH₂Ph substituent, and R at position 3; positions 4, 5, 6 labeled]

| Compound No. | R | m.p. (° C.) and MS | Conditions | Footnotes |
|---|---|---|---|---|
| 1 | 6-CHO | m.p. 140.4–141.8° C. MS (CI⁺): 360 (M°)⁺ | 0° C.; 0.25 hours dilute with water and filter precipitate. | |
| 2 | 6-CO₂CH₃ | m.p. 132-4-133.0° C. MS (-ve FAB): 389(MH)⁻ | 0° C.; 1.5 hours; 0.4 g of ester 4 ml of acid; precipitate filtered | |
| 3 | 6-CH₂CN | m.p. 120.5–121.6° C. MS (+ve FAB): 372 (M + H)⁺ | Ambient temperature; 1.5 hours; 0.2 g of ester; 2 ml of acid; dilute with water and filter precipitate. | a |
| 4 | 6-CH₂SO₂Ph | m.p. 140.2–142.2° C. MS (CI⁺): 504 (M + NH₄)⁺ | Ambient temperature; 1.5 hours; 0.84 g of ester; 3 ml of acid; 18 hours; dilute with water and filter precipitate | b |
| 5 | 6-CH₂OCH₃ | m.p. 134.7–136.0° C. MS (CI): 394 (M + NH₄)⁺ | Ambient temperature; 3 hours; 0.35 g of ester; 3 ml of acid; filter precipitate | a |
| 6 | 6-CH₂SO₂CH₃ | m.p. 138.1–140.3° C. MS (-ve FAB): 423 (M - H) | Ambient temperature; 16 hours; 0.2 mmol of ester; 2 ml of acid; filter precipitate | |
| 7 | 6-CONHMe | m.p. 147.3–148.9° C. | Ambient temperature; MS (-ve FAB): 388 (M - H)⁻ 18 hours: 0.62 mmol of ester; 2 ml of acid; dilute with water and filter precipitate | |
| 8 | 4-CO₂Me | m.p. 177–179° C. MS (+veFAB): 391 (M + H)⁺ | 30° C.; 4 hours; 1 ml of acid; dilute with ether, filter precipitate and wash with diethyl ether. | |

Footnotes
a Crystallised from ethanol/water
b Triturated with ethyl ether

EXAMPLE 5

5-[4-(4-bromo-2-(2-phenethyl)phenoxymethyl) phenyl]-1H-tetrazole

Sodium azide (1.33 g) was added to a mixture of 4-[4-bromo-2-(2-phenethyl)phenoxymethyl]benzonitrile (2.05 g) and ammonium chloride (1.09 g) in DMF (25 ml) and the mixture was stirred and heated at 125° C. for 40 hours. The cooled reaction mixture was poured into ice-water (100 ml) and the pH of the mixture adjusted to 4–5 with aqueous 2N hydrochloric acid. The solid obtained on filtration was washed with water (50 ml) and air dried. The solid was purified by subjecting to chromatography on silica, eluting with a mixture of methanol and dichloromethane (1:9 v/v) to give 5-[4-(4-bromo-2-(2-phenethyl)phenoxymethyl) phenyl]-1H-tetrazole 1.8 g (78%) m.p. 183–5° C.

EXAMPLE 6

The compounds of Table III were prepared using a similar method to that of example 5.

TABLE III

[Structure: phenyl with OCH₂-C₆H₄-tetrazole, CH₂CH₂Ph, and R substituents]

| Compound No. | R | Equivalents of NH₄Cl and NaN₃ to nitrile | T ° C. | Time (hours) | m.p. (0° C.) and MS | Footnotes |
|---|---|---|---|---|---|---|
| 1 | 4-hexyl | 4 | 130 | 5 | mp 135–137 (+ve FAB): 441 (M + H)⁺ | a |
| 2 | 4-OH | 5 | 130 | 5 | (-ve FAB): 371 (M - H)⁻ | b |

TABLE III-continued

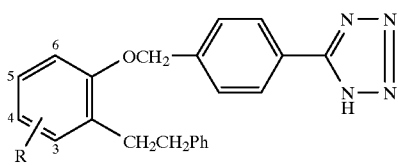

| Compound No. | R | Equivalents of NH₄Cl and NaN₃ to nitrile | T ° C. | Time (hours) | m.p. (0° C.) and MS | Footnotes |
|---|---|---|---|---|---|---|
| 3 | 4-Cl | 4 | 125 | 40 | mp 170–173 (+ve FAB): (M + Na)⁺ | c |
| 4 | 4-OCH₃ | 3.8 | 125 | 48 | mp 126–127 (+ve FAB): 387 (M + H)⁺ | d |
| 5 | 6-iPr | 4 | 125 | 5 | mp 129.4–130.2 | e |
| 6 | 6-Ph | 4 | 120 | 5 | mp 146.5–147.8 | e |
| 7 | 6-Br | 4 | 125 | 5 | mp 113–114.5 | e |
| 8 | 6-hexyl | 4 | 130 | 5 | (+ve FAB): 441 (M + H)⁺ | f |
| 9 | H | — | 125 | 48 | mp 146–8 | h |
| 10 | 5-Cl | — | 150 | 3 | (+ve FAB): 391 (M + H)⁺ | c, g |
| 11 | 5-MeO | — | 125 | 48 | mp 165–7 | b |

Footnotes
a Purified by chromatography eluting with methanol/dichloromethane and triturating the product with hexane.
b Purified by chromatography eluting with methanol/chloroform and triturating with ethyl ether.
c Purified by chromatography eluting with methanol/dichloromethane.
d Purified by extracting with ethyl acetate and subjecting to chromatography eluting with methanol/dichoromethane, then triturating the product with ethyl ether.
e Purified by crystallising from ethanol/water.
f Purified by extracting with ethyl acetate and subjecting to chromatography eluting with methanol/dichloromethane.
g N-Methyl-2-pyrrolidine was used as the solvent.
h Purified by chromatography, eluting with methanol/dichloromethane and recrystallising from ethyl acetate/hexane.

EXAMPLE 7

N-(2-Hydroxyethyl)-4-[2-(2-phenethyl)phenoxymethyl]benzenecarboxamide

A mixture of methyl 4-[2-(2-phenethyl)phenoxymethyl] benzoate (0.5 g) in 2-aminoethanol (6 ml) was heated at 160° C. under argon for 3 hours. Water (10 ml) was added to the cooled reaction mixture which was extracted three times with ethyl acetate (25 ml each time). The combined ethyl acetate extracts were dried (MgSO₄). The residue obtained on removal of the solvent was purified by chromatography on silica, eluting with a mixture of ethyl acetate and dichloromethane (1:1 v/v), and crystallised from a mixture of ethyl acetate and hexane to give N-(2-hydroxyethyl)-4-[2-(2-phenethyl)phenoxymethyl] benzenecarboxamide, (0.23 g; 44%) m.p. 95–7° C.

EXAMPLE 8

The compounds of Table IV were prepared using a similar method to that described in Example 7, except using the appropriate ester in place of methyl 4-[2-(2-phenethyl)phenoxymethyl]benzoate.

TABLE IV

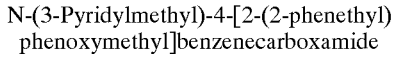

| Compound No. | R | m.p. °C. |
|---|---|---|
| 1 | 5-MeO | waxy solid |
| 2 | 5-Me | 115–7 |
| 3 | 5-Cl | 115–116.5 |
| 4 | 6-MeO | 54–55 |
| 5 | 6-Me | 79.5–81 |

EXAMPLE 9

N-(3-Pyridylmethyl)-4-[2-(2-phenethyl)phenoxymethyl]benzenecarboxamide a) A solution of 4-[2-(2-phenethyl)phenoxymethyl]-benzenecarbonyl chloride (0.4 g) in dichloromethane (2.5 ml) was added to a mixture of triethylamine (0.48 ml) and 3-aminomethylpyridine (0.13 ml) in dichloromethane (5 ml) at 0° C. The reaction mixture was allowed to warm to ambient temperature and was stirred for 16 hours. The reaction mixture was diluted with ethyl acetate (20 ml) and the solution washed consecutively with water (15 ml), saturated aqueous sodium bicarbonate solution (15 ml) and brine (15 ml). The ethyl acetate solution was dried (MgSO$_4$) and the solid obtained on removal of the solvent was purified by subjecting to chromatography on silica, eluting with ethyl acetate, to give N-(3-pyridylmethyl)-4-[2-(2-phenethyl)phenoxymethyl]-benzenecarboxamide (0.23 g; 48%) m.p. 142–4° C.

b) The 4-[2-(2-phenethyl)phenoxymethyl] benzenecarbonyl chloride used as starting material was prepared as follows:

Oxalyl chloride (0.24 ml) was added to a solution of 4-[2-(2-phenethyl)phenoxymethyl]benzoic acid (0.76 g) in dichloromethane (15 ml) containing one drop of DMF maintained at 0° C. The reaction mixture was allowed to warm to ambient temperature and was stirred at this temperature for 3 hours. The reaction mixture was evaporated to dryness to give 4-[2-(2-phenethyl)phenoxymethyl]-benzenecarbonyl chloride as a gum which was used without further purification.

EXAMPLE 10

The compounds of Table V were prepared using a similar method to that described in Example 9, except using the appropriate amine in place of 3-aminomethylpyridine.

TABLE V

| Compound No. | R$^1$ | R | B | M.p. (° C.) and MS | Footnotes |
|---|---|---|---|---|---|
| 1 | H | —CH$_2$-(2-pyridyl) | (1,4-phenylene) | 149–150 | g |
| 2 | 5-MeO | —CH$_2$-(3-pyridyl) | " | 154–5 | g |
| 3 | 5-MeO | —CH$_2$-(2-pyridyl) | " | 101–2 | c |
| 4 | 5-Me | " | " | 114–6 | g |
| 5 | 5-Me | —CH$_2$-(3-pyridyl) | " | 159–160 | g |
| 6 | 5-Cl | —CH$_2$-(2-pyridyl) | " | 128–9 | c |
| 7 | 5-Cl | —CH$_2$-(3-pyridyl) | " | 153–4 | g |
| 8 | 5-MeO | —CH$_2$CH$_2$CH$_3$ | " | 85–6 | i |
| 9 | 4-CH$_3$ | " | " | m.p. 97–99, MS(CI$^+$):388(M + H)$^+$ | a |
| 10 | 4-CH$_3$ | —CH$_2$CH$_2$OH | " | m.p. 112–114 MS(CI$^+$):390(M + H)$^+$ | b |

TABLE V-continued

[Structure: benzene ring with OCH₂—B—CONHR at position with OCH₂ group, CH₂CH₂Ph substituent, and R¹ at position 3]

| Compound No. | R¹ | R | B | M.p. (° C.) and MS | Footnotes |
|---|---|---|---|---|---|
| 11 | 4-CH₃ | —CH₂-(3-pyridyl) | " | m.p. 159–161<br>MS(+veFAB):437(M + H)+ | b |
| 12 | 4-OCH₃ | —CH₂CH₂CH₃ | " | m.p. 99–100<br>MS(CI⁺):404(M + H)⁺ | c |
| 13 | 4-OCH₃ | —CH₂CH₂OH | " | m.p. 107–108<br>MS(CI⁺):406(M + H)⁺ | c |
| 14 | 4-OCH₃ | —CH₂-(3-pyridyl) | " | m.p. 136–138<br>MS(+veFAB):453(M + H)+ | c |
| 15 | 4-CN | —CH₂CH₂CH₃ | " | m.p. 93–95<br>MS(+veFAB):399(M + H)⁺ | c |
| 16 | 4-CN | —CH₂CH₂OH | " | m.p. 113–115° C.<br>MS FAB⁺:401(M + H)⁺ | d |
| 17 | 4-CN | —CH₂-(3-pyridyl) | " | m.p. 139–141° C.<br>MS(+veFAB):448(M + H)⁺ | e |
| 18 | 4-CN | —CH₂-(2-pyridyl) | " | m.p. 93–95<br>MS(+veFAB):399(M + H)⁺ | e |
| 19 | 4-Cl | —CH₂CH₂OH | " | m.p. 114–116<br>MS(+veFAB):410(M + H)⁺ | e |
| 20 | 6-Cl | —CH₂-(3-pyridyl) | " | m.p. 109.6–110.8 | e |
| 21 | 6-NO₂ | —CH₂-(2-pyridyl) | " | m.p. 77.4–78.6 | e |
| 22 | 6-NO₂ | —CH₂-(3-pyridyl) | " | m.p. 103.9–105.2 | e |
| 23 | 6-NO₂ | —CH₂CH₂CH₃ | " | m.p. 75.2–76.1 | f |
| 24 | 6-iPr | —CH₂CH₂OH | " | oil MS(EI⁺):417[M°]⁺ | f |
| 25 | 6-iPr | —CH₂-(3-pyridyl) | " | m.p. 89.5–90.7 | f |
| 26 | 6-CN | —CH₂CH₂OH | " | m.p. 92.1–93.5 | e, f |

TABLE V-continued

[Structure: benzene ring with positions 3,4,5,6 labeled, R¹ at position 3, OCH₂—B—CONHR at position 6, CH₂CH₂Ph at position 2]

| Compound No. | R¹ | R | B | M.p. (° C.) and MS | Footnotes |
|---|---|---|---|---|---|
| 27 | 6-CN | —CH₂-(3-pyridyl) | " | m.p. 136.5–13.7 | e, f |
| 28 | 6-CN | —CH₂CH₂CH₃ | " | m.p. 100.8–101.3 | e, f |
| 29 | 4-CO₂Me | —CH₂CH₂OH | " | m.p. 118–120° C. MS(+veFAB⁺):434(M + H)⁺ | c |
| 30 | 4-Br | " | " | m.p. 120–121 MS(CI⁺)456:(M + H)⁺ | c |
| 31 | 4-Br | —CH₂CH₂CH₃ | " | m.p. 118–119 MS(CI⁺):452(M + H)⁺ | c |
| 32 | 4-Br | —CH₂-(3-pyridyl) | " | m.p. 149–151 MS(CI⁺):501(M + H)⁺ | c |
| 33 | 4-hexyl | —CH₂CH₂OH | " | m.p. 94–96 MS(+veFAB):460(M + H)⁺ | c |
| 34 | 4-NO₂ | —CH₂-(3-pyridyl) | " | m.p. 168–169 MS(+veFAB):468(M + H)⁺ | g, k |
| 35 | 6-Me | —CH₂-(2-pyridyl) | " | m.p. 113.4–114.2 | f, e |
| 36 | 6-Me | —CH₂-(3-pyridyl) | " | m.p. 104.0–104.8 | f, e |
| 37 | 6-Me | —CH₂CH₂CH₃ | " | m.p. 67.8–68.6 | f, e |
| 38 | 6-Me | —CH₂CH₂CN | " | m.p. 111.8–112.5 | f, e |
| 39 | 6-Cl | —CH₂CH₂OH | " | m.p. 76.5–78.1 | e |
| 40 | 6-Cl | —CH₂-(2-pyridyl) | " | m.p. 99.8–100.8 | f |
| 41 | 6-Br | —CH₂CH₂OH | " | m.p. 93.5–95.0 | b |
| 42 | 6-Br | —CH₂-(3-pyridyl) | " | m.p. 105.1–106.0 | b |
| 43 | 6-Br | —CH₂CH₂CH₃ | " | m.p. 104.2–105.0 | |
| 44 | 5-Br | " | " | m.p. 131–132 MS(EI⁺):452(M°)⁺ | b |
| 45 | 5-Br | —CH₂CH₂OH | " | m.p. 123–125 MS(CI⁺):456(M + H) | b |
| 46 | 5-Br | —CH₂-(3-pyridyl) | " | m.p. 152–153 MS(+veFAB):501/503 (M + H )⁺ | b |

TABLE V-continued

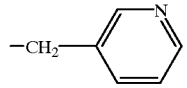

| Compound No. | R¹ | R | B | M.p. (° C.) and MS | Footnotes |
|---|---|---|---|---|---|
| 47 | 5-CN | —CH₂CH₂OH | " | m.p. 142–144<br>MS(CI⁺):401(M − 1H)⁺ | b |
| 48 | 5-CN | —CH₂—(3-pyridyl) | " | m.p. 167–169<br>MS(CI⁺):448(M + H)⁺ | c |
| 49 | 4-Me,6-tBu | " | " | MS(+veFAB):493(M + H)⁺ | c |
| 50 | 4-Me,6-tBu | —CH₂CH₂OH | " | m.p. 81–83 MS(CI⁺):446(M + H)⁺ | c |
| 51 | 4-Me,6-tBu | —CH₂CH₂CH₃ | " | m.p. 91–93 MS(CI⁺):444(M + H)⁺ | c |
| 52 | H | —CH₂CH₂OH | 2,5-pyridyl | m.p. 114–116<br>MS(+veFAB):377(M + H)⁺ | h |
| 53 | H | —CH₂—(3-pyridyl) | " | m.p. 164–166<br>MS(+veFAB):424(M + H)⁺ | h |
| 54 | H | —CH₂CH₂CH₃ | " | m.p. 100–102<br>MS(CI⁺):376(M + H)⁺ | i |
| 55 | 5-OCH₃ | " | " | MS(CI⁺):406(M + H)⁺ | i |
| 56 | 5-OCH₃ | —CH₂—(3-pyridyl) | " | m.p. 150–152<br>MS(CI+):454(M + H)⁺ | h |
| 57 | 5-OCH₃ | —CH₂CH₂OH | " | m.p. 104–108<br>MS(+veFAB):407(M + H)⁺ | h |
| 58 | 4-CN | " | " | MS(+veFAB):402(M + H)⁺ | h |
| 59 | 6-Ph | 1H-tetrazol-5-yl | 1,4-phenylene | m.p. 232.8–234.1<br>MS(+veFAB):498(M + Na)⁺ | f |
| 60 | 6-CN | 1H-tetrazol-5-yl | 1,4-phenylene | m.p. 250.0–250.5<br>MS(+veFAB):425(M + H)⁺ | f, l |

Footnotes
a Purified by chromatography using ethyl acetate/hexane as the eluant and triturating the product with toluene/hexane.
b Purified by chromatography using ethyl acetate/hexane as the eluant and triturating the product with ethyl ether.
c Purified by chromatography using ethyl acetate/hexane as the eluant.
d Purified by chromatography using ethyl acetate/dichloromethane as the eluant.
e Purified by triturating with ethyl ether.
f Purified by chromatography using methanol/dichloromethane as the eluant.
g Purified by chromatography using ethyl acetate as eluant.
h Purified by chromatography using methanol/ethyl acetate as eluant and triturating the product with ethyl ether.
i Purified by chromatography using ethyl acetate/hexane as eluant and triturating the product with ethyl ether/hexane.
j Purified by chromatography using methanol/ethyl acetate as eluant and triturating the product with diethyl ether/ethyl acetate.
k Product triturated with acetone.
l Product triturated with ethyl ether.

EXAMPLE 11

N-(2-Pyridylmethyl)-4-[6-methoxy-2-(phenethyl) phenoxymethyl]benzenecarboxamide Triethylamine (0.24 ml) was added to a solution of 4-(6-methoxy-2-(2-phenethyl)phenoxymethyl)benzoic acid (0.6 g) and 2-aminomethylpyridine (0.20 ml) in DMF (20 ml) maintained at 5° C. Diphenylphosphoryl azide (0.37 ml) was added to this mixture and the solution was allowed to warm to ambient temperature and was stirred at this temperature for 16 hours. Water (50 ml) was added to the reaction mixture. This mixture was extracted with ethyl acetate (2×50 ml) and the ethyl acetate extracts washed with water (50 ml) and dried ($MgSO_4$). The residue obtained on evaporation of the solvent was purified by subjecting to chromatography on silica eluting with a mixture of methanol and dichloromethane (1:49 v/v) to give N-(2-pyridylmethyl)-4-[6-methoxy-2-(2-phenethyl) phenoxymethyl]benzenecarboxamide (0.5 g; 66%) m.p. 126–7° C.

EXAMPLE 12

The compounds of Table VI were prepared using a similar method to that outlined in Example 11, except using the appropriate amine in place of 2-aminomethylpyridine.

TABLE VI

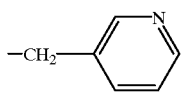

| Compound No. | $R^1$ | R | B | m.p. (° C.) and MS | Footnotes |
|---|---|---|---|---|---|
| 1 | 5-OH | 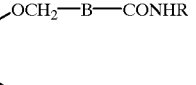 | 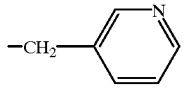 | 185–7 | |
| 2 | 6-MeO | " | " | 74 | |
| 3 | 5-OH | —$CH_2CH_2OH$ | " | waxy solid | |
| 4 | 4-OH | —$CH_2CH_2OH$ | " | m.p. 116–119<br>MS(+veFAB):392(M + H)$^+$ | a |
| 5 | 6-OH | —$CH_2CH_2OH$ | " | m.p. 135.1–136.6 | b |
| 6 | 6-OH | 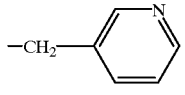 | " | m.p. 123.7–125.8 | b |
| 7 | 6-$CH_2SOCH_3$ | —$CH_2CH_2OH$ | " | Gum<br>MS(CI$^+$):452(M + H)$^+$ | |
| 8 | 6-SMe | " | " | Gum<br>MS(CI$^+$):422(M + H)$^+$ | |
| 9 | 6-$CH_2OCH_3$ | " | " | Gum<br>MS(CI$^+$):420(M + H)$^+$ | |
| 10 | 6-$CH_2SO_2Ph$ | " | " | m.p. 45.6–55.0 | |
| 11 | 6-CN | 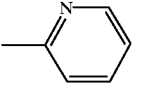 | 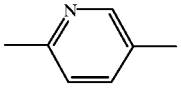 | m.p. 112.8–114<br>MS(+veFAB$^+$):449(M + H)$^+$ | |
| 12 | 6-Br | —$CH_2CH_2OH$ |  | Gum<br>MS(+veFAB$^+$):455/457(M + H)$^+$ | |
| 13 | 5-OH | " | " | m.p. 146–148<br>MS(+veFAB$^+$):393(M + H)$^+$ | |

TABLE VI-continued

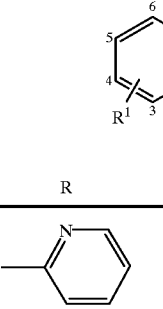

| Compound No. | R¹ | R | B | m.p. (° C.) and MS | Footnotes |
|---|---|---|---|---|---|
| 14 | 5-OH | 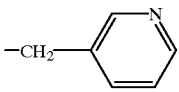 | " | m.p. 186–188 MS(+veFAB⁺):440(M + H)⁺ | |
| 15 | 6-NH$_2$ | 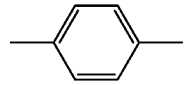 | 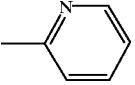 | m.p. 109.7–110.4 MS(CI+):438(M + H)⁺ | c |
| 16 | 6-NH$_2$ | 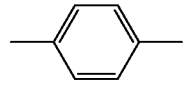 | " | m.p. 87.7–89.0 MS(CI+):438(M + H)⁺ | c |
| 17 | 6-NH$_2$ | —CH$_2$CH$_2$CH$_3$ | | Oil MS(CI+):389(M + H)⁺ | c |
| 18 | 6-NH$_2$ | —CH$_2$CH$_2$OH | " | Gum MS(CI⁺):391(M + H)⁺ | c |

Footnotes
a Purified by chromatography using ethyl acetate/hexane/acetic acid as eluant and triturating the product with ethyl ether.
b Purified by chromatography using methanol/dichloromethane as eluant and triturating the product with ethyl ether.
c Purified by chromatography using methanol/dichloromethane as eluant.

EXAMPLE 13

2-[2-(2-Phenethyl)-6-bromophenoxymethyl]-4-thiazolecarboxylic Acid

A solution of ethyl 2-[2-(2-phenethyl)-6-bromophenoxymethyl]-4-thiazolecarboxylate (1.33 g, 2.98 mmol) in ethanol (10 mL) and THF (10 mL) was treated with 1N NaOH (6 mL). The reaction was stirred at ambient temperature overnight and then partially evaporated and diluted with water. Acetic acid was added to precipitate the title product, which was filtered and dried (1.21 g, 97%).

NMR: (250 MH$_2$,DMSO-d$_6$): δ8.14 (s, 1H), 7.53 (dd, 1H), 7.18 (m, 7H), 5.2 (s, 2H), 2.9 (m, 4H).

Preparation of the starting material:

A solution of ethyl 2-methyl-4-thiazolecarboxylate [JCS 1946, 87, E. R. H. Jones, F. A. Robinson, M. N. Strachan] (5.0 g, 29.2 mmol) in CCl$_4$ (30 ml) was treated with N-bromosuccinimide (5.2 g, 29.2 mmol) and benzoylperoxide (0.03 g). The reaction was heated to reflux while irradiating with a strong lamp for 2½ hours. The reaction mixture was allowed to cool to ambient temperature, filtered and evaporated. The residue was purified by chromatography (eluant: CH$_2$Cl$_2$) to obtain ethyl 2-bromomethyl-4-thiazolecarboxylate (2.27 g, 31%).

NMR (250 MH, DMSO-d$_6$): δ8.55 (s, 1H), 5.04 (s, 2H), 4.30 (g, 2H), 1.32 (t, 3H).

A solution of 6-bromo-2-(2-phenethyl)phenol (1.2 g, 4.33 mmoles) in DMF (5 mL) was treated with K$_2$CO$_3$ (1–2 g, 8.7 mmoles) and ethyl 2-bromomethyl-4-thiazole carboxylate (1.08 g, 4.32 mmoles). The reaction was stirred at ambient temperature overnight and then partitioned between ethyl acetate/H$_2$O. The organic phase was washed well with water, dried over (MgSO$_4$) and evaporated. The residue was purified by chromatography (eluant: CH$_2$Cl$_2$/hexane) to give ethyl 2-[2-(2-phenethyl)-6-bromophenoxymethyl]-4-thiazolecarboxylate (1.425 g, 74%).

NMR (250 MH$_2$, DMSO-d$_6$): δ8.60 (s, 1H), 7.54 (dd, 1H), 7.33 (dd, 1H), 7.18 (m, 6H), 5.27 (s, 2H), 4.34 (f, 2H), 2.9 (m, 4H), 1.33 (t, 3H).

EXAMPLE 14

The compounds of Table VII were prepared using a similar method to that of Example 13.

TABLE VII

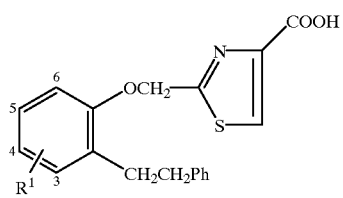

| Compound No. | R[1] | m.p. (° C.) and MS | Footnotes |
|---|---|---|---|
| 1 | 4-OCH$_3$ | m.p. 136–137<br>MS(+veFAB):370(M + H)$^+$ | |
| 2 | 4-Br | m.p. 171–174<br>MS(+veFAB):418(M + H)$^+$ | a |
| 3 | 6-CN | MS(+veFAB)$^+$:365(M + H)$^+$ | b |

Footnotes
a Purified by chromatography using ethyl acetate/acetic acid as eluant.
b Recrystallised from ethanol.

EXAMPLE 15
Preparation of N-(3-pyridylmethyl)-2-[2-(2-phenethyl)-4-methoxyphenoxymethyl]-4-thiazoleamide To a cooled solution (5° C.) of triethylamine (0.24 g, 2.4 mmole) and 3-aminomethylpyridine (0.097 g, 0.89 mmole) in dichloromethane (6 ml) was added a solution of 2-[2-(2-phenethyl)-4-methoxyphenoxymethyl]-4-thiazolylchloride (prepared from compound 1 of Table VII, Example 14, using a similar method to that of the first part of Example 18) (0.8 mmoles) in dichloromethane (5.3 ml). The reaction was allowed to warm to ambient temperature and allowed to stand for 60 hours. The reaction mixture was evaporated. The residue was purified by chromatography (ethyl acetate/hexane) to give the title product (0.205 g, 56%), m.p 113–115° C.

MS (FAB+): 460 (M+H)+.

EXAMPLE 16

The compounds of Table VIII were prepared using a similar method to that of Example 15.

TABLE VIII

| Compound No. | R[1] | R | m.p. (° C.) and MS | Footnotes |
|---|---|---|---|---|
| 1 | not used | | | |
| 2 | 4-OCH$_3$ | —CH$_2$CH$_2$OH | m.p. 129–131° C.<br>MS(CI)$^+$:413(M + H)$^+$ | a |
| 3 | 4-OCH$_3$ | CH$_2$CH$_2$CH$_3$ | m.p. 68–70° C.<br>MS(CI$^+$):411(M + H)$^+$ | a |
| 4 | 4-Br | —CH$_2$-(3-pyridyl) | m.p. 106–108<br>MS(CI$^+$):508(M + H)$^+$ | a |
| 5 | 4-Br | —CH$_2$CH$_2$OH | m.p. 145–147<br>MS(CI$^+$):461(M + H)$^+$ | a |
| 6 | 6-Br | —CH$_2$CH$_2$CH$_3$ | m.p. 81.7–83.0<br>MS(+veFAB):459/461(M + H)$_+$ | b |
| 7 | 6-Br | —CH$_2$CH$_2$OH | Gum<br>MS(CI$^+$):461/463(M + H)$^+$ | c |
| 8 | 6-Br | —CH$_2$-(3-pyridyl) | m.p. 110–110.9<br>MS(CI$^+$):508/510(M + H)$^+$ | c |

Footnotes
a Purified by chromatography using ethyl acetate/hexane as eluant.
b Purified by chromatography by using methanol/dichloromethane as eluant.
c Purified by chromatography using methanol/dichloromethane as eluant and triturating the product with ethyl ether.

EXAMPLE 17

The compounds of Table IX were prepared using a similar method to that of example 13, from the appropriate 2-(2-phenethyl)phenol and ethyl 2-bromomethyl-5-thiazolecarboxylate (Reference Example 18).

TABLE IX

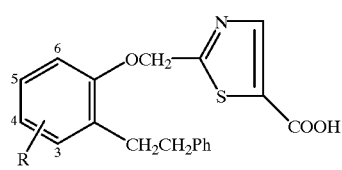

| Compound No. | R | Data | Footnotes |
|---|---|---|---|
| 1 | 4-Me | m.p. 157–160<br>MS(+veFAB):354(M + H)$^+$ | a |
| 2 | 6-Br | m.p. 143.1–145.0<br>MS(+veFAB):418/420(M + H)$^+$ | |

Footnotes
a Purified by chromatography using ethyl acetate/hexane as eluant.

EXAMPLE 18

N-(2-Hydroxyethyl)-2-[2-(2-phenethyl)-6-bromophenoxymethyl]-5-thiazoleamide

A solution of 2-[6-bromo-2-(2-phenethyl)phenoxymethyl]-5-thiazole carboxylic acid (Table IX, Compound 2) (1.029 g, 2.4 mmol) in dichloromethane (10 ml) was treated with oxalyl chloride (0.459 g, 3.6 mmol) and two drops of DMF. The reaction was stirred at ambient temperature for 1 hour. The reaction mixture was evaporated to dryness to give the acid chloride which was then taken up in a measured amount of dry dichloromethane (9 ml).

To a cooled (5° C.) stirred solution of ethanolamine (0.061 g, 1 mmol) and triethylamine (0.101 g, 1 mmol) in dichloromethane (4 ml) was added an aliquot of the acid chloride solution prepared above (0.8 mmol, 3 ml). The reaction was allowed to warm to ambient temperature and stirred overnight. The reaction mixture was evaporated to dryness and the residue purified by chromatography (methanol/CH$_2$Cl$_2$) to give the title amide (0.26 g, 71%) as an off-white solid. m.p. 102.6–104.8° C. MS(CI$^+$): 461/463 (M+H)$^+$.

EXAMPLE 19

The compounds of Table X were prepared using a similar method that of example 18.

TABLE X

| Compound No. | R$^1$ | R | m.p. (° C.) and MS | Footnotes |
|---|---|---|---|---|
| 1 | 4-CH$_3$ | —CH$_2$CH$_2$CH$_3$ | m.p. 106–107<br>MS(+veFAB):395(M + H)$^+$ | a |
| 2 | 4-CH$_3$ | —CH$_2$-pyridyl | m.p. 164–165<br>MS(CI+):444(M + H)$^+$ | b |
| 3 | 6-Br | " | Gum<br>MS(+veFAB):508/510(M + H)$^+$ | c |
| 4 | 6-Br | —CH$_2$CH$_2$CH$_3$ | Gum<br>MS(CI$^+$):459/461(M + H)$^+$ | c |

Footnotes
a Purified by chromatography using ethyl acetate/hexane as eluant.
b Purified by chromatography using ethyl acetate as eluant.
c Purified by chromatography using methanol/dichloromethane as eluant.

EXAMPLE 20

2-(2-(2-Phenethyl)-4-bromophenoxymethyl)-5-pyridinecarboxylic Acid

A solution of methyl 2-(2-(2-phenethyl)-4-bromophenoxymethyl)-5-pyridinecarboxylate (1.82 g, 4.27 mmol) in ethanol (16 ml) and THF (8 ml) was treated with 2N NaOH (5 ml). The reaction mixture was stirred at ambient temperature for 24 hours. The reaction mixture was partially evaporated and diluted with H$_2$O. The pH of the reaction mixture was adjusted to approximately 4–5 with glacial acetic acid. The precipitate was filtered, washed with water and dried. Recrystallization from ethanol/water gave the title compound as a white solid (1.78 g, quantitative) m.p. 197–199° C.

NMR: (200 MH$_2$; DMSO-d$_6$): δ13.4 (bs, 1H), 9.08 (m, 1H), 8.32 (dd, 1H), 7.62 (d, 1H), 7.25 (m, 7H), 6.98 (d, 1H), 5.28 (s, 2H), 2.90 (m, 4H).

The starting material was prepared as follows:

A solution of methyl 2-methyl-5-pyridinecarboxylate (10 g, 66.2 mmoles) in CCl$_4$ (120 ml) was treated with acetic acid (5 ml) followed by N-bromosuccinimide (66 mmol, 11.8 g). The reaction was heated to reflux over a bright lamp and held at reflux for 2 hours. The mixture was filtered and the filtrate washed with H$_2$O (x1), NaHCO$_3$ (x1) and brine (x1). The organic phase was dried (MgSO$_4$) and evaporated to give a residual red oil which was purified by chromatography (eluant: CH$_2$Cl$_2$/hexane) to give 2-bromomethyl-5-pyridinecarboxylate (2.2 g, 14%).

NMR (250 MH$_2$, DMSO-d$_6$): δ9.04 (m, 1H), 8.30 (dd, 1H), 7.70 (dd, 1H), 4.74 (s, 2H), 3.89 (s, 3H).

A solution of the 4-bromo-2-(2-phenethyl)phenol (1.25 g, 14.5 mmol in DMF (10 ml) was treated with K$_2$CO$_3$ (0.82 g, 5.96 mmol) and methyl 2-bromomethyl-5-pyridine carboxylate (1.14 g, 4.96 mmol). The reaction was stirred at ambient temperature and then evaporated in vacuo. The residue was partitioned between ethyl acetate/H$_2$O and the combined organic extracts were washed with at NaCl solution, dried (MgSO$_4$) and evaporated. The residue was purified by chromatography (eluant: ethyl acetate/hexane) to give methyl 2-(2-phenethyl)-4-bromophenoxy methyl)-5-pyridinecarboxylic acid (1.82 g, 95%).

NMR: (200 MH$_2$, DMSO-d$_6$): δ9.1 (d, 1H), 8.36 (dd, 1H), 7.65 (d, 1H), 7.25 (m, 7H), 6.99 (d, 1H), 5.28 (s, 2H), 3.90 (s, 3H), 2.9 (m, 4H).

EXAMPLE 21

The compounds of Table XI were prepared from the appropriate ester and phenol using a similar method to that of example 20.

TABLE XI

| R | m.p. (° C.) | MS | Footnote |
|---|---|---|---|
| 5-OH | 227–228 | (CI$^+$):350(M + H)$^+$ | a |
| 5-H | 184–185 | (CI$^+$):334(M + H)$^+$ | a |
| 5-OMe | 182–184 | (+veFAB):364(M + H)+ | a |
| 4-CN | 192–194 | (CI$^+$):359(M + H)$^+$ | — |
| 6-CN | 146.4–148.8 | (−veFAB):357(M − H)$^−$ | a |
| 6-Br | 136.4–137.5 | (CI$^+$):412/414(M + H)$^+$ | a |

Footnote
a Recrystallised from ethanol/water.

EXAMPLE 22

Preparation of 3-[6-isopropyl-2-(2-phenethyl)phenoxymethyl]benzoic acid

A solution of methyl 3-[6-isopropyl-2-(2-phenethyl)phenoxymethyl]benzoate (2.368 g, 608 mmol) in ethanol (10 ml) was treated with 1N NaOH (13 ml). The reaction stirred at ambient temperature overnight and then partially evaporated and diluted with water. Acetic acid was added to precipitate the product which was filtered, washed with water, and dried to give the title product as a sticky solid (2.01 g, 88%).

NMR (250 MH$_2$; DMSO-d$_6$): δ8.07 (bs, 1H), 7.91 (m, 1H), 7.58 (m, 1H), 7.42 (t, 1H), 7.16 (m, 8H), 4.73 (s, 2H), 3.39 (m, 1H), 2.88 (bs, 4H), 1.19 (d, 6H).

EXAMPLE 23

The compounds of table XII were prepared from the appropriate methyl ester using a similar method to that of example 22.

TABLE XII

| Compound No. | R | M.P. (° C.) and MS | Footnote |
|---|---|---|---|
| 1 | 4-Br | m.p. 162–163; MS(+veFAB):413/411(M + H)$^+$ | a |
| 2 | 4-OCH$_3$ | m.p. 129–130; MS(+veFAB):363(M + H)$^+$ | a |
| 3 | 6-CN | m.p. 119.3–120.5; MS(+veFAB):358(M + H)$^+$ | — |
| 4 | 6-Br | m.p. 88.4–93.1; MS(+veFAB):433/435(M + Na)$^+$ | a |

Footnote
a Recrystallised from ethanol/water.

EXAMPLE 24

Preparation of N-(2-hydroxyethyl)-3-[2-(2-phenethyl)-6-bromophenoxymethyl]benzamide To a cooled solution (5° C.) of ethanolamine (0.06 g, 1 mmole) and triethylamine (0.101 g, 1 mmole) in dichloromethane (10 ml) was added a solution of 3-[2-(2-phenethyl)-6-bromophenoxymethyl]benzoyl chloride [0.79 mmole] in dichloromethane [33 ml)]. The reaction was allowed to warm to ambient temperature over 1 hour. The reaction mixture was evaporated and the residue purified by chromatography (methanol/CH$_2$Cl$_2$) to give the title product as a white solid (0.18 g, 50%), m.p. 82.2–84.2° C. MS (FAB+): 454/456 (M+H)$^+$. 3-[2-(2-phenethyl)-6-bromophenoxymethyl]benzoyl chloride was prepared according to the method described in example 9b).

EXAMPLE 25

The compounds of Table XIII were prepared using a similar method to that of example 24.

TABLE XIII

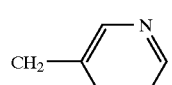

| Compound | R$^1$ | R | m.p. (°C.) MS and elemental analysis (EA) | Footnote |
|---|---|---|---|---|
| 1 | 6-iPr | —CH$_2$CH$_2$OH | MS (+veFAB): 418 (M + H)$^+$<br>EA:<br>found: 76.2% C, 7.7% H, 3.2% N<br>calc: 0.4% H$_2$O: 76.3% C, 7.5% H, 3.3% N. | a |
| 2 | 6-iPr | 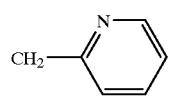 | MS (CI$^+$): 465 (M + H)$^+$<br>Gum | b |
| 3 | 6-iPr | 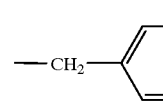 | MS (CI$^+$): 465 (M + H)$^+$<br>Gum | b |
| 4 | 6-iPr | —CH$_2$CH$_2$CH$_3$ | MS (CI$^+$): 416 (M + H)$^+$<br>EA:<br>found: 80.8% C, 8.0% H, 3.5% N<br>calc: 80.9% C, 8.0% H, 3.37% N | b |
| 5 | not used | | | |
| 6 | 6-Br | 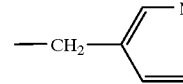 | MS (CI$^+$): 501/503 (M + H)$^+$<br>EA:<br>found: 66.4% C, 4.8% H, 4.9% N<br>calc: 66.4% C, 5.0% H, 5.5% N | b |
| 7 | 6-Br | —CH$_2$CH$_2$CH$_3$ | MS (EI$^+$): 451/453 (M°)$^+$<br>m.p. 76.4–77.2 | b |
| 8 | 6-CN | —CH$_2$CH$_2$OH | MS (CI$^+$): 401 (M + H)$^+$<br>m.p. 102.9–103.6 | a |
| 9 | 6-CN | 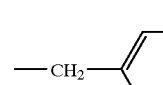 | MS (CI$^+$): 448 (M + H)$^+$<br>m.p. 95.9–98.1 | a |
| 10 | 4-Br | —CH$_2$CH$_2$CH$_3$ | MS (CI$^+$): 452 (M + H)$^+$<br>m.p. 127–129 | c |
| 11 | 4-Br | —CH$_2$CH$_2$OH | MS (CI$^+$): 454 (M + H)$^+$<br>m.p. 110–112 | c |
| 12 | 4-Br | —CH$_2$— (pyridyl) | MS (CI$^+$): 501 (M + H)$^+$<br>m.p. 126–127 | c |
| 13 | 4-OCH$_3$ | —CH$_2$CH$_2$CH$_3$ | MS (CI$^+$): 404 (M + H)$^+$<br>m.p. 95–97 | c |
| 14 | 4-OCH$_3$ | —CH$_2$CH$_2$OH | MS (CI$^+$): 406 (M + H)$^+$<br>m.p. 116–118 | c |

TABLE XIII-continued

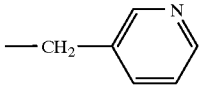

| Compound | R[1] | R | m.p. (°C.) MS and elemental analysis (EA) | Footnote |
|---|---|---|---|---|
| 15 | 4-OCH$_3$ | —CH$_2$—(pyridyl) | MS (CI+): 452 (M + H)$^+$<br>m.p. 91–93 | c |

Footnotes
a Purified by chromatography using methanol/dichloromethane as eluant and triturating the product with ethyl ether.
b Purified by chromatography using methanol/dichloromethate as eluant.
c Purified by chromatography using ethyl acetate/hexane as eluant.

EXAMPLE 26

Not used

EXAMPLE 27

Preparation of 4-(4-carboxy-2-(2-phenethyl)phenoxymethyl)benzoic Acid

To a solution of ethyl $^4$-hydroxy-3-(2-phenethyl)benzoate (1.04 g, 3.85 mmol) in DMF (16 ml) was added K$_2$CO$_3$ (0.94 g, 6.8 mmol) and methyl 4-bromomethylbenzoate (1.25 g, 5.5 mmol). The reaction was stirred at ambient temperature 18 hours, then evaporated at reduced pressure. The residue was partitioned between ethyl acetate and water and the organic phase dried (MgSO$_4$) and evaporated to give methyl 4-(4-ethoxycarbonyl-2-(2-phenethyl)phenoxymethyl)benzoate as a white solid after chromatography (eluant: ethyl ether/hexane) (1.2 g, 75%).

NMR (200 MHz, DMSO-d$_6$): δ8.0 (d, 2H), 7.79 (m, 2H), 7.62 (d, 2H), 7.18 (m, 6H), 5.32 (s, 2H), 4.26 (q, 2H), 3.87 (s, 3H), 2.89 (m 4H), 1.30 (t, 3H).

The above diester (1.2 g, 2.87 mmol) was dissolved in ethanol (10 ml) and THF (10 ml) and 3N NaOH (10 mL) added. The reaction was allowed to stir at ambient temperature for 2 days. The reaction was partially evaporated, diluted with water and acidified to pH4 with dilute HCl. The precipitate was filtered, washed with water, and dried to give the title product (0.66 g, 61%).

NMR (250 MHz, DMSO-d$_6$): δ12.7 (bs, 1H), 8.0 (d, 2H), 7.79 (m, 2H), 7.6 (d, 2H), 7.18 (m, 6H), 5.3 (s, 2H), 2.9 (m, 4H).

EXAMPLE 28

Preparation of 4-(2-(2-phenethyl)phenoxymethyl)-2-hydroxybenzoic Acid

A solution of 2-hydroxy-4-methylbenzoic acid (20.0 g, 0.132 mol) in methanol (200 ml) was cooled in an ice bath. Concentrated, H$_2$SO$_4$ (20 ml) was added cautiously and the reaction heated to reflux and held at reflux for 48 hours. The reaction was allowed to cool to ambient temperature, the solvent evaporated and the residue purified by chromatography (eluant: CH$_2$Cl$_2$) to give methyl 2-hydroxy-4-methylbenzoate (19.76 g, 90%).

NMR (200 MHz, DMSO-d$_6$): δ10.47 (s, 1H), 7.64 (d, 1H), 6.78 (m, 2H), 3.86 (s, 3H), 2.3 (s, 3H).

A solution of methyl 2-hydroxy-4-methylbenzoate (19.7 g, 0.119 mole) in pyridine (15 ml) was treated with acetic anhydride (15 ml, 16.23 g, 0.158 mol). The reaction was stirred at ambient temperature overnight and then the solvent evaporated. The residue was dissolved in CH$_2$Cl$_2$ and the solution washed with 2N aqueous HCl, water, saturated aqueous NaHCO$_3$ solution, dried (MgSO$_4$) and evaporated to give methyl 2-acetoxy-4-methylbenzoate which was used without further purification (24.58 g, 99%).

NMR: (250 MHz, DMSO-d$_6$): δ7.84 (d, 1H), 7.21 (m, 1H), 7.04 (bs, 1H), 3.28 (s, 3H), 2.38 (s, 3H), 2.26 (s, 3H).

A solution of methyl 2-acetoxy-4-methylbenzoate (24.5 g, 0.118 mole) in carbon tetrachloride (700 ml) was treated with N-bromosuccinimide (20.96 g, 0.118 mole), benzoyl peroxide (0.5 g, catalytic) and AIBN (0.03 g). The reaction mixture was heated to reflux, held at reflux for 1 hour and then allowed to cool to ambient temperature, filtered and evaporated to give methyl 2-acetoxy-4-bromomethylbenzoate which was used without further purification (34 g, 63% of mixture is desired product).

A solution of 2-(2-phenethyl)phenol (2.0 g, 10 mmol) in DMF (20 ml) was heated with K$_2$CO$_3$ (2.8 g, 20 mmol) and methyl 2-acetoxy-4-bromomethylbenzoate (5.1 g, 12.3 mmol). The reaction was stirred at ambient temperature for 48 hours, then partitioned between ethyl acetate and water. The organic phase was washed with water (3×), dried (MgSO$_4$) and evaporated. The residue was purified by chromatography (eluant: ethyl/hexane) to give 4-(2-(phenethyl)phenoxymethyl)-2-acetoxybenzoate (1.78 g, 44%).

NMR (200 MHz, DMSO-d$_6$): δ7.98 (d, 1H), 7.46 (m, 1H), 7.22 (m, 8H), 6.95 (m, 2H), 5.21 (s, 1H), 3.82 (s, 3H), 2.86 (m, 4H), 2.28 (s, 3H).

The product from previous step (1.54 g, 3.81 mmol) was dissolved in ethanol (20 ml) and THF (15 ml) and 1N aqueous NaOH, (7.6 ml) was added. The reaction was stirred at ambient temperature for 30 hours then the solvent partially evaporated and diluted with water. Acetic acid was added dropwise until no further precipitation was observed. The solution was extracted with ethyl acetate (2×) and the organic phase dried (MgSO$_4$) and evaporated. The residue was purified by chromatography (eluant: methanol/CH$_2$Cl$_2$) to give the title product (0.59 g, 44%), m.p. 124.2–126° C.

NMR (200 MHz, DMSO-d$_6$): δ7.78 (d, 1H), 7.2 (m, 7H), 6.95 (m, 4H), 5.12 (s, 2H) , 2.88 (m, 4H).

EXAMPLE 29

4-(2-(2-Phenethyl)-6-bromophenoxymethyl)-2-hydroxybenzoic acid was prepared from 6-bromo-2-(2-phenethyl)phenol and 2-acetoxy-4-bromomethylbenzoate using a similar method to that of Example 28, m.p. 124.8–133° C.; MS –ve FAB: 425/427 [M–H]–

EXAMPLE 30

Preparation of 4-(2-benzyl-6-bromophenoxymethyl) benzoic acid: Methyl 4-(2-benzyl-6-bromophenoxymethyl) benzoate (prepared below) was dissolved in ethanol (50 ml) and THF (15 ml) and treated with a solution of sodium hydroxide (1N, 32 ml). The reaction was stirred for 72 hours, partially evaporated and the residue diluted with water and acidified with ethyl acetate to give a precipitate. The precipitate was recrystallised from ethanol/water to give the title product. MS (CI$^+$): 397(M+H)$^+$ Elemental analysis: Calc: 63.5%C, 4.31%H Found: 63.3%C, 4.3%H The methyl 4-(2-benzyl-6-bromophenoxymethyl) benzoate used above was prepared as follows:

A solution of 2-bromophenol (4.7 g, 27.2 mmol) in toluene (50 ml) was treated with benzaldehyde (3.75 g, 35.3 mmol), phenylboronic acid (3.98 g, 32.6 mmol) and trichloroacetic acid (1.33 g, 8.1 mmol). The mixture was heated to reflux and held at reflux for 18 hours. The reaction mixture was then evaporated and the residue subjected to chromatography to give the boronic acid complex of the adduct which was used in the subsequent step without further purification.

Borane-tert-butylamine complex (8.51 g, 97.8 mmol) was added to a suspension of AlCl$_3$ (6.5 g, 48.8 mmol) in dichloromethane (20 ml), at 0° C. The mixture was stirred for 0.75 hours, at 0° C., to give a fine white suspension. The boronic acid complex (prepared above) in dichloromethane (10 ml) was then added and the mixture allowed to warm to ambient temperature and to stir overnight. Hydrochloric acid (1N) was added dropwise until pH1 was achieved. A white precipitate appeared transiently. The mixture was extracted with dichloromethane (×2), the organic phase dried (MgSO$_4$) and evaporated and the residue purified by chromatography eluting with ethyl ether/hexane to give 2-benzyl-6-bromophenol (3.58 g, 50%) as an oil. MS(CI$^+$):262(M$^+$).

A solution of 2-benzyl-6-bromophenol (3.2 g, 12.2 mmol) in DMF (50 ml) was treated with K$_2$CO$_3$ (2.19 g, 15.9 mmol) and methyl 4-bromomethylbenzoate (3.21 g, 14.02 mmol). The reaction was stirred at ambient temperature overnight, filtered and partitioned between ethyl acetate and water. The organic phase was washed with water (4×), dried (MgSO$_4$) and evaporated to give methyl 4-(2-benzyl-6-bromophenoxymethyl)benzoate (5.96 g), which was used without further purification. MS(CI$^+$):411(M+H)$^+$

EXAMPLE 31

4-[2-(2-Phenethyl)phenoxyethyl]benzoic Acid

A solution of methyl 4-[2-(2-phenethyl)phenoxyethyl] benzoate (0.44 g, 1.2 mmol) in methanol (20 ml) and THF (5 ml) was treated with NaOH (1N, 5 ml). The reaction was heated to reflux for 4 hours. The reaction was evaporated at reduced pressure. The residual solution was acidified to pH1 with 1N HCl. The acidic solution was extracted with ethyl acetate, dried over MgSO$_4$ and evaporated to give the title compound as a viscous oil (0.29 g, 67%).

Elemental analysis: Calc for C$_{23}$H$_{22}$O$_3$: 79.7% C 6.40%H Found: 77.7% C 6.50%H Calc for C$_{23}$H$_{22}$O$_3$.05H$_2$O: 77.8% C 6.5%H NMR (200MH$_2$, DMSO-d$_6$), δ1.6 (d, 3H), 2.9 (m, 4H), 5.57 (q, 1H), 6.78 (m, 2H), 7.15 (m, 7H), 7.53 (d, 2H), 7.9 (d, 2H).

The starting material was prepared as follows:

4-ethyl benzoic acid (5.0 g, 26.7 mmol) was dissolved in methanol (40 ml) and treated with concentrated H$_2$SO$_4$ (0.5 ml). The reaction was heated at reflux for 24 hours. The reaction was evaporated at reduced pressure, partitioned between ethyl acetate/H$_2$O. The aqueous layer was washed with ethyl acetate (1×). The organic phases were combined, washed with H$_2$O, dried over MgSO$_4$ and evaporated. The material was used without further purification in the subsequent transformation.

A solution of methyl 4-ethyl benzoate (5.4 g, 33.3 mmol) in CCl$_4$ (200 ml) was treated with N-bromosuccinimide (5.93 g, 33.3 mmol). The mixture was treated with benzoylperoxide (0.1 g). The reaction was heated to reflux for 2 hours. After cooling the reaction mixture was filtered and evaporated to obtain 8.1 g of pale yellow oil (quantitative).

This material was used without further purification in the subsequent step.

NMR (200 MHz DMSO-d$_6$): δ2.0 (d, 3H), 3.90 (s, 3H), 5.54 (q, 1H), 7.65 (d, 2H), 7.77 (d, 2H).

2-(2-Phenethyl)phenol (1.5 g 7.6 mmol) was dissolved in DMF (5 ml). The solution was treated with K$_2$CO$_3$ (2.2 g, 16 mmol) and methyl 4-(1-bromoethyl)benzoate (2.0 g, 8.3 mmol). The reaction was allowed to stir for 60 hours at room temperature then heated to 90° C. for 4 hours. The reaction was partitioned between ethyl acetate/H$_2$O. The aqueous layer was washed with ethyl acetate (1×). The combined organic layers were washed with H$_2$O (4×), dried over MgSO$_4$ and evaporated. Purification by chromatography (ethyl acetate/hexane) gave 1.99 g of methyl 4-[2-(2-phenethyl)phenoxymethyl]benzoate as a colourless oil (73%).

NMR (DMSO d6/200 MHz): δ1.58 (d, 3H), 2.9 (m, 4H), 3.83 (s, 3H), 5.59 (q, 1H), 6.77 (t, 2H), 6.96–7.33 (m, 7H), 7.57 (d, 2H), 7.95 (d,.2H). MS CI$^+$:360 (M$^+$)

Reference Example 1

Methyl 4-[6-methyl-2-(2-phenethyl)phenoxymethyl] benzoate

A mixture of 2-(2-phenethyl)-6-methylphenol (0.59 g 2.78 mmol), methyl 4-bromomethylbenzoate (0.96 g 4.21 mmol) and potassium carbonate (0.59 g) in DMF (30 ml) was stirred under argon at ambient temperature for 48 hours. The reaction mixture was diluted with water (50 ml) and extracted twice with ethyl acetate (50 ml each time). The ethyl acetate extracts were dried (MgSO$_4$) and the residue obtained on removal of the solvent was subjected to chromatography on silica, eluting with a mixture of ethyl acetate and hexane (1:50 v/v) to give methyl 4-[6-methyl-2-(2-phenethyl)phenoxymethyl]benzoate (0.95 g; 94%). MS (CI$^+$):378 (M+NH$_4$)$^+$

Reference Example 2

A similar method to that outlined in Reference Example 1, except using the appropriately substituted phenol in place of 2-(2-phenethyl)-6-methylphenol, was used to prepare the compounds of Table XV.

TABLE XV

[Structure: benzene ring with positions 3,4,5,6 labeled, R at position 3, OCH₂-C₆H₄-COOMe group, and X—Ph substituent]

| Compound No. | R | -x- | Reaction time (hours) | Equivalents of K₂CO₃ | Equivalents of bromo compound | MS | Footnotes |
|---|---|---|---|---|---|---|---|
| 1 | 6-OMe | —CH₂CH₂— | 18 | 1.2 | 1.2 | CI⁺: 377 (M + H)⁺ | b, c |
| 2 | 6-Cl | " | 18 | 1.5 | 1.5 | +veFAB: 381 (M + H)⁺ | b, h |
| 3 | 5-Cl | " | 60 | 1.3 | 1.1 | | a, f |
| 4 | 5-MeO | " | 72 | 1.3 | 1.1 | | a, f |
| 5 | 5-Me | " | 48 | 1.3 | 1.1 | | a, f |
| 6 | 6-NO₂ | " | 18 | 1.5 | 1.5 | EI⁺: 389 (M°)⁺ | b, h |
| 7 | 5-Br | " | 60 | 1.3 | 1.1 | | c, e |
| 8 | 4-CO₂Et | " | 18 | 1.5 | 1.2 | | c, f, j |
| 9 | 4-CONEt₂ | " | 18 | 1.3 | 1.1 | | c, f |
| 10 | 4-CH₂OH | " | 18 | 1.5 | 1.2 | | c, f |
| 11 | 4-Cl | " | 18 | 1.5 | 1.1 | | c, f |
| 12 | 4-COCH₃ | " | 18 | 1.5 | 1.2 | | c, f |
| 13 | 4-SMe | " | 18 | 1.3 | 1.1 | | c, f |
| 14 | 4-Br | " | 18 | 1.3 | 1.1 | | c, e, i |
| 15 | 4-NO₂ | " | 48 | 1.3 | 1.1 | | c, f |
| 16 | 4-OCH₃ | " | 24 | 1.3 | 1.1 | | c, f |
| 17 | 4-CH₃ | " | 18 | 1.3 | 1.1 | | c, f |
| 18 | 4-hexyl | " | 24 | 1.3 | 1.1 | | b, f |
| 19 | 4-OCOtBu | " | 24 | 1.3 | 1.1 | | b, f |
| 20 | 4-CHO | " | 18 | 1.3 | 1.1 | | b, f |
| 21 | 6-iPr | " | 18 | 1.5 | 1.5 | (CI⁺): 406 (M + NH₄)⁺ | b, g |
| 22 | 6-Br | " | 60 | 1.3 | 1.3 | (CI⁺): 442 (M + H)⁺ | b, f |
| 23 | 6-Ph | " | 48 | 1.3 | 1.2 | (CI⁺): 440 (M + NH₄)⁺ | a, f |
| 24 | 6-hexyl | " | 60 | 1.5 | 1.1 | (CI⁺): 431 (M + H)⁺ | b, f |
| 25 | 6-CHO | " | 18 | 2.0 | 1.1 | (EI⁺): 374 (M⁺) | b, f |
| 26 | 6-SMe | " | 18 | 2.0 | 1.3 | (CI⁺): 393 (M + H)⁺ | b, f |
| 27 | 6-CONEt₂ | " | 18 | 2.0 | 1.0 | (+ve FAB): 446 (M + H)⁺ | b, g |
| 28 | not used | | | | | | |
| 29 | 6-Br | —CH=CH— | 60 | 2.0 | 1.1 | (+ve FAB): 423 (M + H)⁺ | b, f |
| 30 | 4-Me, 6-Br | —CH₂CH₂— | 18 | 2.5 | 1.1 | (EI⁺): 438 (M')⁺ | b |
| 31 | 4-Br, 6-Br | " | — | 2.5 | 1.1 | (CI⁺): 471 (M⁺ + MeOH)⁺ | b, f |
| 32 | 4-Cl, 6-Me | " | 18 | 21.2 | 1.1 | (EI⁺): 394 (M')⁺ | d, f |
| 33 | 4-F, 6-Br | " | 18 | 2.5 | 1.1 | (CI⁺): 433 (M + H)⁺ | b, f |
| 34 | 4,6-ditBu | " | 18 | 2.5 | 1.1 | (EI⁺): 458 (M¹)⁺ | b, f |
| 35 | 4-Me, 6-OMe | " | 72 | 1.5 | 1.22 | | c, f |
| 36 | 4-OMe, 6-Br | " | 18 | 1.5 | 1.24 | | c, f |
| 37 | 4-Me, 6-tBu | " | 18 | 1.5 | 1.24 | | c, f |
| 38 | 4,6-tBu | " | 18 | 1.5 | 1.24 | | c, f |
| 39 | 4-Br | " | 18 | 1.3 | 1.1 | | c, e |
| 40 | 5-OCOtBu | " | 48 | 1.3 | 1.1 | | a, f |
| 41 | H | " | 48 | 1.1 | 1.3 | | a, k |

Footnotes
a The reaction mixture was evaporated at reduced pressure. The residue was partitioned between ethyl acetate/water. The organic extract was washed with brine, dried (MgSO₄) and evaporated.
b The reaction mixture was partitioned between ethyl acetate/water. The organic phase was washed well with water (4x), dried (MgSO₄) and evaporated.
c The reaction mixture was filtered and then evaporated at reduced pressure. The residue was partitioned between ethyl acetate/water. The organic phase was washed with brine, dried (MgSO₄) and evaporated.
d The reaction mixture was filtered and then partitioned between ethyl acetate/water. The organic phase was washed well with water (4x), dried (MgSO₄) and evaporated.
e Used subsequent step without further purification
f Purified by chromatography using diethylether/hexane as eluant.
g Purified by chromatography using ethyl acetate/hexane as eluant.
h Purified by chromatography using dichloromethane/hexane as eluant.
i See reference example 24 for preparation of phenol.
j Starting phenol prepared as per reference example 42 a)
k Phenol prepared according to JACS 81 2795 (1959)

Reference Example 3
Not used.

Reference Example 4
Methyl 4-[5-t-butylcarbonyloxy- (2 -phenethyl) phenoxymethyl]benzoate Triethylamine (5 ml) was added to a stirred suspension of 2,4-dihydroxybenzaldehyde (12 g) in dichloromethane (50 ml) at −8° C. To this mixture was added t-butylcarbonyl chloride (4.4 ml) and the mixture was allowed to warm to ambient temperature and was stirred at this temperature for 16 hours. The reaction mixture was washed consecutively with aqueous 1N hydrochloric acid (20 ml), water (20 ml) and saturated aqueous sodium bicarbonate solution (20 ml) and then dried (MgSO₄). The residue obtained on removal of the solvent was subjected to chromatography on silica eluting with a mixture of ethyl acetate and hexane (1:9 v/v) to give 4-(t-butylcarbonyloxy)-2-hydroxy-benzaldehyde (5.82 g; 35%).

The 5-(t-butylcarbonyloxy)-2-(2-phenethenyl)phenol was prepared by reaction of 4-(t-butylcarbonyloxy)-2-hydroxybenzaldehyde with benzyltriphenylphosphonium bromide using a similar method to that described in Reference Example 12.

The 5-(t-butylcarbonyloxy)-2-(2-phenethyl)phenol was prepared by hydrogenation of 5-(t-butylcarbonyloxy)-2-(2-phenethenyl)phenol as described in Reference Example 8.

The methyl 4-[5-t-butylcarbonyloxy-2-(2-phenethyl) phenoxy-methyl]benzoate was prepared from 5-(t-butylcarbonyloxy)-2-(2-phenethyl)phenol and methyl 4-bromomethylbenzoate as described in Reference Example 1.

Reference Example 5

4-[4-Bromo-2-(2-phenethyl)phenoxymethyl]benzonitrile

The 4-[4-bromo-2-(2-phenethyl)benzonitrile used as starting material in Example 5 was prepared by reacting 4-bromo-2-(2-phenethyl)-phenol and 4-bromomethylbenzonitrile under similar conditions to those described in Reference Example 1.

Reference Example 6

The compounds of Table XVI were prepared by reacting 4-bromomethylbenzonitrile with the appropriate phenol using a similar method to that described in Reference Example 5.

Reference Example 7

The t-butyl esters used as starting material in Examples 3 and 4 were prepared from the appropriately substituted 2-(2-phenethyl)-phenols and t-butyl 4-bromomethylbenzoate (Tilley et al J Med Chem 34 1125–36 (1991)) using a similar method to that described in Reference Example 1.

TABLE XVII

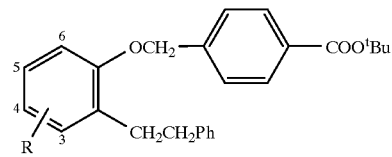

| R | Equivalents of: | | Time | Data | Footnotes |
|---|---|---|---|---|---|
| | Bromo Compound | $K_2CO_3$ | | | |
| 6-$CO_2$Me | — | — | — | (+veFAB): 469 [M + Na]$^+$ | a, d |
| 6-CHO | 2.65 | 2.0 | — | (EI$^+$): 416 (M$°$)$^+$ | a, d |
| 4-$CO_2$Me | 1.2 | 1.33 | 72 | — | c, e |

Footnotes
a Extracted
b Evaporated
c Evaporated then extracted
d Purified by chromatography using diethyl ether/hexane as eluant
e Purified by chromatography using ethyl acetate/hexane as eluant

TABLE XVI

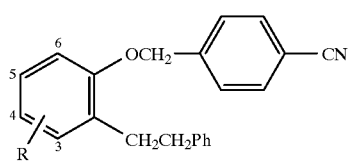

| R | Equivalents of: | | Reaction Time (Hours) | Footnote | MS |
|---|---|---|---|---|---|
| | Bromo Compound | $K_2CO_3$ | | | |
| 4-hexyl | 1.1 | 1.5 | 60 | d, f | — |
| 4-OH | 1.1 | 1.33 | 24 | c, f | — |
| 4-Cl | 1.1 | 1.5 | 18 | d, f | — |
| 4-$OCH_3$ | 1.1 | 1.3 | 72 | d, e | — |
| 6-iPr | 1.3 | 1.3 | 18 | b, g | (CI$^+$): 373 (M + $NH_4$)$^+$ |
| 6-Ph | 1.2 | 1.3 | 48 | a, f | (CI$^+$): 390 (M + H)$^+$ |
| 6-Br | 1.1 | 2.0 | 18 | b | (CI$^+$): 392 (MH)$^+$ |
| 6-hexyl | 1.1 | 1.5 | 48 | b, f | (CI): 398 (MH)$^+$ |
| H | 1.1 | 1.3 | 48 | b, g | EI$^+$ 313 (M)$^+$ |
| 5-Cl | 1.1 | 1.3 | 48 | d, g | — |
| 5-$OCH_3$ | 1.1 | 1.3 | 48 | a, c, e | — |

Footnotes
a Evaporate
b Extract
c Extract and extract
d Evaporate and extract
e The product was used in the subsequent step without further purification
f Purified by chromatography using dichloromethane/hexane as eluant
g Purified by chromatography using diethyl ether/hexane as eluant

Reference Example 8

5-Methyl-2-(2-phenethyl)phenol

A solution of (E)-5-methyl-2-(2-phenethenyl)phenol (1.1 g) in ethanol (80 ml) containing 10% palladium/carbon as catalyst (200 mg) was hydrogenated at atmospheric pressure. The catalyst was removed by filtration through acid washed silica and the filtrate concentrated to give 5-methyl-2-(2-phenethyl)phenol as a gum (yield 1.1 g).

Reference Example 9

The compounds of Table XVIII were prepared from the appropriate olefin using a similar method to that described in Reference example 8.

TABLE XVIII

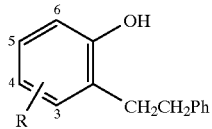

| R | Footnotes |
| --- | --- |
| 4-CH$_3$ | b |
| 4-OCH$_3$ | b |
| 4-CO$_2$Et (benzyl ether) | j, k |
| 4-CONEt$_2$ (benzyl ether) | |
| 4-CO$_2$Me (benzyl ether) | a |
| 4-OCOtBu | |
| 4,6-di-t-Bu | e, g |
| 4-Me, 6-OMe | |
| 4-Me, 6-tBu | c, e |
| 5-OCOtBu | |
| 5-MeO | |
| 6-Cl | |
| 6-MeO | |

Footnotes
a methanol was used as the solvent instead of ethanol
b reaction time under 4 hours
c reaction time 48 hours
d purified from ethyl acetate/hexane
e purified from ethyl ether/hexane
f purified by chromatography using diethyl ether/hexane as eluant
g MS (EI+): 310 (M°)$^+$

TABLE XVIII-continued

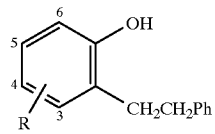

| R | Footnotes |
| --- | --- | h MS (CI$^+$): 283 (M + H)$^+$
i m.p. 45.5–46° C.
j used to prepare 4-COOH and 4-CH$_2$OH compounds
k the starting material was prepared according to reference example 44a)–d)

Reference Example 10

2-(2-Phenethyl)-6-nitrophenol

A solution of 2-(2-phenethenyl)-6-nitrophenol (6.82 g) in a mixture of ethanol (200 ml) and toluene (200 ml) containing Wilkinson's catalyst (tris(triphenylphosphine) rhodium(I)chloride) (638 mg) was hydrogenated at 50° C. at a pressure of 50 atmospheres for 13 hours. The catalyst was removed by filtration and the filtrate was evaporated to dryness to give 2-(2-phenethyl)-6-nitrophenol (5.38 g; 78%) which was used in subsequent reactions without further purification.

Reference Example 11

The compounds of Table XIX were prepared from the appropriate olefin using a similar method to that of Reference example 10.

TABLE XIX

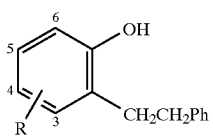

| Compound No. | R | Pressure (bar) | Time (hours) | MS | Footnotes |
|---|---|---|---|---|---|
| 1 | 6-Br | 50 | 24 | (CI)$^+$: 442 (M + H)$^+$ | a |
| 2 | 4-SMe | 50 | 18 | | a |
| 3 | 4-Cl | 50 | 18 | | a |
| 4 | 4,6-di-F | 60 | 24 | | b |
| 5 | 4,6-di-Br | 50 | 24 | (EI): 353 (M°)+ | a |
| 6 | 4-OCH$_3$, 6-Br | 60 | 24 | | a |
| 7 | 4-F, 6-Br | 50 | 24 | (CI): 294 (M + NH$_4$ + H$_2$O)$^+$ | a |
| 8 | 4-Cl, 6-Me | 50 | 18 | (EI$^+$): 246 (M°)$^+$ | c |
| 9 | 4-Me, 6-Br | 50 | 24 | (EI$^+$): 290 (M°)$^+$ | a |
| 10 | 5-Br | 50 | 18 | | a |

Footnotes
a purified by Chromatography using diethyl ether/hexane as eluant
b used in subsequent step without further purification
c purified by Chromatography using dichloromethane as eluant

Reference Example 12

E 5-Methyl-2-(2-phenethenyl)phenol was prepared as follows:

A solution of lithium bis(trimethylsilyl)amide in THF (37 ml of a 1N solution) was added to a stirred suspension of benzyltriphenylphosphonium bromide (8.76 g) in THF (60 ml) at ambient temperature under argon and the mixture was stirred for 45 minutes. A solution of 4-methyl-2-hydroxybenzaldehyde (made from 4-methylsalicylic acid by the procedure described in reference example 53a)–b)) (2.4 g) in THF (15 ml) was added and the reaction mixture stirred for 16 hours. The reaction mixture was partitioned between water (100 ml) and diethyl ether (100 ml). The aqueous phase was extracted once with diethyl ether and the combined extracts were dried (MgSO$_4$). The oil obtained on removal of the solvent was subjected to chromatography on silica, with a mixture of ethyl acetate and hexane (1:4 v/v) to give (E)5-methyl-2-(2- phenethenyl)phenol (1.1 g; 26%).

Reference Example 13

The compounds of Table XX were prepared from the appropriate aldehyde using a similar method to that of Reference example 12.

TABLE XX

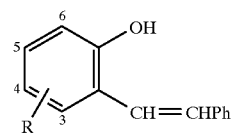

| Compound No. | R | Equivalents of phosphonium salt | Equivalents of base | Reaction time | MS | Footnotes |
|---|---|---|---|---|---|---|
| 1 | 5-MeO | 1.14 | 2.3 | 72 hours | | b |
| 2 | 6-Cl | 2.23 | 2.27 | 18 hours | | b |
| 3 | 6-MeO | 1.1 | 2.2 | 5 days | | b |
| 4 | 6-NO$_2$ | 1.5 | 2.2 | 48 hours | | b |
| 5 | 4-Me, 6-tBu | 1.14 | 2.5 | 72 hours | | a |
| 6 | 4-Me, 6-OMe | 1.14 | 2.33 | 3 days | | a, d |
| 7 | 4,6-di-tBu | 1.10 | 2.2 | 48 hours | (CI$^+$): 309 (M + H)$^+$ | a |
| 8 | 4-OMe, 6-Br | 1.14 | 2.4 | 4 days | | a, f |
| 9 | 4,6-di-Br | 1.10 | 2.1 | 48 hours | (EI)$^+$: 353 (M°)$^+$ | a |
| 10 | 4-F, 6-Br | 1.10 | 2.1 | 48 hours | (CI$^+$): 292 (M°)$^+$ | a |
| 11 | 4-Cl, 6-Me | 1.10 | 2.1 | 18 hours | (EI$^+$): 244 (M°)$^+$ | a |
| 12 | 4-Me, 6-Br | 1.10 | 2.1 | 48 hours | (CI$^+$): 288 (M + NH$_{4-H_2O}$)$^+$ | a |
| 13 | 4,6-di-F | 1.10 | 2.2 | 48 hours | | a |
| 14 | not used | | | | | |
| 15 | 6-hexenyl | 1.10 | 2.2 | 3 days | (CI$^+$): 276 (M + H)$^+$ | a |
| 16 | 6-Br | 1.10 | 2.2 | 4 days | (CI$^+$): 276 (M + H)$^+$ | a |
| 17 | 4-hexenyl | 1.10 | 2.2 | 4 days | | a |

TABLE XX-continued

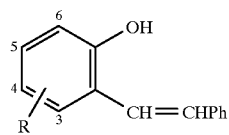

| Compound No. | R | Equivalents of phosphonium salt | Equivalents of base | Reaction time | MS | Footnotes |
|---|---|---|---|---|---|---|
| 18 | 4-OMe | 1.14 | 2.3 | 4 days | | a |
| 19 | 4-CH$_3$ | 1.15 | 2.3 | 3 days | | a |
| 20 | 4-SMe | 1.10 | 2.2 | 3 days | | a |
| 21 | 4-Cl | 1.00 | 2.1 | 18 hours | | b |
| 22 | 4-OCOtBu | 1.10 | 2.2 | 18 hours | | b |
| 23 | 5-Br | 1.15 | 2.3 | 5 days | | a, e |

Footnotes
a purified by Chromatography using diethyl ether/hexane as eluant
b purified by Chromatography using ethyl acetate/hexane as eluant
c purified by Chromatography using dichloromethane/hexane as eluant
d starting material prepared according to the method described in JCS Perkin II (1980), 354 and JCS (1941), 548
e for preparation of starting material see Kobayashi, Azekaura Morita, Chem Pharm Bull (Japan), 17, 89–93, (1969
f starting material prepared according to JCS 1998 (1925)

Reference Example 14

3,5-Dibromo-2-hydroxybenzaldehyde

Hexamine (3.35 g, 23.92 mmol) was added portionwise to trifluoroacetic acid (25 ml) keeping the temperature below 40° C. with a water bath. 2,4-Dibromophenol was then added slowly and the reaction mixture heated at 80° C. for 3½ hours. The reaction mixture was cooled, partially evaporated and then poured into ice/water. This mixture was stirred at ambient temperature overnight and the precipitate that formed filtered, dried and purified by chromatography (CH$_2$Cl$_2$/hexane) to give the title compound (2.1 g).
MS (CI)$^+$:279 [M+H]$^+$ NMR: (250 MHz, DMSO-d$_6$):

Reference Example 15

The compounds of Table XXI were prepared from the appropriate phenol using a similar method to that of Reference example 14.

TABLE XXI

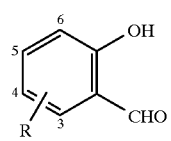

| Compound No. | R | Reaction time (hours) | Stir time (hours) | Footnotes |
|---|---|---|---|---|
| 1 | 4-F, 6-Br | 3½ | 24 | a |
| 2 | 4-Me, 6-Br | 4 | 24 | b, c, e |
| 3 | 4-Me, 6-tBu | 3½ | 48 | d |

Footnotes
a Isolated by filtering
b Isolated by extraction with ethyl acetate
c Purified by Chromatography using diethyl ether/hexane as eluant
b Purified by Chromatography using hexane as eluant
e MS (CI$^+$): 215/217 (M + H)$^+$ Reference Example 16

3-Bromo-2-hydroxybenzaldehyde

Over 0.25 hours 2-bromophenol (22.38 g, 129 mmol) was added to a solution of Mg(OMe)$_2$ in methanol (111.9 ml, 8% w/w) and toluene (35 ml). The reaction was heated to reflux and maintained at reflux for 1 hour, then toluene (118 ml) was added. The solvent was distilled off until the temperature reached 92–94° C. A solution of paraformaldehyde in toluene was added portionwise over 1 hour at 80–90° C. and the reaction mixture heated to reflux and maintained at reflux for 3 hours. The reaction mixture was then allowed to cool to ambient temperature and left to stand overnight. Toluene (140 ml) was added to the reaction mixture, which was then washed with 2M H$_2$SO$_4$ (140 ml). The organic phase was dried and evaporated and the crude material used in the next step without further purification.
MS (CI$^+$):201 [M+H]$^+$ Reference Example 17

The compounds of table XXII were prepared from the appropriate phenol using a similar method to that of Reference example 16.

TABLE XXII

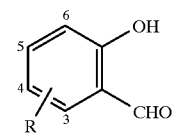

| Compound No. | R | Reaction time Step 1; Step 2 (hours) | MS | Footnote |
|---|---|---|---|---|
| 1 | 4,6-di-t-Bu | 1.25; 3 | (CI$^+$): 235 (M + H)$^+$ | a |
| 2 | 4-Cl, 6-Me | 1.5; 3 | (EI$^+$): 170 (M$°$)$^+$ | a |
| 3 | 6-hexenyl | 2; 3 | (CI$^+$): 205 (M + H)$^+$ | a |
| 4 | 4-hexenyl | 1; 3 | | a |
| 5 | 4-SMe | 1; 3 | | a |
| 6 | not used | | | |
| 7 | 4,6-diF | 1; 3.5 | (CI$^+$): 159 (M + H)$^+$ | b |

Footnote
a Purified by Chromatography using diethyl ether/hexane as eluant
b Purified by Chromatography using dichloromethane/hexane as eluant Reference Example 18

Ethyl 2-bromomethyl-5-thiazolecarboxylate

A solution of ethyl 2-methyl-5-thiazole carboxylate [S. H Mashragui, P. M. Keehn, JACS 104 4461–4465 (1982)]

(4.73 g, 27.68 mmol) in carbon tetrachloride (30 ml) was treated with N-bromosuccinimide (4.92 g, 27.64 mmol) and benzoyl peroxide (0.03 g). The reaction mixture was heated to reflux under a strong light for 1¼ hours. The reaction was allowed to cool to ambient temperature and filtered. The filtrate was evaporated and subjected to chromatography (CH$_2$Cl$_2$) to give the title product (1.16 g, 17%). NMR (200 MH$_z$,DMSO-d$_6$) : δ8.4 (s, 1H) , 5.06 (s, 2H) , 4.33 (g, 2H), 1.3 (t, 3H).

Reference Example 19

Methyl 4-[4-Cyano-2-(2-phenethyl)phenoxymethyl] benzoate a) A solution of methyl-4-[4-bromo-2- (2-phenethyl) phenoxy-methyl ]benzoate (4.0 g) in DMF (120 ml) containing cuprous cyanide (2.08 g) was stirred and heated under reflux for 24 hours in an atmosphere of argon. The reaction mixture was allowed to cool and was added to a solution of 1,2-diaminoethane (120 ml) in water (600 ml). The mixture was extracted four times with diethyl ether (150 ml each time), washed with brine (100 ml) and evaporated to dryness. Toluene (100 ml) was added to the residue and the mixture evaporated to dryness. The residue was subjected to chromatography on silica, eluting with a mixture of diethyl ether and hexane (1:3 v/v) to give methyl-4-[4-cyano-2-(2-phenethyl)phenoxymethyl]benzoate (3.3 g; 94%).

b) The starting material was prepared as follows:

Tetrabutylammonium tribromide (10.00 g) was added to a solution of 2-(2-phenethyl)phenol (3.77 g) in dichloromethane (140 ml) at ambient temperature and the mixture stirred for 2 hours. The reaction mixture was washed consecutively with aqueous sodium thiosulphate solution (2×100 ml), water (3×100 ml) and brine (100 ml) and then dried (MgSO$_4$). Removal of the solvent gave an oil which was subjected to chromatography on silica, eluting with a mixture of ethyl acetate and hexane (1.9 v/v), to give as an oil 4-bromo-2-(2-phenethyl)phenol (4.5 g; 85%).

The methyl 4-[4-bromo-2-(2-phenethyl)phenoxymethyl] benzoate was prepared by reaction of 4-bromo-2-(2-phenethyl)phenol with methyl 4-bromomethylbenzoate using a similar method to that described in Reference Example 1.

Reference Example 20

The compounds of Table XXIII were prepared from the bromo compound using a similar method to that of Reference example 19a).

TABLE XXIII

| R | Position of —CO$_2$Me | Reaction Time (hours) | MS | Footnote |
|---|---|---|---|---|
| 5-CN | 1 | 20 | CI$^+$: 372 (M + H)+ | b |
| 6-CN | 1 | 18 | CI$^+$: 372 (M + H)$^+$ | c |
| 4-OMe, 6-CN | 1 | 20 | — | a |

TABLE XXIII-continued

| R | Position of —CO$_2$Me | Reaction Time (hours) | MS | Footnote |
|---|---|---|---|---|
| 4-Me, 6CN | 1 | 18 | CI$^+$: 385 (M$^+$)$^+$ | c |
| 6-CN | 2 | 4 | CI$^+$: 372 (M + H)$^+$ | c |

Footnotes
a 2.47 equivalents of CuCN used
b 2.5 equivalents of CuCN used
c 2.6 equivalents of CuCN used Reference Example 21

Preparation of methyl 4-[4-bromo-6-cyano-2-(2-phenethyl-phenoxymethyl ]benzoate and methyl 4-[6-bromo-4-cyano-2-(2-phenethyl-phenoxymethyl ]benzoate:

To a solution of methyl 4-[4,6-dibromo-2-(2-phenethyl-phenoxymethyl ]benzoate (0.92 g, 1.82 mmole) in DMF (30 ml) was added CuCN (0.188 g, 21. mmol). The reaction was heated at reflux (under argon) for 20 hours.

The reaction was cooled, poured into a solution of ethylene diamine (30 ml) in ice water (120 ml). The aqueous solution was extracted with ethyl acetate (3×60 ml). The combined organic extracts were washed with brine (2×), dried (MgSO$_4$) and evaporated. The residue was purified by chromatography (diethyl ether/hexane) to give the title compounds; 4-bromo-6-cyano compound (0.127 g) and 4-cyano-6-bromo compound (0.104 g).

4-bromo-6-cyano compound:

NMR (200 MHz, DMSO-d$_6$) δ: 8.02 (d, 2H), 7.98 (s, 1H), 7.85 (d, 1H), 7.6 (d, 2H), 7.16 (m, 5H), 5.19 (s, 2H), 3.88 (s, 3H), 2.84 (m, 4H).

4-cyano-6-bromo compound:

NMR (200 MHz, DMSO-d$_6$) δ: 8.14 (d, 1H), 8.02 (d, 2H), 7.85 (d, 1H), 7.65 (d, 2H), 7.18 (m, 5H), 5.07 (s, 2H), 3.89 (s, 3H), 2.87 (m, 4H).

Reference Example 22

Preparation of 6-cyano-2-(2-phenethyl)phenol

A solution of 6-bromo-2-(2-phenethyl)phenol (8.0 g, 28.88 mmol) in DMF (60 ml) was treated with K$_2$CO$_3$ (10.0 g, 72.46 mmol) and benzyl bromide (3.78 ml, 5.44 g, 31.79 mmol). The reaction was stirred for 3 hours at ambient temperature then filtered and evaporated. The residue was partitioned between ethyl acetate/water and the organic phase washed with H$_2$O (4×), dried (MgSO$_4$) and evaporated to give benzyl 6-bromo-2-(2-phenethyl)phenyl ether as an oil. (11.86 g [crude]). MS (EI) :366 (M)$^+$.

Benzyl 6-bromo-2-(2-phenethyl)phenyl ether (10.57 g, 28.8 mmol) was dissolved in DMF (100 ml). Cuprous cyanide (6.72 g, 75 mmol) was added and the reaction heated to 150° C. for 18 hours. The reaction was poured in ethylene diamine (440 ml) and water (1.5 l) and the product was extracted with ethyl acetate (3×). The organic extracts were combined, dried (MgSO$_4$) and evaporated. The residue was purified by chromatography (diethyl ether/hexane) to give benzyl 6-cyano-2-(2-phenethyl)phenyl ether as a solid (7.23 g, 80%). MS (CI$^+$): 314 (M+H)$^+$.

Benzyl 6-cyano-2-(2-phenethyl)phenyl ether (4.86 g, 15.5 mmol) was dissolved in ethanol (100 ml). The solution was treated with 10% Pd on Carbon (500 mg). The reaction was placed under an atmosphere of hydrogen and allowed to react with vigorous stirring for 2.5 hours. The reaction mixture was filtered through Celite and evaporated. The residue was purified by chromatography (diethyl ether/hexane) to give the title product (2.86 g, 83%). MS (CI$^+$): 224 [M+H]$^+$.

Reference Example 23

6-Methyl-2-(2-phenethyl)phenol

A solution of 1-(2-benzyloxy-3-methylphenyl)-2-phenylethene (2.19 g) in ethanol (50 ml) containing 10% palladium on charcoal as catalyst was hydrogenated at atmospheric pressure. The reaction mixture was filtered through acid washed silica and the residue obtained on concentration of the filtrate was subjected to chromatography on silica, eluting with a mixture of ethyl acetate and hexane (1:50 v/v) to give 6-methyl-2-(2-phenethyl)phenol (0.66 g; 42%; m.p. 45.5–46° C.).

Using this same procedure there was obtained

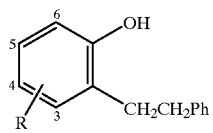

| Compound No. | R |
|---|---|
| 1 | 5-Cl |

The 1-[(2-benzyloxy-3-methyl) phenyl]-2-phenylethene used as starting material was prepared as follows:

A solution of lithium bis(trimethylsilyl)amide in THF (15.8 ml of a 1N solution) was added to a stirred suspension of benzyl triphenylphosphonium bromide (6.84 g) in THF (40 ml) and the mixture stirred under argon for 30 minutes. A solution of 2-benzyloxy-3-methylbenzaldehyde (2.38 g) (prepared from 2-hydroxy-3-methylbenzoic acid according to Reference example 29a)–c)); in THF (15 ml) was added to the reaction mixture and stirring continued for 48 hours. The reaction mixture was quenched with water (50 ml) and extracted three times with ethyl acetate (50 ml each time). The ethyl acetate extracts were dried (MgSO$_4$) and the residue obtained on removal of the solvent was subjected to chromatography on silica, eluting with an ethyl acetate/hexane mixture (1:100 v/v) to give 1-[(2-benzyloxy-3-methyl)phenyl]-2-phenylethene (2.47 g; 78%) as a mixture of E and Z isomers. MS (CI$^+$) (M+NH$_4$)$^+$318; (M+H)$^+$301.

This method was used to prepare 1-(2-benzyloxy-4-chlorophenyl)-2-phenylethene as a gum; 2-benzyloxy-4-chlorobenzaldehyde was prepared according to Reference example 29a)–c).

Reference Example 24

Preparation of 4-bromo-2-(2-phenethyl)phenol

Tetrabutylammonium tribromide (10.00 g) was added to a solution of 2-(2-phenethyl)phenol (3.77 g) in dichloromethane (140 ml at ambient temperature and the mixture stirred for 2 hours. The reaction mixture was washed consecutively with aqueous sodium thiosulphate solution (2×100 ml), water (3×100 ml) and brine (100 ml) and then dried (MgSO$_4$). Removal of the solvent gave an oil which was subjected to chromatography on silica, eluting with a mixture of ethyl acetate and hexane (1.9 v/v), to give as an oil 4-bromo-2-(2-phenethyl)phenol (4.5 g; 85%).

The 2-(2-phenethyl)phenol was prepared according to the route described in the literature JACS, 81, 2795, (1959).

Reference Example 25

Preparation of methyl 4-(2-(2-phenethyl)-6-hydroxy-phenoxymethyl)benzoate

A suspension of 2,3-dihydroxybenzaldehyde (15 g, 109 mmole) in CH$_2$Cl$_2$ (70 ml) was cooled to −10° C. Triethyl amine (5.49 g, 54.3 mmol) was added followed by pivaloyl chloride (6.49 g, 53.9 mmol). The reaction was allowed to stir for 1 hour at −10° C. and then warmed to ambient temperature. The reaction mixture was stirred at ambient temperature overnight, then washed with water, 1N aqueous HCl, saturated aqueous NaHCO$_3$ and water. The organic phase was dried (MgSO$_4$) and evaporated. The residue was purified by chromatography (eluant: ethyl acetate/hexane) to give 2-hydroxy-3-pivaloyloxybenzaldehyde: (10.15 g, 84%).

NMR (200 MHz, DMSO-d$_6$): δ10.78 (s, 1H), 10.15 (s, 1H), 7.64 (dd, 1H), 7.38(dd, 1H), 7.05 (t, 1H), 1.32 (s, 9H).

To a solution of 2-hydroxy-3-pivaloyloxybenzaldehyde (1.0 g, 4.5 mmole) in DMF (5 ml) was added Na$_2$CO$_3$ (0.859 g, 8.10 mmol) and methyl 4-bromomethylbenzoate (1.13 g, 4.93 mmol). The reaction was stirred at ambient temperature for 60 hours then partitioned between ethyl acetate/H$_2$O. The organic phase was washed with water (x1) dried (MgSO$_4$) and evaporated to give methyl 4-(2-formyl-6-pivaloyloxy-phenoxymethyl)benzoate as a product which was used in subsequent steps without further purification.

NMR (200 MHz, DMSO-d$_6$): δ10.12 (s, 1H), 7.97 (d, 2H), 7.67 (dd, 1H), 7.54 (m, 3H), 7.36 (t, 1H), 5.18 (s, 2H), 3.86 (s, 3H), 1.26 (s, 9H).

LiN(SiMe$_3$)$_2$ [1N in THF, 17.2 ml] was added to a suspension of benzyl triphenylphosphonium bromide (7.45 g, 17.2 mmol) in THF (80 ml). The reaction was stirred for 30 minutes at ambient temperature. A solution of methyl 4-(2-formyl-6-pivaloyloxyphenoxymethyl)benzoate (3.183 g, 8.59 mmole) in THF (20 ml) was added keeping the temperature below 40° C. The reaction was stirred at ambient temperature for 18 hours then treated with water, neutralised with dilute aqueous HCl and extracted with ethyl acetate. The organic phase was dried (MgSO$_4$) and evaporated. The residue was purified by chromatography (eluant: ethyl acetate/hexane) to give methyl 4-(2-(2-phenethenyl)-6-hydroxyphenoxymethyl)benzoate (1.68 g, 55%).

NMR (200 MHz, DMSO-d$_6$) (mixture of cis and trans isomers): δ9.52 (bs, 1H), 7.96 (m, 2H), 7.62 (m, 2H), 7.45 to 6.4 (complex multiplets, 10H) (two singlets together, 2H), 5.08 and 5.07 (two singlets together, 3H), 3.86 and 3.85 (two singlets together, 3H).

A solution of methyl 4-(2-(2-phenethenyl)-6-hydroxyphenoxy-methyl)benzenecarboxylate (1.39 g, 3.87 mmol) in ethanol (50 ml) and toluene (50 ml) was treated with Wilkinson's catalyst (0.15 g). The reaction was hydrogenated at 50° C. and 50 bar for 18 hours, then evaporated. The residue was purified by chromatography (eluant: ethyl acetate/hexane) to give methyl 4-(2-(phenethyl)-6-hydroxyphenoxy-methyl)benzoate: (1.12 g, 80%).

NMR (200 MHz, DMSO-d$_6$): δ9.40 (bs, 1H), 7.98 (d, 2H), 7.6' (d, 2H), 7.14 (m, 5H), 6.85 (t, 1H), 6.76 (dd, 1H), 6.66 (dd, 1H), 5.01 (s, 2H), 3.87 (s, 3H), 2.56 (bs, 4H).

Reference Example 26

Preparation of 6-(N-diethylcarbamoyl)-2-(2-phenethyl)phenol

To a suspension of hexane washed NaH (60% in mineral oil, 0.16 g, 4 mmol) in THF (5 ml) was added to a solution of 6-bromo-2-(2-phenethyl)phenol (1.0 g, 3.6 mmol) in THF (5 ml). The reaction was stirred at ambient temperature for 45 minutes then cooled to −70° C. A solution of n-butyl lithium (1.6M in hexane, 4.62 ml, 7.4 mmol) was added keeping the temperature below −55° C. The reaction mixture was stirred at −70° C. for 1.25 hours then poured onto crushed solid $CO_2$ in THF. The reaction was allowed to warm to ambient temperature, acidified with dilute HCl and extracted with ethyl acetate. The organic phase was dried ($MgSO_4$) and evaporated to give 2-hydroxy-3-(2-phenethyl)benzoic acid. The crude material was used without further purification in the subsequent step (0.805 g).

The crude 2-hydroxy-3-(2-phenethyl)benzoic acid (0.805 g 3.33 mmol) was dissolved in $CH_2Cl_2$ (15 ml) and treated with oxalyl chloride (0.55 ml, 0.8 g, 6.3 mmol) and 2 drops of DMF. The reaction was stirred at ambient temperature for 1 hour, then evaporated The residue was dissolved in $CH_2Cl_2$ (15 ml), evaporated and dissolved in dichloromethane (4 ml).

The acid chloride solution was added to a stirred solution of diethyl amine (1.19 g, 16.3 mmol) in dichloromethane (10 ml). The reaction mixture turned a deep green/brown colour. After 30 minutes the reaction was evaporated and the residue purified by chromatography (eluant: methanol/$CH_2Cl_2$) to give 6-(N-diethyl-carbamoyl)-2-(2-phenethyl) phenol (0.314 g, 32%).

NMR (200 MHz; DMSO-$d_6$): δ9.0 (bs, 1H), 7.23 (m, 5H), 7.09 (dd, 1H), 6.95 (dd, 1H), 6.78 (t, 1H), 3.31 (m, 4H), 2.85 (bs, 4H), 1.07 (t, 6H).

Reference Example 27

Preparation of 6-methylthio-2-(2-phenethyl)phenol

To a suspension of hexane washed NaH (60% in mineral oil, 0.238 mg, 5.95 mmol) in THF (4 ml) was added to a solution of 6-bromo-2-(2-phenethyl)phenol (1.5 g, 5.4 mmol) in THF (4 ml). The reaction was stirred for 30 minutes at ambient temperature, then cooled to −70° C. A solution of n-butyl lithium (1.6M in hexane, 3.72 ml, 5.95 mmol) was added keeping the temperature below −65° C. The reaction was stirred at −70° C. for 30 minutes and $Me_2S_2$ (0.25 g, 2.6 mmoles) added. The reaction temperature rose to −50° C. and was allowed to warm to ambient temperature. The reaction mixture was partitioned between ethyl acetate/dilute aqueous HCl, the organic phase was dried ($MgSO_4$) and evaporated and the residue purified by chromatography (eluant ethyl ether/hexane) to give a 1:1 mixture of 6-bromo and 6-methylthio-2-(2-phenylethyl) phenol. (1.29 g, 98%). Ms ($CI^+$): 2.5 $[M^+H]^+$ [6-SMe].

The mixture was alkylated using a similar method to that of Reference Example 1 and purified by chromatography (eluant: ethyl ether/hexane) to give methyl 4-(2-(2-phenethyl)-6-methylthio phenoxy-methyl)benzoate cleanly.

NMR (200 MH$_2$, DMSO-$d_6$): δ8.01 (d, 2H), 7.64 (d, 2H), 7.18 (m, 8H), 4.93 (s, 2H), 3.87 (s, 3H), 2.85 (bs, 4H), 2.42 (s, 3H).

Reference Example 28

Preparation of methyl 4-(6-amino-2-(2-phenethyl) phenoxy-methyl)benzoate

A solution of methyl 4-(6-nitro-2-(2-phenethyl)phenoxy-methyl)benzoate (1.5 g, 3.84 mmol) in ethyl acetate (20 ml) was treated with stannous chloride (4.34 g, 19.2 mmole). The reaction was heated to 70° C. for 5 hours, then allowed to cool to ambient temperature. The reaction mixture was partitioned between ethyl acetate/water and the organic phase dried ($MgSO_4$) and evaporated. The residue was purified by chromatography (eluant: ethyl acetate/hexane) to give the title product (0.946 g, 68%).

NMR (200 MH$_2$, DMSO-$d_6$): δ9.99 (dd, 2H), 7.64 (dd, 2H), 7.16 (m, 5R), 6.80 (t, 1H), 6.63 (dd, 1H), 6.50 (dd, 1H), 4.86 (s, 2H), 3.87 (s, 3H), 2.77 (bs, 4H)

Reference Example 29

Preparation of 6-isopropyl-2-(phenethyl)phenol

A solution of 2-hydroxy-3-isopropylbenzoic acid (5 g, 27.8 mmol) in acetone (40 ml) was treated with $K_2CO_3$ (7.67 g, 55.6 mmol) and benzyl bromide (9.98 g; 58.4 mmol). The reaction was stirred at ambient temperature for 60 hours, then evaporated. The residue was partitioned between ethyl acetate/$H_2O$ and the organic phase dried ($MgSO_4$) and evaporated. The residue was purified by chromatography (eluant: ethyl acetate/hexane) to give benzyl 2-benzyloxy-3-isopropylbenzoate (6.52 g, 18.11 mmol, 65%)

NMR (200 MHz, DMSO-$d_6$): δ7.58 (m, 2H), 7.39 (m, 10H), 7.23 (t, 1H), 5.32 (s, 2H), 4.86 (s, 2H), 3.30 (m, 1H), 1.14 (d, 6H).

A solution of $LiAlH_4$ (1M in THF, 8.13 ml) was added to freshly distilled THF (10 ml) 10 ml. A solution of benzyl 2-benzyloxy-3-isopropylbenzoate (2.27 g, 6.31 mmole) in THF (10 ml) was added via a syringe to the $LiAlH_4$ solution. The temperature was maintain below 40° C. using a water bath and the reaction mixture stirred at ambient temperature overnight. The reaction was quenched with water and the pH adjusted to ~7 with dilute HCl. The resultant precipitate was filtered off and the filtrate partitioned between ethyl acetate/$H_2O$. The organic phase was dried ($MgSO_4$), evaporated and the residue purified by chromatography (eluant: ethyl acetate/hexane) to give 2-benzyloxy-3-isopropylbenzylalcohol (1.38 g, 83%).

NMR (200 MHz, DMSO-$d_6$): δ7.29 (m, 8H), 4.82 (s, 2H), 4.58 (s, 2H), 3.30 (m, 1H), 1.17 (d, 6H).

A solution of 2-benzyloxy-3-isopropylbenzyl alcohol (1.26 g, 4.9 mmoles) in chloroform (50 ml) was heated with manganese dioxide (1.92 g, 22 mmole). The reaction was stirred at ambient temperature overnight, filtered and evaporated. The residue was purified by chromatography (eluant: ethyl acetate/hexane) to give 2-benzyloxy-2-isoproplybenzaldehyde, (0.71 g, 57%).

A suspension of benzyl triphenylphosphonium bromide (1.43 g, 3.3 mmol) in THF (20 ml) was treated with $LiN(SiMe_3)_2$ [1M in THF, 3.3 ml). The reaction was stirred at ambient temperature for 30 minutes. A solution of 2-benzyl-3-isopropyl benzaldehyde (0.56 g, 2.2 mmole) in THF (10 ml) was added and the reaction was stirred at ambient temperature for 48 hours. The reaction was partitioned between ethyl acetate/$H_2O$ and the organic phase washed well with $H_2O$, dried ($MgSO_4$) and evaporated. The residue was purified by chromatography to give 2-benzyloxy-1-isopropyl-3-(2-phenethenyl)benzene (0.52 g, 72%).

NMR (200 MHz, DMSO-$d_6$): (mixture of cis trans isomers) δ7.7 to 6.6 (complex multiplets, 15H), 4.90 and 4.85 (two singlets together 2H 3.32 (m, 1H), 1.16 (m, 6H).

A solution of 2-benzyloxy-1-isopropyl-3-(2-phenethenyl)-benzene, (0.46 g, 1.4 mmol) in ethanol 30 ml was treated with 10% palladium carbon [0.10 g]. The reaction was placed under a hydrogen atmosphere and stirred vigorously until the uptake of hydrogen ceased. The reaction was filtered through Celite and evaporated to give 2-(2-phenethyl)-6-isopropylphenol (0.34 g, quantitative).

NMR (200 MHz, DMSO-$d_6$): δ8.1 (s, 1H), 7.23 (m, 5H), 6.99 (dd, 1H), 6.91 (t, 1H), 3.31 (m, 1H), 2.63 (bs, 1H), 1.16 (d, 6H).

Reference Example 30

Preparation of 2-(2-phenethyl)-6-phenylphenol

Methanol (50 ml) was treated with concentrated sulphuric acid (4.9 g, 2.66 ml) cautiously. 2-Hydroxy-3-phenylbenzoic acid (10.7 g, 50 mmol) was added and the reaction mixture stirred at ambient temperature for 18 hours. The mixture was then heated at reflux for 4 hours, cooled to ambient temperature and evaporated. The residue was partitioned between ethyl acetate/and water, the organic layer washed twice with water, dried (MgSO$_4$) and evaporated to give methyl 2-hydroxy-3-phenylbenzoate.

A solution of methyl 2-hydroxy-3-phenylbenzoate (9.5 g, 41.7 mmol) in DMF (80 ml) was treated with K$_2$CO$_3$ (8.6 g, 62.5 mmole) and benzyl bromide (10.6 g 62.2 mmol). The reaction was stirred at ambient temperature overnight, then partitioned between ethyl acetate/and water. The organic phase was washed well with water, dried (MgSO$_4$) and evaporated. The residue was purified by chromatography (eluant: ethyl acetate/hexane) to give methyl 2-benzyloxy-3-phenylbenzoate (11.23 g, 8.5%).

NMR (250 MHz, DMSO-$d_6$): δ7.72 (dd, 1H), 7.65–7.07 (complex multiplets, 10H), 7.06 (m, 2H), 4.53 (s, 2H) 3.82 (s, 3H)

This was reduced with LiAlH$_4$ using a similar method to that of Reference example 29 to give 2-benzyloxy-3-phenylbenzyl alcohol.

2-Benzyloxy-3-phenylbenzyl alcohol was oxidised with manganese dioxide using a similar method to that described in Reference Example 29 to give 2-benzyloxy-3-phenylbenzaldehyde.

2-Benzyloxy-3-phenylbenzaldehyde was reacted with benzyl triphenylphosphonium bromide using a similar method to that of Example 48 to give 2-benzyloxy-1-phenyl-3-styrylbenzene, which was hydrogenated using a similar method to that of Reference Example 29 to give 2-(2-phenethyl)-6-pherylphenol.

Reference Example 31

Preparation of 6-hexyl-2-(2-phenethyl)phenol

To a stirred suspension of pentyl triphenylphosphonium bromide (10.4 g, 25.2 mM) in freshly distilled THF (40 ml) was added LiN(SiMe$_3$)$_2$ (1M in THF, 50 ml). The reaction was stirred at ambient temperature for 1 hour. Salicylaldehyde (2.8 g, 22.9 mM) was added to the reaction mixture which was stirred at ambient temperature for 60 hours. The reaction was then treated with water, the pH adjusted with 1N aqueous HCl to pH7 and extracted twice with ethyl acetate. The organic layers were combined, dried over (MgSO$_4$) and evaporated. The residue was purified by chromatography to give 2-(1-hexenyl)phenol, (3.57 g, 88%).

NMR (200 MHz, DMSO-$d_6$): δ9.40 (bs, 1H), δ7.32 (dd, 1H), 7.0 (m, 1H), 6.72 (m, 3H), 6.19 (m, 1H), 2.18 (m, 2H), 1.38 (m, 4H), 0.90 (m, 3H).

To a stirred solution of Mg(OMe)$_2$ (8% by weight in methanol 16.88 ml, 12.76 mM) was added 2-(1-hexenyl) phenol (3.44 g, 19.5 mmol) in toluene (18 ml). The reaction mixture was warmed to reflux and held at reflux for 2 hours. Toluene (18 ml) was added and the solvent distilled off until the reaction temperature rose to 93° C. A slurry of paraformaldehyde (1.8 g, 60 mmol) in toluene (18 ml) was added and the reaction heated at reflux for 3 hours. The reaction was allowed to cool to ambient temperature and stirred overnight. The reaction was diluted with toluene (20 ml) and washed with 2M aqueous H$_2$SO$_4$ (20 ml). The organic phase was washed with water until the aqueous phase was neutral in pH, dried (MgSO$_4$) and evaporated. The residue was purified by chromatography (eluant: ethyl ether/hexane) to give 3-(1-hexenyl)-2-hydroxybenzaldehyde (2.32 g, 58%).

NMR (200 MHz, DMSO-$d_6$): δ11.35 (s, 1H), 10.02 (s, 1H), 7.77 (d, 1H), 7.65 (dd, 1H), 7.04 (t, 1H), 6.67–6.3 (m, 2H), 2.21 (m, 2H), 1.4 (m, 4H) , 0.90 (t, 3H)

To a suspension of benzyltriphenylphosphonium bromide (5.25 g, 12.12 mmol) in THF (30 ml) was added LiN (SiMe$_3$)$_2$ [1N in THF, 24.26 ml]. The reaction was stirred at ambient temperature for 30 minutes and a solution of 3-(1-hexenyl)-2-hydroxybenzaldehyde (2.25 g, 11.03 mmol) in THF (5 ml) added. The reaction was stirred at ambient temperature for 60 hours, then quenched with water. The pH of the aqueous layer was neutralised with HCl (1N) and the reaction mixture extracted twice with ethyl acetate. The combined organic phases were washed with water, dried (MgSO$_4$) and evaporated. The residue was purified by chromatography (eluant: ethyl ether/hexane) to give 2-(2-phenethenyl)-6-(1-hexenyl)phenol, (2.28 g, 74%).

NMR (200 MHz, DMSO-$d_6$): (mixture of cis and trans isomers). δ8.9 (bs, 1H), 7.83–6.05 (complex multiplets, 12H), 2.2 (m, 2H), 1.38 (m, 4H), 0.90 (m, 3H).

To a solution of 6-hexenyl-2-(2-phenethenyl)phenol (2.15 g, 7.73 mmol) in ethanol (30 ml) was added 10% palladium on carbon (0.2 g). The reaction was placed under an atmosphere of hydrogen and stirred at ambient temperature for 18 hours. The reaction mixture was then filtered through Celite and evaporated. The residue was purified by chromatography to give 6-hexyl-2-(2-phenethyl)phenol (1.66 g, 7%).

NMR (200 MHz, DMSO-$d_6$): δ8.1 (s, 1H, 7.2(m, 5H), 6.9 (d, 2H), 6.66 (t, 1H), 2.53 (m, 4H), 1.63–0.75 (broad multiplets, 13H).

Reference Example 32

Preparation of methyl 4-(6-benzene-2-(2-phenethyl)-sulphonamidophenoxymethyl)benzoate A stirred solution of methyl 4-(6-amino-2-(2-phenethyl)-phenoxymethyl)benzoate (0.553 g, 1.53 mmol) in dichloromethane (5 ml) was treated with pyridine (0.36 g, 4.58 mmol) and benzenesulphonyl chloride (0.346 g, 1.97 mmol). The reaction was stirred at ambient temperature overnight then partitioned between dichloromethane and water. The organic layer was washed well with water, dried (Mgso$_4$) and evaporated. The residue was purified by chromatography (eluant: ethyl ether/hexane) to give the title product (0.53 g, 69%). NMR (200 MHz, DMSO-$d_6$): δ9.76 (bs, 1H) 7.97 (d, 2H), 7.78 (m, 2H), 7.57 (m, 5H), 7.05 (m, 8H), 4.68 (s, 2H), 3.88 (s, 3H), 2.71 (s, 4H).

Reference Example 33

Preparation of 2-hydroxy-3-(2-phenethyl) benzaldehyde

To a stirred solution of Mg(OMe)$_2$ [8% weight in methanol, 21.9 ml 16.47 mM) was added, over 5 minutes, a solution of 2-(2-phenethyl)phenol [5.0 g, 25.25 mM] in toluene (7 ml). The reaction was then heated to reflux and held at reflux for 1 hour (64° C.), then toluene (23 ml) was added and the solvent distilled off until the reaction temperature reached 93° C. A suspension of paraformaldehyde (2.35 g, 78.3 mM) in toluene (15 ml) was then added over 10 minutes keeping the reaction temperature at 86° C. The reaction was heated at reflux for 3 hours, then allowed to cool to ambient temperature and to stand for 18 hours. The reaction was diluted with toluene (28 ml) and washed with 2M aqueous $H_2SO_4$ (27 ml). The organic phase was washed with water until a neutral pH was achieved. After drying ($MgSO_4$) the solution was evaporated and the residue purified by chromatography (eluant: ethyl ether/hexane) to give the title product (3.11 g, 54%).

NMR (200 MHz, DMSO-$d_6$): δ11.15 (bs, 1H), 10.03 (s, 1H), 7.63 (dd, 2H), 7.44 (dd, 2H), 7.23 (m, 5H), 6.98 (t, 1H), 2.88 (m, 9H).

Reference Example 34

Preparation of methyl 4-(6-acetyl-2-(2-phenethyl)-phenoxymethyl)benzoate

A solution of 2-hydroxy-3-(2-phenethyl)benzaldehyde (1.0 g, 4.4 mmol) in THF (30 ml) was cooled to −78° C. under argon. Methyl lithium (1.4M in ethyl ether, 6.6 ml, 9.2 mmol) was added dropwise keeping the temperature below −60° and the reaction mixture stirred at −70° C. for 1 hour. The reaction was allowed to warm to 0° C. and quenched with water, the pH of the mixture was adjusted to neutral with HOAc and it was extracted with ethyl acetate. The organic phase was dried ($MgSO_4$) and evaporated. The resulting 6-(1-hydroxyethyl)-2-(2-phenethyl)phenol was used in the subsequent step (1.1 g quantitative) without further purification.

NMR (250 MHz, DMSO-$d_6$): δ8.9 (s, 1H), 7.25 (m, 6H), 7.0 (m, 2H), 6.7 (t, 1H), 5.94 (bs, 1H), 5.03 (q, 1H), 2.84 (bs, 4H), 1.87 (d, 3H).

A solution of the above hydroxy phenol (0.525 g, 2.17 mmol) in DMF (10 ml) was treated with potassium carbonate (0.6 g, 4.35 mmol) and methyl 4-bromomethyl benzoate (0.596 g, 2.6 mmol). The reaction was stirred at ambient temperature overnight, then partitioned between ethyl acetate and water. The organic phase was washed well with water (4x), brine, dried ($MgSO_4$) and evaporated. The residue was purified by chromatography (eluant: ethyl ether/hexane) to give methyl 4-(6-(1-hydroxyethyl)-2-(2-phenethyl)-phenoxymethyl)benzoate (0.486 g, 57%).

NMR (250 MHz, DMSO-$d_6$): δ8.04 (d, 2H), 7.62 (d, 2H), 7.38 (dd, 1H), 7.14 (m, 7H), 5.05 (q, 1H), 4,9 (q, 2H), 3.89 (s, 3H), 2.85 (bs, 4H), 1.33 (d, 3H).

A solution of the alcohol from above (0.441 g, 1.13 mmol) in chloroform (10 ml) was treated with manganese dioxide (0.92 g, 10.6 mmol). The reaction was stirred at ambient temperature for 4 hours, then heated to 40° C. and held at 40° C. for 48 hours. The reaction mixture was filtered through Celite and evaporated. The residue was purified by chromatography (eluant: ethyl ether/hexane) to give methyl 4-(6-acetyl-2-(2-phenethyl)phenoxymethyl)benzoate: (0.268 g, 65%).

NMR (250 MHz, DMSO-$d_6$: δ7.99 (d, 2H), 7.57 (d, 2H), 7.5 (d, 2H), 7.15 (m, 6H), 4.4 (s, 2H), 3.87 (s, 3H), 2.85 (m, 4H), 2.54 (s, 3H).

Reference Example 35

Preparation of methyl 4-(6-(N-diethylamino)-2-(2-phenethyl)phenoxymethyl)benzoate A stirred solution of methyl 4-(6-amino-(2-(2-phenethyl)-phenoxymethyl)benzoate (0.52 g, 1.44 mmol) in DMF (10 ml) was treated with $K_2CO_3$ (0.795 g, 5.76 mmol) and ethyl iodide (1.79 g, 11.5 mmol). The reaction was heated to 40° C. and stirred at 40° C. for 4 hours, then allowed to cool to ambient temperature and stirred for 18 hours. The reaction was filtered and partitioned between ethyl acetate/$H_2O$. The organic phase washed with water (4x), dried ($MgSO_4$) and evaporated. The residue was purified by chromatography (eluant: ethyl ether/hexane) to give the title product.

NMR (200 MHz, DMSO-$d_6$): δ7.98 (d, 2H), 7.57 (d, 2H), 7.05 (m, 8H), 5.04 (s, 2H), 3.87 (s, 3H), 3.14 (q, 4H), 2.78 (s, 4H), 0.96 (t, 6H).

Reference Example 36

Preparation of methyl 2-hydroxy-3-(2-phenethyl) benzoate

A stirred suspension of washed sodium hydride (0.875 g, 60%, 21.87 mmol) in THF (30 ml) was treated with a solution of 6-bromo-2-(2-phenethyl)phenol (5.5 g, 19.8 mmol) in THF (20 ml). The reaction was stirred at ambient temperature for 30 minutes then cooled to −70° C. A solution of n-butyl lithium (1.6M, 26 ml, 41.6 mmol) was added, keeping the temperature below −60° C., and the reaction was stirred at −70° C. for 1 hour. The reaction was poured onto excess crushed $CO_2$ in THF and allowed to warm to ambient temperature overnight. The mixture was acidified with aqueous HCl and extracted with ethyl acetate. The organic phase was dried ($MgSO_4$) and evaporated and the residue purified by chromatography (eluant: methanol/$CH_2Cl_2$) to give 2-hydroxy-3-(2-phenethyl)benzoic acid (4.29 g, 89%).

NMR (200 MHz, DMSO-$d_6$): δ7.64 (dd, 1H), 7.2 (m, 6H), 6.63 (t, 1H), 2.64 (s, 4H).

A solution of 2-hydroxy-3-(2-phenethyl)benzoic acid (4.43 g, 18.3 mmol) in methanol (50 ml) was treated with concentrated $H_2SO_4$ (4 ml). The reaction was heated to reflux on a steam bath and held at reflux for 18 hours, then allowed to cool to ambient temperature and the solvent evaporated. The residue was purified by chromatography (eluant: ethyl ether/hexane) to give the title product (2.94 g, 63%).

NMR (250 MHz, DMSO-$d_6$): δ10.96 (bs, 1H), 7.66 (dd, 1H), 7.36 (dd, 1H), 7.24 (m, 5H), 6.84 (t, 1H), 3.91 (s, 3H), 2.87 (bs, 4H).

Reference Example 37

Preparation of tert-butyl 4-(6-cyanomethyl-2-(2-phenethyl)-phenoxymethyl)benzoate To a stirred solution of tert-butyl 4-(6-formyl-2-(2-phenethyl)phenoxymethyl)benzoate (6.32 g, 16.9 mmol) in ethanol (100 ml) was added portionwise $NaBH_4$ (0.879 g, 23.25 mmol). The reaction mixture became faintly pink. The temperature of the mixture was kept below 30° C. and stirred at ambient temperature for 1.5 hours. The solvent was evaporated and ethyl acetate added to the residue. This solution was added dropwise to a stirred solution of further 1N aqueous HCl (70 ml) and water (50 ml). The organic phase was washed with water, saturated aqueous sodium hydrogen carbonate and brine, dried ($MgSO_4$) and evaporated. The residue containing tert-butyl 4-(6-hydroxymethyl-(2-(2-phenethyl)phenoxymethyl)benzoate was used without further purification in the subsequent step (6.15 g, 87%).

NMR (250 MHz, DMSO-$d_6$): δ7.95 (d, 2H), 7.59 (d, 2H), 7.18 (m, 8H), 5.05 (t, 1H), 4.9 (s, 2H), 4.57 (d, 2H), 2.83 (s, 4H), 1.58 (s, 9H).

A solution of tert-butyl 4-(6-hydroxymethyl-2-(2-phenethyl)-phenoxymethyl)benzoate (0.711 g, 1.7 mmol) in dichloromethane (20 ml) was cooled to 0° C. Tetrabromomethane (0.694 g, 2.09 mmol) and triphenylphosphine-polymer bound (1.11 g, 3 mmol/g, 3.33 mmol) were added and the reaction was allowed to stir at 0° C. for 1 hour and then allowed to warm to ambient temperature. The reaction was stirred at ambient temperature for 30 minutes then filtered and evaporated. The residue containing tert-butyl 4-(6-bromomethyl-2-(phenethyl)-phenoxymethyl)benzoate was used without purification in the subsequent steps (0.82 g, quantitative).

NMR (200 MHz, DMSO-d$_6$): δ7.95 (d, 2H), 7.62 (d, 2H), 7.23 (m, 8H), 5.03 (s, 2H), 4.7 (s, 2H), 2.87 (s, 4H), 1.57 (s, 9H).

A solution of the containing tert-butyl 4-(6-bromomethyl-2-(2-phenethyl)phenoxymethyl)benzoate (0.82 g, 1.71 mmol) in DMSO (20 ml) was treated with NaCN (0.208 g, 4.24 mmol). The reaction was heated to 100° C. for 10 minutes. The reaction mixture was partitioned between ethyl ether and water and the organic phase evaporated. The residue was purified by chromatography (eluant: ethyl ether/hexane) to give the title product (0.277, 38%). NMR (250 MHz, DMSO-d$_6$): δ7.95 (d, 2H), 7.61 (d, 2H), 7.19 (m, 8H), 4.93 (s, 2H), 4.00 (s, 2H), 2.87 (s, 4H), 1.57 (s, 9H).

Reference Example 38

Preparation of tert-butyl 4-(6-methoxymethyl-2-(phenethyl)-phenoxymethyl)benzoate Sodium hydride (0.1 g, 2.27 mmol) was washed with hexane (2x) and then suspended in THF (10 ml). tert-Butyl 4-(6-hydroxymethyl-2-(2-phenethyl)-phenoxymethyl)benzoate was added to this suspension (0.816 g, 1.95 mmol) as a solution in THF (5 ml). The reaction was stirred at ambient temperature for 30 minutes (until effervescence ceased). Methyl iodide (0.55 g, 3.87 mmol) was then added and the reaction stirred at ambient temperature for 1½ hours. The organic phase was dried (MgSo$_4$) and evaporated and the residue purified by chromatography (eluant: ethyl ether/hexane) to give the title product.

NMR (250 MHz, DMSO-d$_6$): δ7.95 (d, 2H), 7.58 (d, 2H), 7.18 (m, 8H), 4.92 (s, 2H), 4.46 (s, 2H), 3.3 (s, 3H), 2.85 (s, 4H), 1.57 (s, 9H).

Reference Example 39

Preparation of methyl 4-(2-(2-phenethyl)-4-phenylthiomethylphenoxymethyl)benzoate Methyl 4-(4-hydroxymethyl-2-(2-phenethyl)phenoxymethyl)benzoate (0.5 g, 1.33 mmol) was dissolved in pyridine (3 ml), cooled to 0° C. (under argon) and treated with PhSSPh (0.87 g, 4 mmol) and tributyl phosphine (0.8 g, 4 mmol). The mixture was allowed to warm to ambient temperature and stirred at ambient temperature overnight. The reaction was partitioned between ethyl ether and water and the etherial layer washed with water (2x), 1N HCl (2x), and brine (1x). The organic phase was dried (MgSO$_4$) and evaporated. The residue was purified by chromatography (eluant: ethyl ether/hexane) to give the title product as a white solid (0.43 g).

NMR (250 MHz, DMSO-d$_6$): δ8.0 (d, 2H), 7.59 (d, 2H), 7.15 (m, 10H), 5.19 (s, 2H), 4.15 (s, 2H), 3.88 (s, 3H), 2.8 (m, 4H).

Reference Example 40

The compounds of Table XXIV were prepared using a similar method to that of Reference Example 39.

TABLE XXIV

R—[phenyl]—OCH$_2$—[phenyl]—COOR'
with CH$_2$CH$_2$Ph substituent

| Compound No. | R | R$^1$ | MS |
|---|---|---|---|
| 1 | —CH$_2$SPh | t-butyl | |
| 2 | —CH$_2$SMe | t-butyl | FAB$^+$: 468 (M + H)$^+$ |

Reference Example 41

Not used.

Reference Example 42

Preparation of 4-hydroxymethyl-2-(2-phenethyl)phenol a) A solution of the ethyl 4-benzyloxy-3-(2-phenethenyl)benzoate, preparation described in Reference example 44 parts a)–d), (2.6 g, 7.25 mmol) in ethanol (40 ml) was treated with 10% palladium on carbon (0.25 g). The reaction was placed under an atmosphere of hydrogen and stirred at ambient temperature until the uptake of hydrogen ceased. The reaction was filtered through Celite and evaporated to give ethyl 4-hydroxy-3-(2-phenethyl)benzoate as a colourless gum (2.2 g, 84%).

NMR (250 MHz, DMSO-d$_6$): δ10.21 (brs, 1H), 7.7–7.1 (complex multiplets, together 7H), 6.89 (m, 1H), 4.24 (q, 2H), 2.84 (s, 4H), 1.28 (t, 3H).

b) To a stirred suspension of LiAlH4 (0.93 g, 24.4 mmol) in freshly distilled THF (70 ml) under argon was added dropwise ethyl 4-hydroxy-3-(2-phenethyl)benzoate (4.4 g, 12.1 mmol) as a solution in THP (25 ml). Once the addition was complete the reaction was stirred at ambient temperature for four hours. Water was added to decompose the excess LiAlH$_4$ and the pH was adjusted to pH1–2 by the addition of 1N aqueous HCl. The reaction mixture was extracted with ethyl acetate (2x). The combined extracts were washed with brine, dried (MgSO$_4$) and evaporated. The residue was purified by chromatography (eluant: ethyl acetate/hexane) to give the title product as a colourless solid (1.25 g, 45%).

NMR (200 MHz, CDCl$_3$): δ7.18 (m, 7H), 6.72 (m, 1H), 4.68 (s, 1H), 4.57 (m, 2H), 2.91 (s, 4H)

Reference Example 43

Preparation of methyl 4-(4-cyanomethyl-2-(2-phenethyl)phenoxymethyl)benzoate

To a stirred solution of the methyl 4-(4-hydroxymethyl-2-(2-phenethyl)phenoxymethyl)benzoate (0.5 g, 1,33 mmol) in dry CH$_2$Cl$_2$ (16 ml) at 0° C. under argon was added tetrabromomethane (0.543 g, 1.64 mmol) followed by triphenylphosphine polymer bound (3 mmol/g) (0.89 g, 266 mmol). The reaction was stirred at 0° C. for 1 hour, allowed to warm to ambient temperature and stirred for 1 hour. The reaction mixture was filtered to remove the polymer and evaporated to give methyl 4-(4-bromomethyl-2-(2-phenethyl)phenoxymethyl)benzoate which was used without further purification.

NMR (250 MHz, DMSO-d$_6$): δ8.00 (m, 2H), 7.6 (m, 2H), 7.2 (m, 6H), 5.4 (s, 2H), 4.65 (s, 2H), 3.87 (s, 3H), 2.9 (m, 4H).

To a solution of the above methyl 4-(4-bromomethyl-2-(2-phenethyl)phenoxymethyl)benzoate (1.33 mmol, 0.58 g) in DMSO (15 ml) was added sodium cyanide (0.163 g, 3.32 mmol). The reaction was stirred at ambient temperature for 2 hours and then allowed to stand overnight. The reaction mixture was partitioned between ethyl ester and water and the aqueous layer was washed with ethyl ether (2×). The combined etherial extracts were washed with brine, dried (MgSO$_4$) and evaporated. The residue was purified by chromatography to give the title product as an off-white solid (0.2 g, 38%).

NMR (200 MHz, DMSO-d$_6$): δ8.0 (d, 2H), 7.60 (d, 2H), 7.17 (m, 8H), 5.23 (s, 2H), 3.89 (s, 2H), 3.66 (s, 3H), 2.66 (bs, 4H).

Reference Example 44

Preparation of 4-(N-diethylcarbamoyl)-2-(2-phenethyl)phenol

A solution of 5-bromo-2-benzyloxybenzaldehyde, prepared from commercial 5-bromosalicylicaldehyde by benzylation according to the method given in Reference example 22a), (25 g, 74.6 mmol) in toluene (250 ml) was treated with ethylene glycol (5 ml), and p-toluenesulfonic acid (0.24 g). The reaction was heated to reflux with azeotropic removal of water (Dean Stark trap). After 2.5 hrs, no further water was collected. The reaction was cooled to ambient temperature and washed with saturated aqueous NaHCO3, dried (MgSO$_4$ and evaporated to give 2-(2-benzyloxy-5-bromophenyl)-1,3-dioxolane as a pale orange solid (26.8 g). This material was used without purification.

NMr (200 MHz, DMSO-d$_6$): 7.42 (m, 7H), 7.08 (m, 1H), 6.03 (s, 1H), 5.18 (s, 2H), 3.98 (m, 4H)

b) A solution of 2-(2-benzyloxy-5-bromophenyl)-1,3-dioxolane (7.8 g, 23.2 mmol) in freshly distilled THF (160 ml) was cooled to −75° C. with stirring under an argon atmosphere. To this solution was added n-butyl lithium (25.6 ml, 1.6 M in hexane) keeping the temperature below −70° C. The reaction mixture was stirred at −70° C. for 1 hour. The reaction was allowed to warm to −60° C. and added to a cooled (−60° C.) solution of ethyl chloroformate (5.05 g, 46.5 mmol) in freshly distilled THF (70 ml). The reaction was allowed to warm to ambient temperature and stirred overnight. The reaction mixture was diluted with ethyl ether (100 ml), washed with ice/water (1×50 ml), saturated aqueous NaHCO3 (1×35 ml), brine (1×35 ml) dried over MgSO4 and evaporated. The product was purified by chromatography (eluant: ethyl ether/hexane) to give 2-(2-benzyloxy-5-ethoxycarbonylphenyl)-1,3-dioxolane as a colourless gum (4.2 g, 55%).

NMR (200 MHz, DMSO-d6): δ8.03 (d, 1H), 7.94 (dd, 1H), 7.42 (m, 6H), 6.05 (s, 1H), 5.25 (s, 2H), 4.29 (q, 2H), 4.0 (m, 4H), 1.30 (t, 3H).

c) A solution of the above dioxolane (1.0 g, 3.05 mmol) in ethanol (5 ml) and THF (5 ml) was treated with 2N aqueous HCl (3 ml). The reaction was allowed to stand at ambient temperature overnight then evaporated to low bulk, treated with ice, water and extracted with ethyl acetate (2×). The combined organic extracts were washed with water, saturated aqueous sodium bicarbonate and brine, dried (MgSO$_4$) and evaporated to give ethyl 4-benzyloxy-2-formylbenzoate as a colourless gum (0.88 g). This material was used in the subsequent step without further purification.

NMR (200 MHz, DMSO-d$_6$): δ10.40 (s, 1H), 8.23 (m, 2H), 7.44 (m, 6H), 5.4 (s, 2H), 4.32 (q, 2H), 1.32 (t, 3H).

d) A suspension of benzyl triphenylphosphonium bromide (1.34 g, 31. mmol) in freshly distilled THF (15 ml) was treated with LiN(SiMe$_3$)$_2$ (1N in THF, 3.7 ml). After stirring for 45 minutes at ambient temperature the red solution was treated with a solution of ethyl 4-benzyloxy-2-formylbenzoate (0.88 g, 31. mmol) THF (3 ml). The reaction was stirred at ambient temperature for 24 hours, then partitioned between ethyl ether and water. The combined etherial extracts were washed with brine, dried (MgSO4) and evaporated. The residue was purified by chromatography (eluant: ethyl ether/hexane) to ethyl 4-benzyloxy-3-(2-phenethenyl)benzoate as a colourless gum (0.57

NMR (200 MHz, DMSO-d6): (mixture of cis and trans isomers) δ8.3–6.6 (series of complex multiplet taken together 15H), 5.32 and 5.22 (two singlets, together 2H), 4.3 and 4.15 (two quartets, together 2H), 1.34 and 1.19 (two triplets, together 3H).

e) A solution of the above ester (0.57 g, 1.6 mmol) in ethanol (8 ml) and THF (8 ml) was treated with 1N aqueous NaOH (3.5 ml) and allowed to stand at ambient temperature overnight. The reaction was partially evaporated, diluted with water, acidified with acetic acid and extracted with ethyl acetate (2×). The combined extracts were dried (MgSO4) and evaporated to give 4-benzyloxy-3-(2-phenethenyl)benzoic acid as a white solid (0.47 g).

f) A suspension of the above acid (0.47 g, 1.4 mmol) in dry CH$_2$Cl$_2$ (10 ml) was treated with oxalyl chloride (0.23 g, 1.77 mmol) and 3 drops of DMF. The reaction was stirred at ambient temperature for 3.5 hours then the solvent was evaporated to dryness, the residue taken up in dry CH$_2$Cl$_2$ and the solvent evaporated a second time. Finally the acid chloride was dissolved in dry CH$_2$Cl$_2$ (5 ml). The resultant solution of acid chloride was added to a solution of diethylamine (0.113 g, 1.54 mmol) and triethylamine (0.424 g, 4.2 mmol) in dry CH$_2$Cl$_2$ (5 ml) at ambient temperature. The reaction mixture was allowed to stand at ambient temperature overnight and then the solvent was evaporated. The residue was purified by chromatography (eluant: ethyl ether/hexane HOAc) to give N,N-diethyl-4-benzyloxy-3-(2-phenethenyl)benzamide as a colourless gum (0.3 g, 56%).

NMR (250 MHz, DMSO-d6): (mixture of cis, trans) δ67.7–6.6 (complex multiplets, together 15H), 5.26 and 5.2 (2 singlets, together 2H), 3.2 (broad multiplet, partially obscured by H$_2$O), 1.13 (broad triplet) and 0.92 (broad singlet) (together 6H).

g) A solution of the above amide (0.3 g, 0.78 mmol) in ethanol (10 ml) was treated with 10% palladium on carbon (0.03 g). The reaction mixture was placed under a hydrogen atmosphere, stirred until the uptake of hydrogen ceased, filtered and evaporated to give 4-(N-diethylcarbamoyl)-2-(2-phenethyl)phenol as a colourless gum (0.227 g, 98%).

NMR (200 MHz, DMSO-d6): δ9.71 (broad s, 1H), 7.42–7.08 (m, 5H), 7.00 (m, 2H), 6.82 (d, 1H), 3.25 (m, partially obscured by H$_2$O), 2.83 (s, 4H), 1.05 (m, 6H)

Reference Example 45

Preparation of methyl 4-(4-hydroxyimino-2-(2-phenethyl)phenoxymethyl)benzoate

Methyl 4-(4-formyl-2-(2-phenethyl)phenoxymethyl)benzoate (0.18 g, 0.48 mMol) was dissolved in ethanol (3 ml) and treated with hydroxylamine hydrochloride (0.040 g, 0.57 mMol) and pyridine (0.1 ml). The reaction mixture was refluxed on a steam bath for 3 hours, then allowed to cool to ambient temperature. The resulting precipitate was dissolved in ethyl ether and the organic solution washed with 2N aqueous HCl (2x), water (1x) and brine (1x). The etherial layer was dried (MgSO4) and evaporated to give the title product as white solid (0.19 g, quantitative).

NMR D1065 (200 MHz, DMSO-d6): δ11.24 (s, 1H), 8.43 (s, 1H), 8.00 (d, J=8.3 Hz, 2H), 7.65 (m, 3H), 7.21 (m, 5H), 7.02 (m, 1H), 6.88 (m, 1H), 5.29 (s, 2H), 3.88 (s, 3H), 3.01 (m, 2H), 2.85 (m, 2H).

Reference Example 46

The compounds of Table XXV were prepared using a similar method to that of Reference Example 45.

TABLE XXV

[Structure: benzene ring with positions 3,4,5,6 labeled, R at position 3, OCH$_2$-C$_6$H$_4$-COOMe group, and CH$_2$CH$_2$Ph group]

| Compound No. | R | MS |
|---|---|---|
| 1 | 4-C(=N—OH)CH$_3$ | |
| 2 | 6-C(=N—OH)H | (FAB$^+$): 390 (M + H)$^+$ |
| 3 | 6-C(=N—OH)CH$_3$ | (FAB$^+$): 404 (M + H)$^+$ |

Reference Example 47

Preparation of methyl 4-(4-methanesulphinyl-2-(2-phenethyl) phenoxymethyl)benzoate A solution of the methyl 4-(4-methylthio-2-(2-phenethyl) phenoxymethyl)benzoate (0.73 g, 1.79 mmol) in CH$_2$Cl$_2$(25 ml) was cooled to −10° C. To this solution was added portionwise 3-chloroperoxybenzoic acid (0.586 g, 55%, 1.86 mmol). The temperature of the reaction was maintained below 8° C. Once the addition of the peracid was complete (2 hours total reaction time) no starting material could be detected by TLC (ethyl ether/hexane). The reaction mixture was washed with saturated aqueous NaHCO3, dried (MgSO4) and evaporated. The crude product was purified by chromatography (eluant: ethyl acetate/ethyl ether) to give the title product as a white solid (0.55 g, 75%).

NMR (200 MHz, DMSO-d6) : δ8.01 (d, 2H) , 7.63 (d, 2H), 7.46 (m, 2H), 7.18 (m, 6H), 5.30 (s, 2H), 3.88 (s, 3H), 2.92 (m, 4H).

Reference Example 48

The compounds of Table XXVI were prepared from the appropriate thio compound using a similar method to that of Reference Example 47.

TABLE XXVI

[Structure: benzene ring with positions 3,4,5,6 labeled, R at position 3, OCH$_2$-C$_6$H$_4$-COOR' group, and CH$_2$CH$_2$Ph group]

| Compound No. | R | R$^1$ | MS |
|---|---|---|---|
| 1 | 6-SOMe | Me | (CI$^+$): 409 (M + H)$^+$ |
| 2 | 6-CH$_2$SOMe | tBu | (CI$^+$): 465 (M + H)$^+$ |

Reference Example 49

Preparation of methyl 4-(4-(methylsulphonyl-2-(2-phenethyl)phenoxymethyl)benzoate A solution of methyl 4-(4-methylthio-2-(2-phenethyl) phenoxymethyl) benzoate (0.77 g, 1.96 mMol) was cooled to 0° C. 3-Chloroperoxybenzoic acid (1.23 g, 55%, 3.92 mmol in 15 ml CH$_2$Cl$_2$ was added keeping the temperature below 2° C. The reaction was stirred for 30 minutes to 0° C. and then warmed to ambient temperature. The reaction mixture was stirred for 30 minutes at ambient temperature, then washed with saturated aqueous NaHCO$_3$ (2x), dried (MgSO$_4$) and evaporated. The crude product was purified by chromatography (eluant ethyl ether/hexane) to give the title product as a white solid (0.45 g, 54%).

NMR (200 MHz, DMSO-d6): δ8.01 (d, 2H), 7.67 (m, 4H), 7.22 (m, 6H), 5.36 (s, 2H), 3.87 (s, 3H), 3.08 (s, 3H), 2.92 (m,4H).

Reference Example 50

The compounds of Table XXVII were prepared from the appropriate thio compound using a similar method to that of Reference Example 49.

TABLE XXVII

[Structure: benzene ring with positions 3,4,5,6 labeled, R at position 3, OCH$_2$-C$_6$H$_4$-COOR' group, and CH$_2$CH$_2$Ph group]

| Compound No. | R | R$^1$ | MS |
|---|---|---|---|
| 1 | 6-CH$_2$SO$_2$CH$_3$ | tBu | (CI$^+$): 498 (M + NH$_4$)$^+$ |
| 2 | 6-CH$_2$SO$_2$Ph | tBu | (FAB$^+$): 565 (M + Na+) |

Reference Example 51

Preparation of 4-nitro-2-(2-phenethyl)phenol, 6-nitro-2- (2-phenethyl)phenol and 4,6-dinitro-2-(2-phenethyl)phenol Concentrated nitric acid (2.08 ml, 33 mMol] was added carefully to acetic anhydride (8.4 ml) at 0° C. The mixture was stirred at 0° C. for 15 minutes, then 2-(2-phenethyl) phenol (6.2 g, 31.3 mmol in 200 ml of acetic anhydride) was added at 0° C. Once the addition was complete the yellow solution was allowed to warm to ambient temperature and to stand overnight. The reaction mixture was concentrated at reduced pressure and the residue purified by chromatography (eluant: ethyl ether/hexane) to give 6-nitro-2-(2-phenethyl)phenol (A) (2.4 g) as a bright yellow solid. An orange/yellow solid (3.8 g) was also obtained. This was purified by chromatography (eluant: ethyl acetate/hexane) to give 4,6-dinitro-2-(2-phenethyl)phenol (B) (0.70 g) as an orange solid and 4-nitro-2-(2-phenethyl)phenol (C) (1.5 g)].

(A): NMR (200 MHz, DMSO-$d_6$): $\delta$10.54 (s, 1H), 7.86 (dd, J=1.6, 8.4 Hz, 1H), 7.49 (dd, J=1.6, 7.4 Hz, 1H), 7.25 (m, 5H), 6.95 (dd, J=8.4, 7.4 Hz, 1H)2.91 (m, 4H).

(B): NMR (200 MHz, DMSO-$d_6$): $\delta$8.61 (d, J=2.86 Hz, 1H), 8.27 (d, J=2.86 Hz, 1H), 7.23 (m, 5H), 3.04 (m, 2H), 2.89 (m, 2H).

(C): NMR (200 MHz, DMSO-$d_6$): $\delta$11.05 (bs, 1H), 8.00 (m, 2H), 7.25 (m, 5H), 6.97 (d, J=9.3 Hz, 1H), 2.88 (bs, 4H).

Reference Example 52

Preparation of 4-hexyl-2-(2-phenethyl)phenol

To a suspension of pentyl triphenylphosphonium bromide (4.76 g, 11.5 mMol) in freshly distilled THF (40 ml) was added LiN(SiMe3)$_2$ (1N in THF, 23 ml). The red solution was stirred at ambient temperature for 30 minutes then a solution of p-hydroxybenzaldehyde (1.06 g, 10 mMol) in THF (10 ml) added. The reaction was stirred at ambient temperature for 4 days, then partitioned between ethyl ether and dilute aqueous HCl (1N). The combined etherial extracts were washed with brine, dried (MgSO4) and evaporated. The crude oil was purified by chromatography (eluant: ethyl ether/hexane) to give 4-(1-hexenyl)phenol as a pale yellow solid (1.5 g, 85%).

NMR (200 MHz, DMSO-$d_6$) (mixture of cis and trans isomers): $\delta$9.33 (s, 1H), 7.14 (m, 2H), 6.70 (m, 2H), 6.26 (m, 1H), 6.1–5.35 (multiplets, together 1H), 2.35–2.08 (m, 2H), 1.36 (m, 4H), 0.89 (m, 3H). 4-(1-Hexenyl)phenol in toluene (8 ml) was added to Mg(OMe)$_2$ (7.3 ml, 8% wt/wt solution in methanol, 5.5 mMol) and the resultant red solution heated at reflux for 1 hour. The mixture was then distilled until the reaction temperature rose to 95° C. A suspension of paraformaldehyde (0.78 g, 26 mmol) in toluene (5 ml) was then added and the reaction heated at reflux for three hours. The reaction was allowed to cool to ambient temperature and to stir overnight. The reaction mixture was then diluted with toluene and washed with 2M aqueous H$_2$SO$_4$ (10 ml). The organic layer was washed with water (3×), dried (MgSO$_4$) and evaporated. The residue was purified by chromatography (eluant: ethyl ether/hexane) to give 5-(1-hexenyl)-2-hydroxybenzaldehyde as a yellow/green oil (0.65 g, 38%).

NMR (200 (MHz, DMSO-$d_6$): (mixture of cis and trans isomers): $\delta$10.74 (bs, 1H), 10.32 and 10.29 (2 singlets, together 1H), 7.66–7.44 (m, 2H), 7.02 (m, 1H), 6.5–6.33 (m, 1H), 6.3–5.6 (multiplets, together 1H), 2.24 (m, 2H), 1.43 (m, 4H), 0.95 (m, 3H).

To a suspension of benzyl triphenyl phosphonium bromide (4.0 g, 3.5 mmol) in freshly distilled THF (20 ml) was added as a solution of LiN(SiMe$_3$)$_2$ (1N, 7.0 ml). The red solution was stirred at ambient temperature for 45 minutes and then a solution of the aldehyde from above, (0.65 g, 3.2 mmol) in THF (8 ml) was added. The resultant reaction was stirred at ambient temperature for 4 days then treated with 1N aqueous HCl (10 ml) and extracted with ethyl ether (2×). The combined extracts were washed with brine, dried MgSO$_4$ and evaporated. The residue was purified by chromatography (eluant: ethyl ether/hexane) to give 4-(1-hexenyl)-2-(2-phenethyl)phenol as a pale yellow solid (0.5 g, 56%, mixture of cis and trans isomers of both olefins).

NMR (200 MHz, DMSO-$d_6$): $\delta$9.68 (bs, 1H), 7.55–5.40 (complex multiplets, 12H), 2.4–2.0 (m, 2H), 1.33 (m, 4H), 0.85 (m, 3H).

To a solution of 4-(1-hexenyl)-2-(2-phenethenyl) phenol (0.5 g, 1.8 mmol) in ethanol (40 ml) was added 10% palladium on carbon of (0.050 g). The reaction was placed under an atmosphere of hydrogen to stirred at STP until the uptake of hydrogen ceased. The reaction was filtered to remove catalyst. The filtrate was evaporated to leave a colourless oil which was used without purification (0.5 g, 99%).

NMR (250 MHz, DMSO-$d_6$): $\delta$8.96 (bs, 1H), 7.22 (m, 5H), 6.79 (m, 2H), 6.69 (d, 1H), 2.79 (m, 4H), 2.41 (bt, 2H), 1.47 (m, 2H), 1.26 (m, 6H), 0.86 (bt, 3H).

Reference Example 53

Preparation of 2-hydroxy-5-methylbenzaldehyde a) To a suspension of LiAlH$_4$ (2.5 g, 66 mmol) LiAlH$_4$ in freshly distilled THF (8 ml) at 0° C. under argon, was added dropwise with stirring a solution of 5-methylsalicylic acid (5 g, 33 mmol) in freshly distilled THF (80 ml). Addition was complete in 0.75 hours and the reaction stirred at ambient temperature overnight. Careful addition of water (5 ml) was followed by the addition of ice (10 ml) and concentrated HCl (1 ml). The solvent was decanted and the residue treated with ethyl ether and ice water. The pH of the mixture was adjusted to pH 1 with concentrated HCl and the organic layer combined with the decanted solvent, washed with brine, dried (MgSO$_4$) and evaporated. The residue was subjected to chromatography (eluant: ethyl ether/hexane) to give 2-hydroxymethyl-4-methylphenol as a white solid (3.1 g, 68%).

NMR: (200 MHz, DMSO-$d_6$): $\delta$8.96 (bs, 1H), 7.06 (bs, 1H), 6.82 (bd, 1H), 6.62 (d, 1H), 4.44 (s, 2H), 2.19 (s, 3H).

b) 2-Hydroxymethyl-4-methylphenol (3.1 g, 22.4 mMol) was dissolved in CHCl$_3$ (95 ml). The solution was treated with manganese dioxide (8.7 g, 100 mmol) and the reaction stirred at ambient temperature overnight under an argon atmosphere. The reaction was then filtered through Celite and the solvent evaporated. The residue was subjected to chromatography (eluant: ethyl ether/hexane) to give 2-hydroxy-5-methylbenzaldehyde as a pale green solid (0.63 g, 20.7%).

NMR (200 MHz, DMSO-$d_6$): $\delta$10.45 (s, 1H), 10.21 (s, 1H), 7.45 (bs, 1H), 7.33 (dd, 1H), 6.89 (d, 1H), 2.45 (s, 3H).

Reference Example 54

Preparation of 4-hydroxy-3-(2-phenethyl) benzaldehyde

A solution of 2-(2-phenethyl)phenol (5 g, 25.3 mmol) in dry dichloromethane (10 ml) under an argon atmosphere, at −5° C., was treated with a solution of TiCl$_4$ in CH$_2$Cl$_2$ (1N, 56.5 ml), maintaining the temperature below −3° C. (exothermic). To the deep red solution was added Cl$_2$CHOCH$_3$ (3.5 g, 30.4 mmol), again maintaining the temperature below −3° C. The reaction was allowed to warm to 0° C. and to stir for 1 hour, then the reaction was allowed to warm to ambient temperature and to stir for 2.5 hours. The nearly black reaction mixture was poured onto ice (25 g) and HCl (1 ml) and ethyl ether (50 ml) added. After stirring for 30 minutes the mixture was extracted with ethyl acetate (2×100 ml) and the combined extracts washed with brine, dried (MgSO$_4$) and evaporated. The residue was purified by chromatography (eluant: ethyl ether/hexane) to give the title product (0.18 g) as an off-white solid.

NMR (200 MHz, DMSO-d$_6$): δ10.27 (s, 1H), 9.34 (s, 1H), 7.81 (dd, 1H), 7.58 (dt, 1H), 7.38 (m, 2H), 6.98 (d, 2H), 6.78 (d, 1H), 6.67 (t, 1H), 3.25 (m, partially obscured by H$_2$O), 2.78 (m, 2H).

Reference Example 55

Preparation of 2-hydroxy-5-pivaloyloxy-benzaldehyde

To a cooled (−8° C.), stirred suspension of 2,5-dihydroxybenzaldehyde (13 g, 93.6 mmol) in of CH$_2$Cl$_2$ (65 ml) (dried over 4A sieves) (65 ml) was added triethylamine (6.5 ml, 46.8 mmol) to give a deep red solution. Pivaloyl chloride (5.6 g, 46.8 mmol) was added portionwise keeping the temperature below 0° C. After the addition was complete the reaction was allowed to warm to ambient temperature and stirred overnight. The reaction was washed with 2N aqueous HCl, water, saturated aqueous NaHCO3 and dried (MgSO$_4$). The organic solution was filtered and evaporated and the residue purified by chromatography (eluant: CH$_2$Cl$_2$/hexane) to give the title product as a colourless oil which crystallized on standing (4.7 g, 45% based on limiting reagent).

NMR (200 MHZ, DMSO-d$_6$): δ10.74 (bs, 1H), 10.25 (s, 1H), 7.27 (m, 2H), 7.02 (d, 1H), 1.29 (s, 9H).

Reference Example 56

Not used.

Reference Example 57

Preparation of tert-butyl 4-(4-N-methylcarbamoyl-2-(2-phenethyl)phenoxymethyl)benzoate A solution of the tert-butyl 4-(4-methoxycarbonyl-2-(2-phenethyl)phenoxymethyl)benzoate (1.12 g, 2.5 mmol) in THF (10 ml) and t-butanol (10 ml) was treated with 1N aqueous NaOH (10 ml). The reaction was stirred at ambient temperature for 60 hours, the solvent partially evaporated, diluted with water and acidified with acetic acid. The mixture was extracted with ethyl acetate (2×) and the combined extracts were washed with brine (2×), dried (MgSO$_4$) and evaporated to give tert-butyl 4-(4-carboxy-2-(2-phenethyl)phenoxymethyl)benzoate as a white solid (1.0 g, 93%).

NMR (250 MHz, DMSO-d$_6$): δ12.5 (very broad singlet, 1H), 7.95 (d, 2H), 7.78 (m, 2H), 7.6 (d, 2H), 7.15 (m, 6H), 5.3 (s, 2H), 2.88 (m, 4H), 1.55 (s, 9H).

A solution of tert-butyl 4-(4-carboxy-2-(2-phenethyl)-phenoxymethyl)benzoate as (1.0 g, 2.3 mmol) in freshly distilled THF (12 ml) was treated with n-methyl morpholine (0.23 g, 2.3 mmol). The solution was cooled to −20° C. under argon and isobutyl chloroformate (0.32 g, 2.3 mmol) added keeping the temperature below −20° C. The reaction was allowed to warm to −10° C. over 30 minutes, then to −35° C. and treated with methylamine in methanol (1.3 ml of 33% w/w solution, 10 mmol) keeping the temperature below −20° C. The reaction was then allowed to warm to ambient temperature, water was added and the reaction was extracted with ethyl ether (2×). The combined etherial extracts were washed with brine, dried (MgSO$_4$) and evaporated. The product was purified by chromatography (ethyl acetate/ethyl ether) to give the title product as a white solid (0.33 g, 32%).

NMR (200 MHz, DMSO-d$_6$): δ8.2 (bm, 1H), 7.93 (d, 2H), 7.63 (m, 4H), 7.2 (m, 6H), 5.27 (s, 2H), 2.88 (bs, 4H), 2.76 (d, 3H), 1.55 (s, 9H).

Reference Example 58

Preparation of methyl 4-hydroxy-3-(2-phenethyl)benzoate

A suspension of 3-formyl-4-hydroxybenzoic acid (3.9 g, 23.5 mmol) in of methanol (50 ml) was cooled below 0° C. To the suspension was added concentrated H$_2$SO$_4$ (3 ml) and the reaction was allowed to warm to ambient temperature and stirred for 60 hours. The reaction was heated to reflux for 12 hours, the solvent evaporated and residue subjected to chromatography (eluant: ethyl ether/hexane) to give methyl 3-formyl-4-hydroxybenzoate as a white solid (3.55 g, 84%).

NMR (200 MHz, DMSO-d$_6$): δ11.53 (s, 1H), 10.30 (s, 1H), 8.25 (d, 1H), 8.06 (dd, lH), 7.10 (d, 1H), 3.84 (s, 3H).

To a solution of methyl 3-formyl-4-hydroxybenzoate (3.55 g, 19.7 mmol) in DMF (20 ml) was added benzyl bromide (3.70 g, 21.67 mmol) and K$_2$CO$_3$ (4.1 g, 29.6 mmol). The reaction was stirred at ambient temperature overnight and the solvent evaporated to dryness (at reduced pressure). The residue was partitioned between ethyl ether and water and the aqueous layer extracted a second time with ethyl ether. The organic extracts were combined, washed with brine, dried (MgSO$_4$) and evaporated to give methyl 3-formyl-4-benzyloxybenzoate as an off-white solid which was used without further purification.

NMR (200 MHz, DMSO-d$_6$): δ10.40 (s, 1H), 8.22 (m, 2H), 7.44 (m, 6H), 5.38 (s, 2H), 3.85 (s, 3H).

To a stirred suspension of benzyl triphenylphosphonium bromide (8.96 g, 20.6 mmol) in freshly distilled THF (80 ml) was added LiN(SiMe$_3$)$_2$ (1N in THF, 23.6 ml). The resultant red solution was treated with a solution of methyl 4-benzyloxy-3-formylbenzoate, (5.5 g, 19.7 mmol) in THF (20 ml). The reaction was stirred at ambient temperature for 4 days, partitioned between ethyl ether and water and the water layer extracted with ethyl ether (2×). The combined organic extracts were washed with brine, dried (MgSO$_4$) and evaporated. The residue was purified by chromatography (eluant: ethyl ether/hexane) to give methyl 4-benzyloxy-3-(2-phenethenyl)benzoate as a colourless solid (5.1 g, 75%).

NMR (200 MHz, DMSO-d$_6$) (mixture of cis and trans isomers): δ8.24–6.6 (series of complex multiplets, taken together 15H), 5.31 and 5.20 (two singlets, together 2H) 3.85 and 3.72 (two singlets, together 3H).

To a solution of methyl 4-benzyloxy-3-(2-phenethenyl)-benzoate (0.5 g, 1.45 mmol) in methanol (12 ml) was added 10% palladium on carbon (0.05 g). The reaction was placed under an atmosphere of hydrogen and stirred vigorously until the uptake of hydrogen ceased, then filtered through Celite and evaporated to give the title product as a colourless solid (0.37 g, quantitative).

NMR (200 MHz, DMSO-d$_6$): δ10.28 (s, 1H), 7.66 (m, 1H), 7.24 (m, 5H), 6.88 (m, 1H), 3.66 (s, 3H), 2.83 (s, 4H).

Reference Example 59

Preparation of 4-acetyl-2-(2-phenethyl)phenol

To a stirred suspension of benzyl triphenylphosphonium bromide (7.44 g, 17.2 mmol) in freshly distilled THF (60 ml), under argon, was added a solution of LiN(SiMe$_3$)$_2$ (18.2 ml, 1N). The resulting red solution was allowed to stir for 30 minutes, then a solution of 5-bromo-2- benzyloxybenzaldehyde (5.0 g, 17.2 mmol) in freshly distilled THF (15 ml) added. The reaction was stirred at ambient temperature for 60 hours, treated with 1N aqueous HCl (60 ml) and extracted with ethyl ether (2×). The combined etherial extracts were washed with brine, dried ($MgSO_4$) and evaporated. The residue was purified by chromatography (eluant:hexane) to give β-(2-benzyloxy-5-bromophenyl)styrene as a white solid (5.5 g, 88%).

NMR (250 MHz, DMSO-$d_6$) (mixture of cis and trans isomers): δ7.6–6.5 (complex multiplets, taken together-15 H), 5.22 and 5.14 (two singlets, together, 2H).

To a solution of the above olefin (5.5 g, 15 mmol) in toluene (120 ml) and ethanol (120 ml) was added Wilkinson's catalyst (0.55 g). The reaction mixture was hydrogenated at 50° C. and 50 Bar for 18 hours, then evaporated. The residue was purified by chromatography (eluant: ethyl ether/hexane) to give 4-benzyloxy-3-(phenethyl) phenylbromide as a colourless oil which slowly crystallized (5.5 g, quantitative).

NMR (200 MHz, DMSO-$d_6$): δ7.25 (m, 1H), 5.13 (s, 2H), 2.83 (brs, 4H).

To a stirred solution of the 4-benzyloxy-3-(phenethyl) phenylbromide, (5.5 g, 15 mmol) in DMF (200 ml, dried) was added CuCN (3.32 g, 37 mmol). The reaction was heated to reflux and held at reflux for 20 hours, under argon. The reaction mixture was allowed to cool to ambient temperature, poured into ice water, treated with ethylene diamine (200 ml) and extracted with ethyl acetate (3×100 ml). The combined organic extracts were washed with brine (2×60 ml), dried ($MgSO_4$) and evaporated. The crude material was purified by chromatography to give 4-benzyloxy-3-phenethylbenzonitrile as a white solid (2.0 g, 43%).

NMR (250 MHz, DMSO-$d_6$): δ7.38 (m, 13H), 5.25 (s, 2H), 2.85 (m, 4H).

A solution of the cyano benzyl ether [from above] (1.0 g, 3.2 mmol) in ethanol (100 ml) was treated with 10% palladium on carbon. The reaction was placed under an atmosphere of hydrogen, stirred until the uptake of hydrogen ceased, filtered through celite and evaporated. The product was purified by chromatography (eluant: ethyl acetate/hexane) to give 4-cyano-2-(2-phenethyl)phenol as a white solid (0.64 g, 90%).

NMR (250 MHz, DMSO-$d_6$): δ10.58 (s, 1H), 7.47 (m, 2H), 7.23 (m, 5H), 6.95 (d, 1H), 2.83 (s, 4H).

A solution of 4-cyano-2-(2-phenethyl)phenol (0.64 g, 2.87 mmol) in THF (25 ml) under argon was cooled to −65° C. To the solution was added, over 10 minutes, a solution of methyl lithium (1.4M in ethyl ether, 5 ml). The resultant reaction was allowed to warm to ambient temperature over 3 hours, treated with water and dilute aqueous HCl to approx pH 1. The reaction was extracted with ethyl acetate (2×), the combined extracts washed with brine, dried ($MgSO_4$) and evaporated and the residue purified by chromatography (eluant: ethyl acetate/hexane) to give the title product as an off-white solid (0.5 g, 72%).

NMR (250 MHz, $CDCl_3$): δ7.45 (m, 2H), 7.26 (m, 5H), 6.80 (m, 1H), 5.68 (s, 1H), 2.94 (s, 4H), 2.50 (s, 3H).

Reference Example 60

Not used.

Reference Example 61

Not used.

Reference Example 62

Not used.

Reference Example 63

Preparation of methyl 4-[6-methanesulphonyl-2-(2-phenethyl)phenoxymethyl]benzoate A solution of methyl 4-[6-methylthio-2-(2-phenethyl)-phenoxymethyl]benzoate (0.38 g, 0.97 mmol) in dry $CH_2Cl_2$ (10 ml) was cooled to 0° C. To the cooled reaction was added a solution of m-CPBA (0.609 g, 55%, 1.94 mmol in 10 ml $CH_2Cl_2$), keeping the temperature below 2° C. The reaction mixture was stirred at 0° C. for 20 minutes and then allowed to warm to ambient temperature over 30 minutes. The reaction mixture was washed twice with saturated $NaHCO_3$ and the organic layer dried ($MgSO_4$) and evaporated.

NMR: (200 MHz, DMSO-$d_6$) δ2.95 (m, 4H), 3.25 (s, 3H), 3.88 (s, 3H), 5.1 (s, 2H), 7.15 (m, 5H), 7.39 (t, 1H), 7.63 (d, 2H), 7.75 (d, 2H), 8.03 (d, 2H).

Reference Example 64

Preparation of methyl 4-[4-benzenesulphonylmethyl-2-(2-phenethyl) phenoxymethyl]benzoate A solution of the methyl 4-[4-phenylthiomethyl-2-(2-phenethyl)phenoxymethyl]benzoate (0.43 g, 0.92 mmoles) in $CH_2Cl_2$ (5 ml) was cooled to 0° C. To this cooled solution was added portionwise, over 10 minutes, m-CPBA (0.58 g, [55%], 1.84 mmoles). The reaction was stirred at 0° C. for 1.75 hours. The reaction mixture was diluted with $CH_2Cl_2$ and washed twice with saturated $NaHCO_3$.

The organic phase was dried ($MgSO_4$) and evaporated. The residue was purified by chromatography (diethyl ether/hexane) to give the title product (0.33 g, 72%).

NMR (200 MHz, DMSO-$d_6$): δ2.71 (m, 4H), 3.86 (s, 3H), 4.54 (s, 2H), 5.18 (s, 2H), 6.89 (bs, 1H), 6.96 (bs, 2H), 7.18 (m, 5H), 7.64 (m, 7H), 7.98 (d, 2H)

Reference Example 65

Not used.

Reference Example 66

Preparation of tert-butyl 4-[6-methanesulphonylmethyl-2-(2-phenethyl) phenoxymethyl]benzoate and tert-butyl 4-[6-methanesulphinylmethyl-2-(2-phenethyl)-phenoxymethyl]benzoate To a cooled (0° C.) stirred solution of tert-butyl 4-[6-methylthiomethyl-2-(2-phenethyl)phenoxymethyl]benzoate (0.81, 1.8 mmol), in $CH_2Cl_2$ (30 ml) was added m-CPBA (1.13 g, (53%) 3.62 mmole) portionwise over 15 minutes. The reaction was stirred at 0° C. for 30 minutes and then allowed to warm to ambient temperature. The reaction was diluted with $CH_2 Cl_2$ and washed with saturated $NaHCO_3$. The organic phase was dried ($MgSO_4$) and evaporated and the residue was purified by chromatography (MeOH/$CH_2Cl_2$) to give the title products: tert-butyl 4-[6-methanesulphonylmethyl-2-(2-phenethyl)phenoxymethyl] benzoate (0.120 g, 14%) MS ($CI^+$): 478 $[M+NH_4]^+$ and tert butyl 4-[6-methanesulphinylmethyl-2-(2-phenethyl) phenoxymethyl]benzoate (0.48 g, 60%) MS($CI^+$): 465 $[M+H]^+$.

Reference Example 67

Preparation of methyl 3-(6-isopropyl-2-(2-phenethyl)phenoxymethyl)-benzoate

A solution of 6-isopropyl-2-(2-phenethyl)phenol (2.5 g, 19.42 mmol) in DMF (15 mL) was treated with $K_2CO_3$ (2.875 g, 20.83 mmol) and methyl 3-bromomethylbenzoate (2.62 g, 11.44 mmol). The reaction was stirred at ambient temperature overnight and then partitioned between ethyl acetate/$H_2O$. The organic phase was washed with $H_2O$(x4), dried (MgSO$_4$) and evaporated. The residue was purified by chromatography (eluant: diethyl ether/hexane) to give methyl 3-(6-isopropyl-2-(2-phenethyl)phenoxy-methyl) benzoate (3.3 g, 82%).

NMR: (200 MH$_2$, DMSO-d$_6$): δ8.11 (m, 1H), 7.96 (m, 1H), 7.74 (m, 1H), 7.57 (t, 1H), 7.15 (m, 8H), 4.87 (s, 2H), 3.87 (s, 3H), 3.30 (m, 1H), 2.86 (s, 4H), 1.19 (d, 6H).

Reference Example 68

Using a similar method to that of Reference Example 67, the compounds of Table XIV were prepared.

TABLE XIV

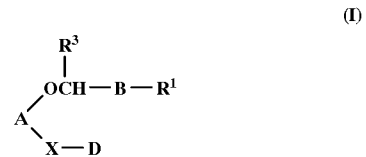

| R | Equivalents of bromo Compound | Equivalents of K$_2$CO$_3$ | MS | Footnotes |
|---|---|---|---|---|
| 6-Br | 1.0 | 2.0 | CI$^+$: 425 (M + H)+ | a |
| 4-Br | 1.1 | 1.3 | — | b |
| 4-OCH$_3$ | 1.1 | 1.3 | — | b |

Footnotes
a Reaction mixture filtered and evaporated and the residue purified by subjecting to chromatography, eluting with diethyl ether/hexane.
b Reaction mixture evaporated and residue partitioned between ethyl acetate and water and organic phase evaporated. Product used in subsequent step without further purification.

Reference Example 69

Preparation of tert-butyl 4-(6-N-methylcarbamoyl-2-(2-phenethyl)phenoxymethyl)benzoate A solution of tert butyl 4-(6-methoxycarbonyl-2-(2-phenethyl)phenoxymethyl)benzoate (0.42 g, 0.94 mmol) in methylamine (15 ml, 33% w/w in industrial methylated spirits) was placed in a carius tube and heated at 100° C. for 12 hours. The reaction mixture was evaporated. The residue was purified by chromatography (dichloromethane, methanol) to give the desired product (0.29 g, 70%). MS (FAB+): 446 (M+H)$^+$. The starting material was prepared according to Reference example 7 Table XVII compound 1.

Reference Example 70

Preparation of 3-chloro-2-hydroxybenzaldehyde a) A suspension of 3-chlorosalicylic acid (1.5 g, 8.7 mmol) in dichloromethane (10 ml) was treated with oxalyl chloride (1.59 g, 13 mmol) and 1 drop of DMF. The reaction was stirred at ambient temperature for 2 hours, evaporated to dryness and used immediately in the next step.

b) 3-Chloro-2-hydroxybenzoylchloride (8.7 mmol) was dissolved in diglyme (10 ml) and cooled to −70° C. under argon. Lithium tritertbutoxyaluminohydride (0.5M, 34.8 ml 17.4 mmol) was added via syringe keeping the temperature below −60° C. The reaction was stirred at −60° C. for 2% hours. The reaction mixture was poured onto ice, acidified with concentrated HCl and extracted with ethyl acetate (2×).

The organic phases were combined, dried over MgSO$_4$ and evaporated. Flash chromatography (eluant: CH$_2$Cl$_2$/hexanes) gave the title product (0.2 g, 1.3 mmol). MS (CI$^+$) (M+NH$_4$)$^+$ 174

What is claimed is:
1. A compound of the formula (I):

$$\begin{array}{c} R^3 \\ | \\ \diagdown OCH-B-R^1 \\ A \\ \diagdown X-D \end{array}$$ (I)

wherein:
A is an 8-, 9- or 10-membered bicyclic heteroaryl, a 5- or 6-membered heteroaryl, naphthyl or phenyl, or any of the foregoing substituted with E where E is selected from the group consisting of C$_1$–C$_6$-alkyl, mono- or di-substituted C$_1$–C$_6$-alkyl (where the substituent is independently selected from hydroxy, amino, halo, nitro, C$_1$–C$_4$-alkyl-S(O)$_p$-, C$_1$–C$_4$-alkoxy, phenyl-S(O) $_p$-, or cyano), halo, trifluoromethyl, nitro, hydroxy, amino, C$_1$–C$_4$-alkylamino, di-C$_1$–C$_4$-alkylamino, cyano, C$_1$C$_6$-alkoxy, C$_1$–C$_6$-alkyl-S(O)$_p$-, phenyl-S(O) $_p$-, carbamoyl, C$_2$–C$_6$-alkenyl, C$_2$–C$_6$-alkynyl, C$_3$–C$_7$-cycloalkyl, C$_3$–C$_7$-cycloalkyl-C$_1$–C$_3$-alkyl, C$_3$–C$_7$-cycloalkyl-C$_2$–C$_3$-alkenyl, C$_3$–C$_7$-cycloalkyl-C$_2$–C$_3$-alkynyl, C$_1$–C4-alkoxycarbonylamino, C$_1$–C4-alkanoylamino, C$_1$–C4-alkanoyl-(N-C$_1$–C$_4$-alkyl) amino, C$_1$–C4-alkanesulphonamido, benzenesulphonamido, aminosulphonyl, C$_1$–C$_4$-alkylaminosulphonyl, di-C$_1$C$_4$-alkyl-aminosulphonyl, C$_1$–C$_4$-alkoxycarbonyl, C$_2$–C$_4$-alkanoyloxy, formyl-C$_1$–C$_4$-alkyl, trifluoro-C$_1$–C$_3$-alkylsulphonyl, hydroxyimino-C$_1$–C$_6$-alkyl, C$_1$–C$_4$-alkoxyimino-C$_1$–C$_6$-alkyl, C$_1$–C$_6$-alkylcarbamoylamino, phenyl, C$_1$–C$_4$-alkylcarbamoyl and di-C$_1$–C$_4$-alkyl-carbamoyl; provided that if A is a ring structure, the —OCH(R$^3$)- and -X- linking groups are positioned in a 1,2 relationship to one another on ring carbon atoms of A, wherein p is 0, 1 or 2;

B is phenyl or a 5- or 6-membered heteroaryl ring, or either of the foregoing substituted with G, where G is selected from the group consisting of halo, trifluoromethyl, nitro, hydroxy, C$_1$–C$_6$-alkyl, C$_3$–C$_7$-cycloalkyl, C$_3$–C$_7$-cycloalkyl-C$_1$–C$_3$-alkyl, amino, C$_1$–C$_4$-alkylamino, di-C$_1$–C$_4$-alkyl-amino, cyano, -S(O)$_p$-C$_1$–C$_6$-alkyl, carbamoyl, C$_1$–C$_4$-alkylcarbamoyl and di-C$_1$–C$_4$-alkyl-carbamoyl;

D is pyridyl, pyrazinyl, pyrimidinyl, pyridazinyl, pyrrolyl, thienyl, furyl, pyrazolyl, thiazolyl, isothiazolyl, oxazolyl, isoxazolyl or phenyl, or any of the foregoing mono- or di-substituted with halo, trifluoromethyl, nitro, hydroxy, amino, C$_1$–C$_4$-alkylamino, di-C$_1$–C$_4$-alkyl-amino, cyano, C$_1$–C$_6$-alkoxy, —S(O)$_p$-C$_1$–C$_4$-alkyl, —S(O)$_p$-phenyl, C $_1$–C$_4$-alkanoyl, C$_1$–C$_4$-alkyl or C$_1$–C$_4$-alkyl mono-substituted with hydroxy, halo, nitro, cyano or amino;

R$^1$ is carboxy, carboxy-C$_1$–C$_3$-alkyl, tetrazolyl, tetrazolyl-C$_1$–C$_3$-alkyl, tetronic acid, hydroxamic acid, sulphonic acid, or R$^1$ is of the formula -CONR$^a$R$^{a1}$:
where R$^a$ is hydrogen or C$_1$–C$_6$-alkyl, and R$^{a1}$ is J or hydrogen, where J is selected from C$_1$–C$_6$-alkyl, C$_2$–C$_6$-alkenyl, C$_2$–C$_6$-alkynyl, C$_3$–C$_7$-cycloalkyl, $C_3$–$C_7$-cycloalkyl-$C_1$–$C_6$-alkyl, $C_3$–$C_7$-cycloalkyl-$C_2$–$C_6$-alkenyl, $C_3$–$C_7$-cycloalkyl-$C_2$–$C_6$-alkynyl, $C_5$–$C_7$-cycloalkenyl, $C_5$–$C_7$-cycloalkenyl-$C_1$–$C_6$-alkyl, $C_5$–$C_7$-cycloalkenyl-$C_2$–$C_6$-alkenyl, $C_5$–$C_7$-cycloalkenyl-$C_2$–$C_6$-alkynyl, or $R^{a1}$ is J mono-substituted with a 5- or 6-membered saturated or partially-saturated heterocyclic ring, a 5- or 6-membered heteroaryl ring or a 5- or 6-membered heteroaryl-$C_1$–$C_3$-alkyl; or where $R^a$ and $R^{a1}$ together with the nitrogen to which they are attached form a group having the formula —NH—CH($R^C$)—COOR$^D$ wherein $R^C$ is hydrogen, $C_1$–$C_6$-alkyl, $C_2$–$C_6$-alkenyl, $C_2$–$C_6$-alkynyl, phenyl, phenyl($C_1$–$C_3$-alkyl), 5- or 6-membered heteroaryl or 5- or 6-membered heteroaryl($C_1$–$C_3$-alkyl) and $R^D$ is H or $C_1$–$C_6$-alkyl, wherein any alkyl, alkenyl, alkynyl, phenyl or heteroaryl group of the foregoing is either unsubstituted or mono- substituted with E;

$R^1$ is of the formula —CONHSO$_2$J;

X is of the formula —(CHR$^4$)$_n$— or —(CHR$^4$)$_r$CR$^4$=CR$^4$(CHR$^4$)$_q$—, where n is 1, 2 or 3; and r and q are either both 0, or r is 0 and q is 1, or r is 1 and q is 0; and $R^3$ and $R^4$ are independently selected from hydrogen or $C_1$–$C_4$-alkyl; wherein:

when B is a 6-membered ring, $R^1$ is positioned on ring B in a 1,3 or a 1,4 relationship with the —OCH($R^3$)— linking group, or when B is a 5-membered ring, $R^1$ is positioned in a 1,3 relationship with the —OCH($R^3$)— linking group;

or an N-oxide of any of the foregoing compounds;

or any of the foregoing compounds having S-oxides of sulphur containing rings therein;

or a pharmaceutically-acceptable salt or an in vivo hydrolysable ester or amide of any of the foregoing compounds;

provided the compound of formula (I) is not 4-(2-benzyl-3-hydroxy-4-formylphenoxymethyl)-3-methoxybenzoic acid, or 4-(2-(3-phenylprop-2-en-1-yl)-3-hydroxy-4-formylphenoxymethyl)-3-methoxybenzoic acid.

2. A compound according to claim 1, wherein A is phenyl, pyridyl, pyrimidyl, pyrazinyl, pyridazinyl, thienyl or 1,2,3-thiadiazolyl or any of the foregoing mono- or di-substituted with E.

3. A compound according to claim 1, wherein B is phenyl, pyridyl, thiazolyl, thienyl, thiadiazolyl, pyrazinyl, pyridazinyl or pyrimidyl or any of the foregoing mono- or di-substituted with G.

4. A compound according to claim 1, wherein D is phenyl or phenyl mono- or di-substituted with halo, trifluoromethyl, nitro, hydroxy, amino, $C_1C_4$-alkylamino, di-$C_1$–$C_4$-alkylamino, cyano, $C_1C_6$-alkoxy, -S(O)$_p$-$C_1$–$C_4$-alkyl, -S(O)$_p$-phenyl, $C_1$–$C_4$-alkanoyl, $C_1$–$C_4$-alkyl or $C_1$–$C_4$-alkyl mono- or di-substituted with hydroxy, halo, nitro, cyano or amino.

5. A compound according to claim 1, having the formula (V).

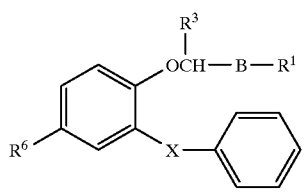

wherein:

X is —(CH$_2$)$_2$— or —CH=CH—;

B is phenyl, thiadiazolyl or pyridyl; and $R^6$ is hydrogen, halo, trifluoromethyl, nitro, hydroxy, amino, cyano, $C_1$–$C_6$-alkoxy, $C_1$–$C_6$-alkyl-S(O)$_p$, phenyl-S(O)$_p$, $C_1$–$C_6$-alkyl mono- or di-substituted by hydroxy, amino, halo, nitro or cyano, $C_3$–$C_7$-cycloalkyl, $C_3$–$C_7$-cycloalkyl-$C_1$–$C_3$-alkyl, carbamoyl, $C_1$–$C_4$-alkylcarbamoyl, di-$C_1$–$C_4$-alkyl-carbamoyl, $C_2$–$C_6$-alkenyl, $C_2$–$C_6$-alkynyl, $C_1$–$C_4$-alkoxycarbonylamino, $C_1$–$C_4$-alkanoylamino, $C_1$–$C_4$-alkanoyl(N-$C_1$–$C_4$-alkyl)amino, $C_1$–$C_4$-alkanesulphonamido, benzenesulphonamido, aminosulphonyl, $C_1$–$C_4$-alkylaminosulphonyl, di-$C_1$–$C_4$-alkyl-aminosulphonyl, $C_1$–$C_4$-alkoxycarbonyl, $C_2$–$C_4$-alkanoyloxy, $C_1$–$C_6$-alkanoyl, formyl-$C_1$–$C_4$-alkyl, trifluoro-$C_1$–$C_3$-alkylsulphonyl, hydroxyimino-$C_1$–$C_6$-alkyl, $C_1$–$C_4$-alkoxyimino-$C_1$–$C_6$-alkyl or $C_1$–$C_6$-alkylcarbamoylamino.

6. A compound according to claim 1, selected from the group consisting of:

4-[6-bromo-2-(phenethyl)phenoxymethyl]benzoic acid;
4-[5-nitro-2-(phenethyl)phenoxymethyl]benzoic acid;
4-[4-chloro-6-methyl-2-(phenethyl)phenoxymethyl]benzoic acid;
4-[5-bromo-6-cyano-2-(phenethyl)phenoxymethyl]benzoic acid;
4-[5-chloro-2-(phenethyl)phenoxymethyl]benzoic acid;
4-[4-cyanomethyl-2-(phenethyl)phenoxymethyl]benzoic acid;
4-[2-(phenethyl)phenoxymethyl]benzoic acid;
4-[6-bromo-2-(phenethyl)phenoxymethyl]-2-hydroxybenzoic acid;
4-[5-methyl-2-(phenethyl)phenoxymethyl]benzoic acid;
4-[2-(phenethyl)-6-phenylphenoxymethyl]benzoic acid;
4- [6-amino-2-(phenethyl)phenoxymethyl]benzoic acid;
4- [6-methanethio-2-(phenethyl )phenoxymethyl]benzoic acid;
4-[4-(1-(hydroxyimino)ethyl)-2-(phenethyl)phenoxymethyl]benzoic acid;
4-[4-methyl-2-(phenethyl)phenoxymethyl]benzoic acid;
4-[4-bromo-2-(phenethyl)phenoxymethyl]benzoic acid;
4-[4-methoxy-2-(phenethyl)phenoxymethyl]benzoic acid;
4-[6-cyano-2-(phenethyl)phenoxymethyl]benzoic acid;
4-[6-cyano-4-methyl-2-(phenethyl)phenoxymethyl]benzoic acid;
4-[4-chloro-2-(phenethyl)phenoxymethyl]benzoic acid;
4-[6-benzenesulphonylmethyl-2-(phenethyl)phenoxymethyl]benzoic acid;
4-[4-methanethio-2-(phenethyl)phenoxymethyl]benzoic acid;
4-[5-bromo-2-(phenethyl)phenoxymethyl]benzoic acid;
4-[6-isopropyl-2-(phenethyl)phenoxymethyl]benzoic acid;
5- [4-(2-(phenethyl)-6-phenylphenoxymethyl)phenyl] tetrazole;
5- [4-(4-hydroxy-2-(phenethyl)phenoxymethyl)phenyl] tetrazole;

5-[4-(4-methoxy-2-(phenethyl)phenoxymethyl)phenyl]tetrazole;
5-[4-(2-(phenethyl)phenoxymethyl)phenyl]tetrazole;
5-[4-(4-chloro-2-(phenethyl)phenoxymethyl)phenyl]tetrazole;
5-[4-(4-bromo-2-(phenethyl)phenoxymethyl)phenyl]tetrazole;
5-[4-(6-bromo-2-(phenethyl)phenoxymethyl)phenyl]tetrazole; and
5-[4-(6-isopropyl-2-(phenethyl)phenoxymethyl)phenyl]tetrazole, or
a pharmaceutically-acceptable salt or an in vivo hydrolysable ester or amide of any of the foregoing compounds.

7. A pharmaceutical composition which comprises a compound according to claim 1 and a pharmaceutically-acceptable excipient or diluent.

8. A method of relieving pain in a patient suffering therefrom, said method comprising administering a therapeutically effective amount of compound according to claim 1.

9. A process for preparing a compound of formula (I) according to claim 1, said process comprising:

ia) when X is —(CHR$^4$)$_n$—, and n is 2 or 3, reducing a compound of formula:

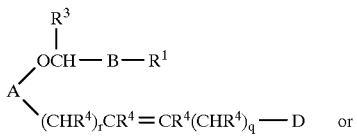

ib) when X is -(CHR$^4$)$_n$- and n is 1, 2 or 3, reacting a compound of formula:

with a compound of formula:

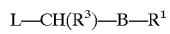

wherein L is a leaving group; or ic) when A is an activated heterocyclic ring, reacting a compound of formula:

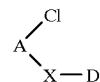

with a compound of formula:

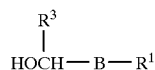

where, in any of the foregoing steps, ia), ib) or ic), any of A, B, D, X, R$^1$, R$^3$ and R$^4$ bear protective groups when necessary;

ii) removing any of said protecting groups; and iii) forming a pharmaceutically-acceptable salt of any of the foregoing compounds.

10. A process according to step ia), ib) or ic) of claim 9, for preparing a compound having the formula (V):

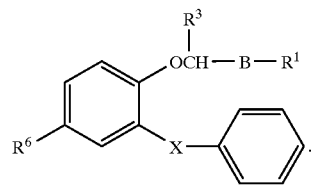

(V)

* * * * *